United States Patent
Dong et al.

(10) Patent No.: US 10,655,141 B2
(45) Date of Patent: May 19, 2020

(54) PLANT EPSP SYNTHASES AND METHODS OF USE

(71) Applicant: PIONEER HI-BRED INTERNATIONAL, INC., Johnston, IA (US)

(72) Inventors: Yuxia Dong, Fremont, CA (US); Michael Lassner, Portland, OR (US); Jian Lu, Union City, CA (US); Emily Ng, San Leandro, CA (US); Phillip A. Patten, Portola Valley, CA (US); Daniel Siehl, Menlo Park, CA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 87 days.

(21) Appl. No.: 15/764,388

(22) PCT Filed: Sep. 29, 2016

(86) PCT No.: PCT/US2016/054399
§ 371 (c)(1),
(2) Date: Mar. 29, 2018

(87) PCT Pub. No.: WO2017/059045
PCT Pub. Date: Apr. 6, 2017

(65) Prior Publication Data
US 2019/0024110 A1 Jan. 24, 2019

Related U.S. Application Data

(60) Provisional application No. 62/234,818, filed on Sep. 30, 2015.

(51) Int. Cl.
*C12N 15/82* (2006.01)
*C12N 9/10* (2006.01)

(52) U.S. Cl.
CPC ....... *C12N 15/8275* (2013.01); *C12N 9/1092* (2013.01); *C12Y 205/01019* (2013.01)

(58) Field of Classification Search
None
See application file for complete search history.

(56) References Cited

U.S. PATENT DOCUMENTS

| 2013/0212737 A1* | 8/2013 | Lira | ...................... C07K 14/415 800/278 |
| 2014/0206850 A1* | 7/2014 | Bundock | ............ C12N 15/8275 536/23.2 |

FOREIGN PATENT DOCUMENTS

| WO | WO97/04103 | * | 2/1997 | ............... A01H 5/00 |
| WO | WO 1997/04103 A2 | | 2/1997 | |
| WO | WO 01/24615 A1 | | 4/2001 | |
| WO | WO 03/013226 A2 | | 2/2003 | |
| WO | WO 2015/026886 A1 | | 2/2015 | |

OTHER PUBLICATIONS

Dill, Gerald M, "Glyphosate-resistant crops: history, status and future," Pest Management Science, Wiley & Sons, Bognor Regis, (2005), vol. 61, No. 3, pp. 219-224.

Eschenburg, Susanne, et al., "How the mutation glycine96 to alanine confers glyphosate insensitivity to 50enolpyruvyl shikimate-3-phosphate synthase from *Escherichia coli*," Planta Springer Verlag (2002), vol. 216, No. 1, pp. 129-135.

Sost D, et al., "Substitution of Gly-96 to Ala in the 5-enolpyruvylshikimate 3 phosphate synthase of Klebsiella pneumoniae results in a greatly reduced affinity for the herbicide glyphosate," Archives of Biochemistry and Biophysics, Academic Press (1990), vol. 282, No. 2, pp. 433-436.

The International Search Report and Written Opinion of the International Search Authority for International Application No. PCT/US2016/054399, dated Feb. 13, 2017.

* cited by examiner

*Primary Examiner* — Ashley K Buran

(57) ABSTRACT

Compositions and methods comprising polynucleotides and polypeptides having EPSP (5-enolpyruvylshikimate-3-phosphate) synthase (EPSPS) activity are provided. In specific embodiments, the sequence has an improved property, such as, but not limited to, improved catalytic capacity in the presence of the inhibitor, glyphosate. Further provided are nucleic acid constructs, plants, plant cells, explants, seeds and grain having the EPSPS sequences. Various methods of employing the EPSPS sequences are provided. Such methods include methods for producing a glyphosate tolerant plant, plant cell, explant or seed and methods of controlling weeds in a field containing a crop employing the plants and/or seeds disclosed herein.

24 Claims, 10 Drawing Sheets

Specification includes a Sequence Listing.

|          |       | 1                                                  50 |
|----------|-------|--------------------------------------------------------|
| MaizeWT  | (1)   | MAGAEEIVLQPIKEISGTVKLPGSKSLSNRILLLAALSEGTTVVDNLLNS |
| MaizeH6  | (1)   | MRGWEEIVLQPIKEISGTVKLPGSKSLSNRILLLAALSEGTTVVDNLLNS |
|          |       | 51                                                100 |
| MaizeWT  | (51)  | EDVHYMLGALRTLGLSVEADKAAKRAVVVGCGGKFPVEDAKEEVQLFLGN |
| MaizeH6  | (51)  | EDVHYMLGALRTLGLSVEADKQAKRAVVVGCGGRFPVEDAKEEVQLFCGN |
|          |       | 101                                               150 |
| MaizeWT  | (101) | AGTAMRPLTAAVTAAGGNATYVLDGVPRMRERPIGDLVVGLKQLGADVDC |
| MaizeH6  | (101) | AATAMRPLTAAVTAAGGNATYVLDGVPRMRERPIGDLVVGLKQLGADVDC |
|          |       | 151                                               200 |
| MaizeWT  | (151) | FLGTDCPPVRVNGIGGLPGGKVKLSGSISSQYLSALLMAAPLALGDVEIE |
| MaizeH6  | (151) | FLGTDCPPVRVNGIGGLPGGKVKLSGSISSQYLSALLMAAPLALGDVEIE |
|          |       | 201                                               250 |
| MaizeWT  | (201) | IIDKLISIPYVEMTLRLMERFGVKAEHSDSWDRFYIKGGQKYKSPKNAYV |
| MaizeH6  | (201) | IIDKLISLPYVEMTLRLMERFGVKAEHSDSWDRFYIKGGQKYKSPKNAYV |
|          |       | 251                                               300 |
| MaizeWT  | (251) | EGDASSASYFLAGAAITGGTVTVEGCGTTSLQGDVKFAEVLEMMGAKVTW |
| MaizeH6  | (251) | EGDASSASYFLAGAAITGGTVTVEGCGTASLQGDVKFAEVLEMMGAKVTW |
|          |       | 301                                               350 |
| MaizeWT  | (301) | TTTSVTVTGPPREPFGRKHLKAIDVNMNKMPDVAMTLAVVALFADGPTAI |
| MaizeH6  | (301) | TSTSVTVTGPPREPFGRKHLKAIDVNMNKMPDVAMTLAVVALFADGPTAI |
|          |       | 351                                               400 |
| MaizeWT  | (351) | RDVASWRVKETERMVAIRTELTKLGASVEEGPDYCIITPPEKLNVTAIDT |
| MaizeH6  | (351) | RDVASWRVKESERMVAIRTELTKLGASVEEGPDYCIITPPGKLNVTAIDT |
|          |       | 401                                               445 |
| MaizeWT  | (401) | YDDHRMAMAFSLAACAEVPVTIRDPGCTRKTFPDYFDVLSTFVKN |
| MaizeH6  | (401) | YGDHRMAMAFSLAACGEVPVTIRDPGCTRKTFPDYFDRLSQFVKN |

FIG. 1

```
            1                                                  50
SoyWT  (1)  AAAEKPSTSPEIVLEPIKDFSGTITLPGSKSLSNRILLLAALSEGTTVVD
SoyH6  (1)  AAARKWSTSPEIVLEPIKDFSGTITLPGSKSLSNRILLLAALSEGTTVVD
            51                                                100
SoyWT  (51) NLLYSEDIHYMLGALRTLGLRVEDDKTTKQAIVEGCGGLFPTSKESKDEI
SoyH6  (51) NLLYSEDIHYMLGALRTLGLRVEDDKQTKQAIVEGCGGRFPTSKESKDEI
            101                                               150
SoyWT (101) NLFLGNAGTAMRPLTAAVVAAGGNASYVLDGVPRMRERPIGDLVAGLKQL
SoyH6 (101) NLFCGNAATAMRPLTAAVVAAGGNASYVLDGVPRMRERPIGDLVAGLKQL
            151                                               200
SoyWT (151) GADVDCFLGTNCPPVRVNGKGGLPGGKVKLSGSVSSQYLTALLMAAPLAL
SoyH6 (151) GADVDCFLGTNCPPVRVNGKGGLPGGKVKLSGSVSSQYLTALLMAAPLAL
            201                                               250
SoyWT (201) GDVEIEIVDKLISVPYVEMTLKLMERFGVSVEHSGNWDRFLVHGGQKYKS
SoyH6 (201) GDVEIEIVDKLISLPYVEMTLKLMERFGVSVEHSGNWDRFLVHGGQKYKS
            251                                               300
SoyWT (251) PGNAFVEGDASSASYLLAGAAITGGTITVNGCGTSSLQGDVKFAEVLEKM
SoyH6 (251) PGNAFVEGDASSASYLLAGAAITGGTITVNGCGTASLQGDVKFAEVLEKM
            301                                               350
SoyWT (301) GAKVTWSENSVTVSGPPRDFSGRKVLRGIDVNMNKMPDVAMTLAVVALFA
SoyH6 (301) GAKVTWSSNSVTVSGPPRDFSGRKVLRGIDVNMNKMPDVAMTLAVVALFA
            351                                               400
SoyWT (351) NGPTAIRDVASWRVKETERMIAICTELRKLGATVEEGPDYCVITPPEKLN
SoyH6 (351) NGPTAIRDVASWRVKESERMIAICTELRKLGATVEEGPDYCVITPPGKLN
            401                                               450
SoyWT (401) VTAIDTYDDHRMAMAFSLAACGDVPVTIKDPGCTRKTFPDYFEVLERLTK
SoyH6 (401) VTAIDTYGDHRMAMAFSLAACGDVPVTIKDPGCTRKTFPDYFERLEQLTK
            451
SoyWT (451) H
SoyH6 (451) H
```

FIG. 2

```
                    1                                                50
SunFlowerWT    (1)  MAIHINNISNFTSNLTNTHNPNSSSKSSPSSFLSFGSNFNNPMMNLASVS
SunFlowerH6    (1)  --------------------------------------------------
                    51                                               100
SunFlowerWT   (51)  CKQNDQKRSXAVAASVATTQKTSTAPEEIVLKPIKEISGTVNLPGSKSLS
SunFlowerH6    (1)  ----------------MATTRKWSTAPEEIVLKPIKEISGTVNLPGSKSLS
                    101                                              150
SunFlowerWT  (101)  NRILLLAALAEGTTVVXNLLNSDDVHYMLGALRALGLNVEENGEIKRATV
SunFlowerH6   (36)  NRILLLAALAEGTTVVDNLLNSDDVHYMLGALRALGLNVEENGQIKRATV
                    151                                              200
SunFlowerWT  (151)  EGCGGVFPVGKEAKDEIQLFLGNAGTAMRPLTAAVTAAGGNSSYILDGVP
SunFlowerH6   (86)  EGCGGRFPVGKEAKDEIQLFCGNAATAMRPLTAAVTAAGGNSSYILDGVP
                    201                                              250
SunFlowerWT  (201)  RMRERPIGDLVTGLKQLGADVDCFLGTNCPPVRVAANGGLPGGKVKLSGS
SunFlowerH6  (136)  RMRERPIGDLVTGLKQLGADVDCFLGTNCPPVRVAANGGLPGGKVKLSGS
                    251                                              300
SunFlowerWT  (251)  ISSQYLTALLMAAPLALGDVEIEIIDKLISVPYVEMTLKLMERFGVSVEH
SunFlowerH6  (186)  ISSQYLTALLMAAPLALGDVEIEIIDKLISLPYVEMTLKLMERFGVSVEH
                    301                                              350
SunFlowerWT  (301)  SDSWDKFYVRGGQKYKSPGNAYVEGDASSASYFLAGAAITGGTVTVEGCG
SunFlowerH6  (236)  SDSWDKFYVRGGQKYKSPGNAYVEGDASSASYFLAGAAITGGTVTVEGCG
                    351                                              400
SunFlowerWT  (351)  TSSLQGDVKFAEVLGQMGAEVTWTENSVTVRGPPRNASGRGHLRPVDVNM
SunFlowerH6  (286)  TASLQGDVKFAEVLGQMGAEVTWTSNSVTVRGPPRNASGRGHLRPVDVNM
                    401                                              450
SunFlowerWT  (401)  NKMPDVAMTLAVVALYADGPTAIRDVASWRVKETERMIAICTELRKLGAT
SunFlowerH6  (336)  NKMPDVAMTLAVVALYADGPTAIRDVASWRVKESERMIAICTELRKLGAT
                    451                                              500
SunFlowerWT  (451)  VEEGPDYCVITPPEKLNVTAIDTYDDHRMAMAFSLAACADVPVTIKDPGC
SunFlowerH6  (386)  VEEGPDYCVITPPGKLNVTAIDTYGDHRMAMAFSLAACGDVPVTIKDPGC
                    501              518
SunFlowerWT  (501)  TRKTFPDYFEVLERFTKH
SunFlowerH6  (436)  TRKTFPDYFERLEQFTKH
```

FIG. 3

```
                   1                                                50
RiceWT    (1)   MASNAAAAAAVSLDQAVAASAAFSSRKQLRLPAAARGGMRVRVRARGRRE
RiceH6    (1)   -------------------------------------------------
                51                                               100
RiceWT   (51)   AVVVASASSSSVAAPAAKAEEIVLQPIREISGAVQLPGSKSLSNRILLLS
RiceH6    (1)   ------------MAPARKWEEIVLQPIREISGAVQLPGSKSLSNRILLLS
                101                                              150
RiceWT  (101)   ALSEGTTVVDNLLNSEDVHYMLEALKALGLSVEADKVAKRAVVVGCGGKF
RiceH6   (39)   ALSEGTTVVDNLLNSEDVHYMLEALKALGLSVEADKCAKRAVVVGCGGRF
                151                                              200
RiceWT  (151)   PVEKDAKEEVQLFLGNAGTAMRPLTAAVTAAGGNATYVLDGVPRMRERPI
RiceH6   (89)   PVEKDAKEEVQLFCGNAATAMRPLTAAVTAAGGNATYVLDGVPRMRERPI
                201                                              250
RiceWT  (201)   GDLVVGLKQLGADVDCFLGTECPPVRVKGIGGLPGGKVKLSGSISSQYLS
RiceH6  (139)   GDLVVGLKQLGADVDCFLGTECPPVRVKGIGGLPGGKVKLSGSISSQYLS
                251                                              300
RiceWT  (251)   ALLMAAPLALGDVEIEIIDKLISIPYVEMTLRLMERFGVKAEHSDSWDRF
RiceH6  (189)   ALLMAAPLALGDVEIEIIDKLISLPYVEMTLRLMERFGVKAEHSDSWDRF
                301                                              350
RiceWT  (301)   YIKGGQKYKSPGNAYVEGDASSASYFLAGAAITGGTVTVQGCGTTSLQGD
RiceH6  (239)   YIKGGQKYKSPGNAYVEGDASSASYFLAGAAITGGTVTVQGCGTASLQGD
                351                                              400
RiceWT  (351)   VKFAEVLEMMGAKVTWTDTSVTVTGPPREPYGKKHLKAVDVNMNKMPDVA
RiceH6  (289)   VKFAEVLEMMGAKVTWTSTSVTVTGPPREPYGKKHLKAVDVNMNKMPDVA
                401                                              450
RiceWT  (401)   MTLAVVALFADGPTAIRDVASWRVKETERMVAIRTELTKLGASVEEGPDY
RiceH6  (339)   MTLAVVALFADGPTAIRDVASWRVKESERMVAIRTELTKLGASVEEGPDY
                451                                              500
RiceWT  (451)   CIITPPEKLNITAIDTYDDHRMAMAFSLAACADVPVTIRDPGCTRKTFPN
RiceH6  (389)   CIITPPCKLNITAIDTYGDHRMAMAFSLAACGDVPVTIRDPGCTRKTFPN
                501       511
RiceWT  (501)   YFDVLSTFVRN
RiceH6  (439)   YFDRLSQFVRN
```

FIG. 4

```
                    1                                                50
SorghumWT   (1)    -AAGAEEIVLQPIKEISGTVKLPGSKSLSNRILLLAALSEGTTVVDNLLN
SorghumH6   (1)    MARGWEEIVLQPIKEISGTVKLPGSKSLSNRILLLAALSEGTTVVDNLLN
                    51                                               100
SorghumWT   (50)   SEDVHYMLGALNTLGLSVEADKVAKRAVVVGCGGKFPVEDAKEEVQLFLG
SorghumH6   (51)   SEDVHYMLGALNTLGLSVEADKQAKRAVVVGCGGRFPVEDAKEEVQLFCG
                    101                                              150
SorghumWT   (100)  NAGTAMRPLTAAVTAAGGNATYVLDGVPRMRERPIGDLVVGLKQLGADVD
SorghumH6   (101)  NAATAMRPLTAAVTAAGGNATYVLDGVPRMRERPIGDLVVGLKQLGADVD
                    151                                              200
SorghumWT   (150)  CFLGTDCPPVRINGIGGLPGGKVKLSGSISSQYLSALLMAAPLALGDVEI
SorghumH6   (151)  CFLGTDCPPVRINGIGGLPGGKVKLSGSISSQYLSALLMAAPLALGDVEI
                    201                                              250
SorghumWT   (200)  EIIDKLISIPYVEMTLRLMERFGVKAEHSDSWDRFYIKGGQKYKSPKNAY
SorghumH6   (201)  EIIDKLISLPYVEMTLRLMERFGVKAEHSDSWDRFYIKGGQKYKSPKNAY
                    251                                              300
SorghumWT   (250)  VEGDASSASYFLAGAAITGGTVTVEGCGTTSLQGDVKFAEVLEMMGAKVT
SorghumH6   (251)  VEGDASSASYFLAGAAITGGTVTVEGCGTASLQGDVKFAEVLEMMGAKVT
                    301                                              350
SorghumWT   (300)  WTETSVTVTGPPRQPFGRKHLKAIDVNMNKMPDVAMTLAVVALFADGPTA
SorghumH6   (301)  WTSTSVTVTGPPRQPFGRKHLKAIDVNMNKMPDVAMTLAVVALFADGPTA
                    351                                              400
SorghumWT   (350)  IRDVASWRVKETERMVAIRTELTKLGASVEEGPDYCIITPPEKLNVTAID
SorghumH6   (351)  IRDVASWRVKESERMVAIRTELTKLGASVEEGPDYCIITPPGKLNVTAID
                    401                                          446
SorghumWT   (400)  TYDDHRMAMAFSLAACAEVPVTIRDPGCTRKTFPDYFDVLSTFVKN
SorghumH6   (401)  TYGDHRMAMAFSLAACGEVPVTIRDPGCTRKTFPDYFDRLSQFVKN
```

FIG. 5

```
            1                                                50
WheatWT  (1) APSGAEEVVLQPIREISGAVQLPGSKSLSNRILLLSALSEGTTVVDNLLN
WheatH6  (1) APRGWEEVVLQPIREISGAVQLPGSKSLSNRILLLSALSEGTTVVDNLLN
            51                                               100
WheatWT (51) SEDVHYMLEALEALGLSVEADKVAKRAVVVGCGGRFPVEKDAQEEVKLFL
WheatH6 (51) SEDVHYMLEALEALGLSVEADKQAKRAVVVGCGGRFPVEKDAQEEVKLFC
            101                                              150
WheatWT (101) GNAGTAMRPLTAAVVAAGGNATYVLDGVPRMRERPIGDLVVGLQQLGADA
WheatH6 (101) GNAATAMRPLTAAVVAAGGNATYVLDGVPRMRERPIGDLVVGLQQLGADA
            151                                              200
WheatWT (151) DCFLGTNCPPVRINGKGGLPGGKVKLSGSISSQYLSSLLMAAPLALEDVE
WheatH6 (151) DCFLGTNCPPVRINGKGGLPGGKVKLSGSISSQYLSSLLMAAPLALEDVE
            201                                              250
WheatWT (201) IEIIDKLISVPYVEMTLKLMERFGVTAEHSDSWDRFYIKGGQKYKSPGNA
WheatH6 (201) IEIIDKLISLPYVEMTLKLMERFGVTAEHSDSWDRFYIKGGQKYKSPGNA
            251                                              300
WheatWT (251) YVEGDASSASYFLAGAAITGGTVTVEGCGTTSLQGDVKFAEVLEMMGAKV
WheatH6 (251) YVEGDASSASYFLAGAAITGGTVTVEGCGTASLQGDVKFAEVLEMMGAKV
            301                                              350
WheatWT (301) TWTDTSVTVTGPPRQPFGRKHLKAVDVNMNKMPDVAMTLAVVALFADGPT
WheatH6 (301) TWTSTSVTVTGPPRQPFGRKHLKAVDVNMNKMPDVAMTLAVVALFADGPT
            351                                              400
WheatWT (351) AIRDVASWRVKETERMVAIRTELTKLGATVEEGPDYCIITPPEKLNITAI
WheatH6 (351) AIRDVASWRVKESERMVAIRTELTKLGATVEEGPDYCIITPPGKLNITAI
            401                                        447
WheatWT (401) DTYDDHRMAMAFSLAACAEVPVTIRDPGCTRKTFPNYFDVLSTFVKN
WheatH6 (401) DTYGDHRMAMAFSLAACGEVPVTIRDPGCTRKTFPNYFDRLSQFVKN
```

FIG. 6

```
                      1                                                50
B. rapaWT    (1)  A KASEIVLQPIREISGLIKLPGSKSLSNRILLLAALSEGTTVVDNLLNS
B. rapaH6    (1)  A RKWSEIVLQPIREISGLIKLPGSKSLSNRILLLAALSEGTTVVDNLLNS
                     51                                               100
B. rapaWT   (51)  DDINYMLDALKKLGLNVERDRVNNRAVVEGCGGIFPASLDSKSDIELYLG
B. rapaH6   (51)  DDINYMLDALKKLGLNVERDRQNNRAVVEGCGGRFPASLDSKSDIELYCG
                    101                                               150
B. rapaWT  (101)  NAGTAMRPLTAAVTAAGGNASYVLDGVPRMRERPIGDLVVGLKQLGADVE
B. rapaH6  (101)  NAATAMRPLTAAVTAAGGNASYVLDGVPRMRERPIGDLVVGLKQLGADVE
                    151                                               200
B. rapaWT  (151)  CTLGTNCPPVRVNANGGLPGGKVKLSGSISSQYLSALLMAAPLALGDVEI
B. rapaH6  (151)  CTLGTNCPPVRVNANGGLPGGKVKLSGSISSQYLSALLMAAPLALGDVEI
                    201                                               250
B. rapaWT  (201)  EIIDKLISVPYVEMTLKLMERFGVSAEHSDSWDRFFVKGGQKYKSPGNAY
B. rapaH6  (201)  EIIDKLISLPYVEMTLKLMERFGVSAEHSDSWDRFFVKGGQKYKSPGNAY
                    251                                               300
B. rapaWT  (251)  VEGDASSASYFLAGAAITGETVTVEGCGTTSLQGDVKFAEVLEKMGCKVS
B. rapaH6  (251)  VEGDASSASYFLAGAAITGETVTVEGCGTASLQGDVKFAEVLEKMGCKVS
                    301                                               350
B. rapaWT  (301)  WTENSVTVTGPSRDAFGMRHLGAVDVNMDKMPDVAMTLAVVALFADGPTT
B. rapaH6  (301)  WTSNSVTVTGPSRDAFGMRHLGAVDVNMDKMPDVAMTLAVVALFADGPTT
                    351                                               400
B. rapaWT  (351)  LRDVASWRVKETERMIAICTELRKLGATVEEGSDYCVITPPAKVKPAEID
B. rapaH6  (351)  LRDVASWRVKESERMIAICTELRKLGATVEEGSDYCVITPPGKVKPAEID
                    401                                        446
B. rapaWT  (401)  TYDDHRMAMAFSLAACADVPVTIKDPGCTRKTFPDYFQVLESITKH
B. rapaH6  (401)  TYGDHRMAMAFSLAACGDVPVTIKDPGCTRKTFPDYFQVLESITKH
```

FIG. 7

```
                  1                                                50
SorghumC1   (1)   ARGWEEIVLQPIKEISGTVKLPGSKSLSNRILLLAALSEGTTVVDNLLNS
SorghumWT   (1)   AAGAEEIVLQPIKEISGTVKLPGSKSLSNRILLLAALSEGTTVVDNLLNS
                  51                                              100
SorghumC1  (51)   EDVHYMLGALNTLGLSVEADKVAKRAVVVGCGGRFPVEDAKEEVQLFCGN
SorghumWT  (51)   EDVHYMLGALNTLGLSVEADKVAKRAVVVGCGGKFPVEDAKEEVQLFLGN
                  101                                             150
SorghumC1 (101)   AATAMRPLTAAVTAAGGNATYVLDGVPRMRERPIGDLVVGLKQLGADVDC
SorghumWT (101)   AGTAMRPLTAAVTAAGGNATYVLDGVPRMRERPIGDLVVGLKQLGADVDC
                  151                                             200
SorghumC1 (151)   FLGTDCPPVRINGIGGLPGGKVKLSGSISSQYLSALLMAAPLALGDVEIE
SorghumWT (151)   FLGTDCPPVRINGIGGLPGGKVKLSGSISSQYLSALLMAAPLALGDVEIE
                  201                                             250
SorghumC1 (201)   IIDKLISLPYVEMTLRLMERFGVKAEHSDSWDRFYIKGGQKYESPKNAYV
SorghumWT (201)   IIDKLISIPYVEMTLRLMERFGVKAEHSDSWDRFYIKGGQKYKSPKNAYV
                  251                                             300
SorghumC1 (251)   EGDASSASYFLAGAAITGGTVTVEGCGTTSLQGDVKFAEVLEMMGAKVTW
SorghumWT (251)   EGDASSASYFLAGAAITGGTVTVEGCGTTSLQGDVKFAEVLEMMGAKVTW
                  301                                             350
SorghumC1 (301)   TETSVTVTGPPRQPFGRKHLKAIDVNMNKMPDVAMTLAVVALFADGPTAI
SorghumWT (301)   TETSVTVTGPPRQPFGRKHLKAIDVNMNKMPDVAMTLAVVALFADGPTAI
                  351                                             400
SorghumC1 (351)   RDVASWRVKETERMVAIRTELTKLGASVEEGPDYCIITPPEKLNVTAIDT
SorghumWT (351)   RDVASWRVKETERMVAIRTELTKLGASVEEGPDYCIITPPDKLNVTAIDT
                  401                                    445
SorghumC1 (401)   YCDHRMAMAFSLAACAEVPVTIRDPGCTRKTFPDYFDVLSTFVKN
SorghumWT (401)   YDDHRMAMAFSLAACAEVPVTIRDPGCTRKTFPDYFDVLSTFVKN
```

FIG. 8

SEQUENCE LISTING

<160> NUMBER OF SEQ ID NOS: 34

<210> SEQ ID NO 1
<211> LENGTH: 445
<212> TYPE: PRT
<213> ORGANISM: Zea mays

<400> SEQUENCE: 1

Met Ala Gly Ala Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Glu Asp Val His Tyr Met Leu Gly Ala Leu Arg Thr Leu Gly
    50                  55                  60

Leu Ser Val Glu Ala Asp Lys Ala Ala Lys Arg Ala Val Val Val Gly
65                  70                  75                  80

Cys Gly Gly Lys Phe Pro Val Glu Asp Ala Lys Glu Glu Val Gln Leu
                85                  90                  95

Phe Leu Gly Asn Ala Gly Thr Ala Met Arg Pro Leu Thr Ala Ala Val
            100                 105                 110

Thr Ala Ala Gly Gly Asn Ala Thr Tyr Val Leu Asp Gly Val Pro Arg
        115                 120                 125

Met Arg Glu Arg Pro Ile Gly Asp Leu Val Val Gly Leu Lys Gln Leu
    130                 135                 140

Gly Ala Asp Val Asp Cys Phe Leu Gly Thr Asp Cys Pro Pro Val Arg
145                 150                 155                 160

Val Asn Gly Ile Gly Gly Leu Pro Gly Gly Lys Val Lys Leu Ser Gly
                165                 170                 175

Ser Ile Ser Ser Gln Tyr Leu Ser Ala Leu Leu Met Ala Ala Pro Leu
            180                 185                 190

```
Ala Leu Gly Asp Val Glu Ile Glu Ile Ile Asp Lys Leu Ile Ser Ile
            195                 200                 205

Pro Tyr Val Glu Met Thr Leu Arg Leu Met Glu Arg Phe Gly Val Lys
        210                 215                 220

Ala Glu His Ser Asp Ser Trp Asp Arg Phe Tyr Ile Lys Gly Gly Gln
225                 230                 235                 240

Lys Tyr Lys Ser Pro Lys Asn Ala Tyr Val Glu Gly Asp Ala Ser Ser
                245                 250                 255

Ala Ser Tyr Phe Leu Ala Gly Ala Ala Ile Thr Gly Gly Thr Val Thr
            260                 265                 270

Val Glu Gly Cys Gly Thr Thr Ser Leu Gln Gly Asp Val Lys Phe Ala
        275                 280                 285

Glu Val Leu Glu Met Met Gly Ala Lys Val Thr Trp Thr Glu Thr Ser
290                 295                 300

Val Thr Val Thr Gly Pro Pro Arg Glu Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Thr Glu Arg Met Val Ala Ile Arg
        355                 360                 365

Thr Glu Leu Thr Lys Leu Gly Ala Ser Val Glu Glu Gly Pro Asp Tyr
370                 375                 380

Cys Ile Ile Thr Pro Pro Glu Lys Leu Asn Val Thr Ala Ile Asp Thr
385                 390                 395                 400

Tyr Asp Asp His Arg Met Ala Met Ala Phe Ser Leu Ala Ala Cys Ala
                405                 410                 415

Glu Val Pro Val Thr Ile Arg Asp Pro Gly Cys Thr Arg Lys Thr Phe
            420                 425                 430

Pro Asp Tyr Phe Asp Val Leu Ser Thr Phe Val Lys Asn
        435                 440                 445

<210> SEQ ID NO 2
<211> LENGTH: 444
<212> TYPE: PRT
<213> ORGANISM: Zea mays

<400> SEQUENCE: 2

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125
```

```
Arg Glu Arg Pro Ile Gly Asp Leu Val Gly Leu Lys Gln Leu Gly
            130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440

<210> SEQ ID NO 3
<211> LENGTH: 21
<212> TYPE: PRT
<213> ORGANISM: Artificial
<220> FEATURE:
<223> OTHER INFORMATION: N-terminal extension

<400> SEQUENCE: 3

Met Gly His His His His His His His His Ser Ser Gly His
1               5                   10                  15

Ile Glu Gly Arg His
            20

<210> SEQ ID NO 4
```

<211> LENGTH: 445
<212> TYPE: PRT
<213> ORGANISM: Artificial
<220> FEATURE:
<223> OTHER INFORMATION: maize clone 771-C2

<400> SEQUENCE: 4

```
Met Ala Gly Trp Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Glu Asp Val Met Tyr Met Leu Gly Ala Leu Arg Thr Leu Gly
    50                  55                  60

Leu Ser Val Glu Ala Asp Lys Ala Ala Lys Arg Ala Val Val Val Gly
65                  70                  75                  80

Cys Gly Gly Lys Phe Pro Val Glu Asp Ala Lys Glu Glu Val Gln Leu
                85                  90                  95

Phe Cys Gly Asn Ala Ala Thr Ala Met Arg Pro Leu Thr Ala Ala Val
            100                 105                 110

Thr Ala Ala Gly Gly Asn Ala Thr Tyr Val Leu Asp Gly Val Pro Arg
        115                 120                 125

Met Arg Glu Arg Pro Ile Gly Asp Leu Val Val Gly Leu Lys Gln Leu
    130                 135                 140

Gly Ala Asp Val Asp Cys Phe Leu Gly Thr Asp Cys Pro Pro Val Arg
145                 150                 155                 160

Val Asn Gly Ile Gly Gly Leu Pro Gly Gly Lys Val Arg Leu Ser Gly
                165                 170                 175

Ser Ile Ser Ser Gln Tyr Leu Ser Ala Leu Leu Met Ala Ala Pro Leu
            180                 185                 190

Ala Leu Gly Asp Val Glu Ile Glu Ile Ile Asp Lys Leu Ile Ser Leu
        195                 200                 205

Pro Tyr Val Glu Met Thr Leu Arg Leu Met Glu Arg Phe Gly Val Lys
    210                 215                 220

Ala Glu His Ser Asp Ser Trp Asp Arg Phe Tyr Ile Lys Gly Gly Gln
225                 230                 235                 240

Lys Tyr Glu Ser Pro Lys Asn Ala Tyr Val Glu Gly Asp Ala Ser Ser
                245                 250                 255

Ala Ser Tyr Phe Leu Ala Gly Ala Ala Ile Thr Gly Gly Thr Val Thr
            260                 265                 270

Val Glu Gly Cys Gly Thr Thr Ser Leu Gln Gly Asp Val Lys Phe Ala
        275                 280                 285

Glu Val Leu Glu Met Met Gly Ala Lys Val Thr Trp Thr Ser Thr Ser
    290                 295                 300

Val Thr Val Thr Gly Pro Pro Arg Glu Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Ser Glu Arg Met Val Ala Ile Arg
        355                 360                 365

Thr Glu Leu Thr Lys Leu Gly Ala Ser Val Glu Glu Gly Pro Asp Tyr
    370                 375                 380
```

```
Cys Ile Ile Thr Pro Pro Lys Leu Asn Val Thr Ala Ile Asp Thr
385                 390                 395                 400

Tyr Gly Asp His Arg Met Ala Met Ala Phe Ser Leu Ala Ala Cys Gly
                405                 410                 415

Glu Val Pro Val Thr Ile Arg Asp Pro Gly Cys Thr Arg Lys Thr Phe
            420                 425                 430

Pro Asp Tyr Phe Asp Arg Leu Arg Gln Val Val Lys Asn
        435                 440                 445

<210> SEQ ID NO 5
<211> LENGTH: 445
<212> TYPE: PRT
<213> ORGANISM: Artificial
<220> FEATURE:
<223> OTHER INFORMATION: maize clone 868-H6

<400> SEQUENCE: 5

Met Arg Gly Trp Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
            35                  40                  45

Asn Ser Glu Asp Val His Tyr Met Leu Gly Ala Leu Arg Thr Leu Gly
        50                  55                  60

Leu Ser Val Glu Ala Asp Lys Gln Ala Lys Arg Ala Val Val Val Gly
65                  70                  75                  80

Cys Gly Gly Arg Phe Pro Val Glu Asp Ala Lys Glu Glu Val Gln Leu
                85                  90                  95

Phe Cys Gly Asn Ala Ala Thr Ala Met Arg Pro Leu Thr Ala Ala Val
                100                 105                 110

Thr Ala Ala Gly Gly Asn Ala Thr Tyr Val Leu Asp Gly Val Pro Arg
            115                 120                 125

Met Arg Glu Arg Pro Ile Gly Asp Leu Val Val Gly Leu Lys Gln Leu
            130                 135                 140

Gly Ala Asp Val Asp Cys Phe Leu Gly Thr Asp Cys Pro Pro Val Arg
145                 150                 155                 160

Val Asn Gly Ile Gly Gly Leu Pro Gly Gly Lys Val Lys Leu Ser Gly
                165                 170                 175

Ser Ile Ser Ser Gln Tyr Leu Ser Ala Leu Leu Met Ala Ala Pro Leu
                180                 185                 190

Ala Leu Gly Asp Val Glu Ile Glu Ile Ile Asp Lys Leu Ile Ser Leu
            195                 200                 205

Pro Tyr Val Glu Met Thr Leu Arg Leu Met Glu Arg Phe Gly Val Lys
            210                 215                 220

Ala Glu His Ser Asp Ser Trp Asp Arg Phe Tyr Ile Lys Gly Gly Gln
225                 230                 235                 240

Lys Tyr Lys Ser Pro Lys Asn Ala Tyr Val Glu Gly Asp Ala Ser Ser
                245                 250                 255

Ala Ser Tyr Phe Leu Ala Gly Ala Ala Ile Thr Gly Gly Thr Val Thr
                260                 265                 270

Val Glu Gly Cys Gly Thr Ala Ser Leu Gln Gly Asp Val Lys Phe Ala
            275                 280                 285

Glu Val Leu Glu Met Met Gly Ala Lys Val Thr Trp Ser Thr Ser
            290                 295                 300
```

-continued

```
Val Thr Val Thr Gly Pro Pro Arg Glu Pro Phe Gly Arg Lys His Leu
305                 310                 315                 320

Lys Ala Ile Asp Val Asn Met Asn Lys Met Pro Asp Val Ala Met Thr
            325                 330                 335

Leu Ala Val Ala Leu Phe Ala Asp Gly Pro Thr Ala Ile Arg Asp
        340                 345                 350

Val Ala Ser Trp Arg Val Lys Glu Ser Glu Arg Met Val Ala Ile Arg
        355                 360                 365

Thr Glu Leu Thr Lys Leu Gly Ala Ser Val Glu Gly Pro Asp Tyr
    370                 375                 380

Cys Ile Ile Thr Pro Pro Gly Lys Leu Asn Val Thr Ala Ile Asp Thr
385                 390                 395                 400

Tyr Gly Asp His Arg Met Ala Met Ala Phe Ser Leu Ala Cys Gly
                405                 410                 415

Glu Val Pro Val Thr Ile Arg Asp Pro Gly Cys Thr Arg Lys Thr Phe
                420                 425                 430

Pro Asp Tyr Phe Asp Arg Leu Ser Gln Phe Val Lys Asn
            435                 440                 445
```

<210> SEQ ID NO 6
<211> LENGTH: 445
<212> TYPE: PRT
<213> ORGANISM: Artificial
<220> FEATURE:
<223> OTHER INFORMATION: maize clone 123-C1

<400> SEQUENCE: 6

```
Met Arg Gly Trp Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Glu Asp Val His Tyr Met Leu Gly Ala Leu Arg Thr Leu Gly
    50                  55                  60

Leu Ser Val Glu Ala Asp Lys Ala Ala Lys Arg Ala Val Val Val Gly
65                  70                  75                  80

Cys Gly Gly Arg Phe Pro Val Glu Asp Ala Lys Glu Glu Val Gln Leu
                85                  90                  95

Phe Cys Gly Asn Ala Ala Thr Ala Met Arg Pro Leu Thr Ala Ala Val
            100                 105                 110

Thr Ala Ala Gly Gly Asn Ala Thr Tyr Val Leu Asp Gly Val Pro Arg
        115                 120                 125

Met Arg Glu Arg Pro Ile Gly Asp Leu Val Val Gly Leu Lys Gln Leu
    130                 135                 140

Gly Ala Asp Val Asp Cys Phe Leu Gly Thr Asp Cys Pro Pro Val Arg
145                 150                 155                 160

Val Asn Gly Ile Gly Gly Leu Pro Gly Gly Lys Val Lys Leu Ser Gly
                165                 170                 175

Ser Ile Ser Ser Gln Tyr Leu Ser Ala Leu Leu Met Ala Ala Pro Leu
            180                 185                 190

Ala Leu Gly Asp Val Glu Ile Glu Ile Ile Asp Lys Leu Ile Ser Leu
        195                 200                 205

Pro Tyr Val Glu Met Thr Leu Arg Leu Met Glu Arg Phe Gly Val Lys
    210                 215                 220
```

Ala Glu His Ser Asp Ser Trp Asp Arg Phe Tyr Ile Lys Gly Gly Gln
225                 230                 235                 240

Lys Tyr Glu Ser Pro Lys Asn Ala Tyr Val Glu Gly Asp Ala Ser Ser
            245                 250                 255

Ala Ser Tyr Phe Leu Ala Gly Ala Ala Ile Thr Gly Gly Thr Val Thr
        260                 265                 270

Val Glu Gly Cys Gly Thr Thr Ser Leu Gln Gly Asp Val Lys Phe Ala
    275                 280                 285

Glu Val Leu Glu Met Met Gly Ala Lys Val Thr Trp Thr Glu Thr Ser
290                 295                 300

Val Thr Val Thr Gly Pro Pro Arg Glu Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Thr Glu Arg Met Val Ala Ile Arg
        355                 360                 365

Thr Glu Leu Thr Lys Leu Gly Ala Ser Val Glu Glu Gly Pro Asp Tyr
    370                 375                 380

Cys Ile Ile Thr Pro Pro Lys Leu Asn Val Thr Ala Ile Asp Thr
385                 390                 395                 400

Tyr Gly Asp His Arg Met Ala Met Ala Phe Ser Leu Ala Ala Cys Ala
                405                 410                 415

Glu Val Pro Val Thr Ile Arg Asp Pro Gly Cys Thr Arg Lys Thr Phe
            420                 425                 430

Pro Asp Tyr Phe Asp Val Leu Ser Thr Phe Val Lys Asn
        435                 440                 445

<210> SEQ ID NO 7
<211> LENGTH: 448
<212> TYPE: PRT
<213> ORGANISM: Oryza sativa

<400> SEQUENCE: 7

Ala Pro Ala Ala Lys Ala Glu Glu Ile Val Leu Gln Pro Ile Arg Glu
1               5                   10                  15

Ile Ser Gly Ala Val Gln Leu Pro Gly Ser Lys Ser Leu Ser Asn Arg
            20                  25                  30

Ile Leu Leu Leu Ser Ala Leu Ser Glu Gly Thr Thr Val Val Asp Asn
        35                  40                  45

Leu Leu Asn Ser Glu Asp Val His Tyr Met Leu Glu Ala Leu Lys Ala
    50                  55                  60

Leu Gly Leu Ser Val Glu Ala Asp Lys Val Ala Lys Arg Ala Val Val
65                  70                  75                  80

Val Gly Cys Gly Gly Lys Phe Pro Val Glu Lys Asp Ala Lys Glu Glu
                85                  90                  95

Val Gln Leu Phe Leu Gly Asn Ala Gly Thr Ala Met Arg Pro Leu Thr
            100                 105                 110

Ala Ala Val Thr Ala Ala Gly Gly Asn Ala Thr Tyr Val Leu Asp Gly
        115                 120                 125

Val Pro Arg Met Arg Glu Arg Pro Ile Gly Asp Leu Val Val Gly Leu
    130                 135                 140

Lys Gln Leu Gly Ala Asp Val Asp Cys Phe Leu Gly Thr Glu Cys Pro

```
145                 150                 155                 160
Pro Val Arg Val Lys Gly Ile Gly Gly Leu Pro Gly Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Asp Lys Leu
        195                 200                 205

Ile Ser Ile Pro Tyr Val Glu Met Thr Leu Arg Leu Met Glu Arg Phe
    210                 215                 220

Gly Val Lys Ala Glu His Ser Asp Ser Trp Asp Arg Phe Tyr Ile Lys
225                 230                 235                 240

Gly Gly Gln Lys Tyr Lys Ser Pro Gly Asn Ala Tyr Val Glu Gly Asp
                245                 250                 255

Ala Ser Ser Ala Ser Tyr Phe Leu Ala Gly Ala Ala Ile Thr Gly Gly
            260                 265                 270

Thr Val Thr Val Gln Gly Cys Gly Thr Thr Ser Leu Gln Gly Asp Val
        275                 280                 285

Lys Phe Ala Glu Val Leu Glu Met Met Gly Ala Lys Val Thr Trp Thr
    290                 295                 300

Asp Thr Ser Val Thr Val Thr Gly Pro Pro Arg Glu Pro Tyr Gly Lys
305                 310                 315                 320

Lys His Leu Lys Ala Val Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Thr Glu Arg Met Val
        355                 360                 365

Ala Ile Arg Thr Glu Leu Thr Lys Leu Gly Ala Ser Val Glu Glu Gly
    370                 375                 380

Pro Asp Tyr Cys Ile Ile Thr Pro Pro Glu Lys Leu Asn Ile Thr Ala
385                 390                 395                 400

Ile Asp Thr Tyr Asp Asp His Arg Met Ala Met Ala Phe Ser Leu Ala
                405                 410                 415

Ala Cys Ala Asp Val Pro Val Thr Ile Arg Asp Pro Gly Cys Thr Arg
            420                 425                 430

Lys Thr Phe Pro Asn Tyr Phe Asp Val Leu Ser Thr Phe Val Arg Asn
        435                 440                 445

<210> SEQ ID NO 8
<211> LENGTH: 445
<212> TYPE: PRT
<213> ORGANISM: Sorghum halapense

<400> SEQUENCE: 8

Ala Ala Gly Ala Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
                20                  25                  30

Leu Leu Ala Ala Leu Ser Glu Gly Thr Thr Val Val Asp Asn Leu Leu
            35                  40                  45

Asn Ser Glu Asp Val His Tyr Met Leu Gly Ala Leu Asn Thr Leu Gly
        50                  55                  60

Leu Ser Val Glu Ala Asp Lys Val Ala Lys Arg Ala Val Val Val Gly
65                  70                  75                  80
```

```
Cys Gly Gly Lys Phe Pro Val Glu Asp Ala Lys Glu Glu Val Gln Leu
                85                  90                  95

Phe Leu Gly Asn Ala Gly Thr Ala Met Arg Pro Leu Thr Ala Ala Val
            100                 105                 110

Thr Ala Ala Gly Gly Asn Ala Thr Tyr Val Leu Asp Gly Val Pro Arg
        115                 120                 125

Met Arg Glu Arg Pro Ile Gly Asp Leu Val Val Gly Leu Lys Gln Leu
    130                 135                 140

Gly Ala Asp Val Asp Cys Phe Leu Gly Thr Asp Cys Pro Pro Val Arg
145                 150                 155                 160

Ile Asn Gly Ile Gly Gly Leu Pro Gly Gly Lys Val Lys Leu Ser Gly
                165                 170                 175

Ser Ile Ser Ser Gln Tyr Leu Ser Ala Leu Leu Met Ala Ala Pro Leu
            180                 185                 190

Ala Leu Gly Asp Val Glu Ile Glu Ile Ile Asp Lys Leu Ile Ser Ile
        195                 200                 205

Pro Tyr Val Glu Met Thr Leu Arg Leu Met Glu Arg Phe Gly Val Lys
    210                 215                 220

Ala Glu His Ser Asp Ser Trp Asp Arg Phe Tyr Ile Lys Gly Gly Gln
225                 230                 235                 240

Lys Tyr Lys Ser Pro Lys Asn Ala Tyr Val Glu Gly Asp Ala Ser Ser
                245                 250                 255

Ala Ser Tyr Phe Leu Ala Gly Ala Ala Ile Thr Gly Gly Thr Val Thr
            260                 265                 270

Val Glu Gly Cys Gly Thr Thr Ser Leu Gln Gly Asp Val Lys Phe Ala
        275                 280                 285

Glu Val Leu Glu Met Met Gly Ala Lys Val Thr Trp Thr Glu Thr Ser
    290                 295                 300

Val Thr Val Thr Gly Pro Pro Arg Gln Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Thr Glu Arg Met Val Ala Ile Arg
        355                 360                 365

Thr Glu Leu Thr Lys Leu Gly Ala Ser Val Glu Glu Gly Pro Asp Tyr
    370                 375                 380

Cys Ile Ile Thr Pro Pro Glu Lys Leu Asn Val Thr Ala Ile Asp Thr
385                 390                 395                 400

Tyr Asp Asp His Arg Met Ala Met Ala Phe Ser Leu Ala Ala Cys Ala
                405                 410                 415

Glu Val Pro Val Thr Ile Arg Asp Pro Gly Cys Thr Arg Lys Thr Phe
            420                 425                 430

Pro Asp Tyr Phe Asp Val Leu Ser Thr Phe Val Lys Asn
        435                 440                 445

<210> SEQ ID NO 9
<211> LENGTH: 452
<212> TYPE: PRT
<213> ORGANISM: Helianthus sp.

<400> SEQUENCE: 9

Ala Thr Thr Gln Lys Thr Ser Thr Ala Pro Glu Glu Ile Val Leu Lys
1               5                   10                  15
```

-continued

Pro Ile Lys Glu Ile Ser Gly Thr Val Asn Leu Pro Gly Ser Lys Ser
         20                  25                  30

Leu Ser Asn Arg Ile Leu Leu Ala Ala Leu Ala Glu Gly Thr Thr
         35                  40                  45

Val Val Asp Asn Leu Leu Asn Ser Asp Asp Val His Tyr Met Leu Gly
 50                  55                  60

Ala Leu Arg Ala Leu Gly Leu Asn Val Glu Glu Asn Gly Glu Ile Lys
 65                  70                  75                  80

Arg Ala Thr Val Glu Gly Cys Gly Gly Val Phe Pro Val Gly Lys Glu
             85                  90                  95

Ala Lys Asp Glu Ile Gln Leu Phe Leu Gly Asn Ala Gly Thr Ala Met
            100                 105                 110

Arg Pro Leu Thr Ala Ala Val Thr Ala Ala Gly Gly Asn Ser Ser Tyr
            115                 120                 125

Ile Leu Asp Gly Val Pro Arg Met Arg Glu Arg Pro Ile Gly Asp Leu
130                 135                 140

Val Thr Gly Leu Lys Gln Leu Gly Ala Asp Val Asp Cys Phe Leu Gly
145                 150                 155                 160

Thr Asn Cys Pro Pro Val Arg Val Ala Ala Asn Gly Gly Leu Pro Gly
                165                 170                 175

Gly Lys Val Lys Leu Ser Gly Ser Ile Ser Ser Gln Tyr Leu Thr Ala
            180                 185                 190

Leu Leu Met Ala Ala Pro Leu Ala Leu Gly Asp Val Glu Ile Glu Ile
            195                 200                 205

Ile Asp Lys Leu Ile Ser Val Pro Tyr Val Glu Met Thr Leu Lys Leu
210                 215                 220

Met Glu Arg Phe Gly Val Ser Val Glu His Ser Asp Ser Trp Asp Lys
225                 230                 235                 240

Phe Tyr Val Arg Gly Gly Gln Lys Tyr Lys Ser Pro Gly Asn Ala Tyr
                245                 250                 255

Val Glu Gly Asp Ala Ser Ser Ala Ser Tyr Phe Leu Ala Gly Ala Ala
            260                 265                 270

Ile Thr Gly Gly Thr Val Thr Val Glu Gly Cys Gly Thr Ser Ser Leu
            275                 280                 285

Gln Gly Asp Val Lys Phe Ala Glu Val Leu Gly Gln Met Gly Ala Glu
            290                 295                 300

Val Thr Trp Thr Glu Asn Ser Val Thr Val Arg Gly Pro Pro Arg Asn
305                 310                 315                 320

Ala Ser Gly Arg Gly His Leu Arg Pro Val Asp Val Asn Met Asn Lys
                325                 330                 335

Met Pro Asp Val Ala Met Thr Leu Ala Val Val Ala Leu Tyr Ala Asp
            340                 345                 350

Gly Pro Thr Ala Ile Arg Asp Val Ala Ser Trp Arg Val Lys Glu Thr
            355                 360                 365

Glu Arg Met Ile Ala Ile Cys Thr Glu Leu Arg Lys Leu Gly Ala Thr
            370                 375                 380

Val Glu Glu Gly Pro Asp Tyr Cys Val Ile Thr Pro Glu Lys Leu
385                 390                 395                 400

Asn Val Thr Ala Ile Asp Thr Tyr Asp Asp His Arg Met Ala Met Ala
                405                 410                 415

Phe Ser Leu Ala Ala Cys Ala Asp Val Pro Val Thr Ile Lys Asp Pro
            420                 425                 430

Gly Cys Thr Arg Lys Thr Phe Pro Asp Tyr Phe Glu Val Leu Glu Arg
            435                 440                 445

Phe Thr Lys His
        450

<210> SEQ ID NO 10
<211> LENGTH: 452
<212> TYPE: PRT
<213> ORGANISM: Artificial
<220> FEATURE:
<223> OTHER INFORMATION: mutated sunflower H6

<400> SEQUENCE: 10

Ala Thr Thr Arg Lys Trp Ser Thr Ala Pro Glu Glu Ile Val Leu Lys
1               5                   10                  15

Pro Ile Lys Glu Ile Ser Gly Thr Val Asn Leu Pro Gly Ser Lys Ser
            20                  25                  30

Leu Ser Asn Arg Ile Leu Leu Leu Ala Ala Leu Ala Glu Gly Thr Thr
        35                  40                  45

Val Val Asp Asn Leu Leu Asn Ser Asp Asp Val His Tyr Met Leu Gly
    50                  55                  60

Ala Leu Arg Ala Leu Gly Leu Asn Val Glu Glu Asn Gly Gln Ile Lys
65                  70                  75                  80

Arg Ala Thr Val Glu Gly Cys Gly Gly Arg Phe Pro Val Gly Lys Glu
                85                  90                  95

Ala Lys Asp Glu Ile Gln Leu Phe Cys Gly Asn Ala Ala Thr Ala Met
            100                 105                 110

Arg Pro Leu Thr Ala Ala Val Thr Ala Ala Gly Gly Asn Ser Ser Tyr
        115                 120                 125

Ile Leu Asp Gly Val Pro Arg Met Arg Glu Arg Pro Ile Gly Asp Leu
    130                 135                 140

Val Thr Gly Leu Lys Gln Leu Gly Ala Asp Val Asp Cys Phe Leu Gly
145                 150                 155                 160

Thr Asn Cys Pro Pro Val Arg Val Ala Ala Asn Gly Gly Leu Pro Gly
                165                 170                 175

Gly Lys Val Lys Leu Ser Gly Ser Ile Ser Ser Gln Tyr Leu Thr Ala
            180                 185                 190

Leu Leu Met Ala Ala Pro Leu Ala Leu Gly Asp Val Glu Ile Glu Ile
        195                 200                 205

Ile Asp Lys Leu Ile Ser Leu Pro Tyr Val Glu Met Thr Leu Lys Leu
    210                 215                 220

Met Glu Arg Phe Gly Val Ser Val Glu His Ser Asp Ser Trp Asp Lys
225                 230                 235                 240

Phe Tyr Val Arg Gly Gly Gln Lys Tyr Lys Ser Pro Gly Asn Ala Tyr
                245                 250                 255

Val Glu Gly Asp Ala Ser Ser Ala Ser Tyr Phe Leu Ala Gly Ala Ala
            260                 265                 270

Ile Thr Gly Gly Thr Val Thr Val Glu Gly Cys Gly Thr Ala Ser Leu
        275                 280                 285

Gln Gly Asp Val Lys Phe Ala Glu Val Leu Gly Gln Met Gly Ala Glu
    290                 295                 300

Val Thr Trp Thr Ser Asn Ser Val Thr Val Arg Gly Pro Pro Arg Asn
305                 310                 315                 320

Ala Ser Gly Arg Gly His Leu Arg Pro Val Asp Val Asn Met Asn Lys
                325                 330                 335

```
Met Pro Asp Val Ala Met Thr Leu Ala Val Ala Leu Tyr Ala Asp
            340                 345                 350

Gly Pro Thr Ala Ile Arg Asp Val Ala Ser Trp Arg Val Lys Glu Ser
        355                 360                 365

Glu Arg Met Ile Ala Ile Cys Thr Glu Leu Arg Lys Leu Gly Ala Thr
    370                 375                 380

Val Glu Glu Gly Pro Asp Tyr Cys Val Ile Thr Pro Pro Gly Lys Leu
385                 390                 395                 400

Asn Val Thr Ala Ile Asp Thr Tyr Gly Asp His Arg Met Ala Met Ala
                405                 410                 415

Phe Ser Leu Ala Ala Cys Gly Asp Val Pro Val Thr Ile Lys Asp Pro
            420                 425                 430

Gly Cys Thr Arg Lys Thr Phe Pro Asp Tyr Phe Glu Arg Leu Glu Gln
        435                 440                 445

Phe Thr Lys His
            450

<210> SEQ ID NO 11
<211> LENGTH: 448
<212> TYPE: PRT
<213> ORGANISM: Artificial
<220> FEATURE:
<223> OTHER INFORMATION: mutated rice H6

<400> SEQUENCE: 11

Ala Pro Ala Arg Lys Trp Glu Glu Ile Val Leu Gln Pro Ile Arg Glu
1               5                   10                  15

Ile Ser Gly Ala Val Gln Leu Pro Gly Ser Lys Ser Leu Ser Asn Arg
            20                  25                  30

Ile Leu Leu Leu Ser Ala Leu Ser Glu Gly Thr Thr Val Val Asp Asn
        35                  40                  45

Leu Leu Asn Ser Glu Asp Val His Tyr Met Leu Glu Ala Leu Lys Ala
    50                  55                  60

Leu Gly Leu Ser Val Glu Ala Asp Lys Gln Ala Lys Arg Ala Val Val
65                  70                  75                  80

Val Gly Cys Gly Gly Arg Phe Pro Val Glu Lys Asp Ala Lys Glu Glu
                85                  90                  95

Val Gln Leu Phe Cys Gly Asn Ala Ala Thr Ala Met Arg Pro Leu Thr
            100                 105                 110

Ala Ala Val Thr Ala Ala Gly Gly Asn Ala Thr Tyr Val Leu Asp Gly
        115                 120                 125

Val Pro Arg Met Arg Glu Arg Pro Ile Gly Asp Leu Val Val Gly Leu
    130                 135                 140

Lys Gln Leu Gly Ala Asp Val Asp Cys Phe Leu Gly Thr Glu Cys Pro
145                 150                 155                 160

Pro Val Arg Val Lys Gly Ile Gly Gly Leu Pro Gly Gly Lys Val Lys
                165                 170                 175

Leu Ser Gly Ser Ile Ser Ser Gln Tyr Leu Ser Ala Leu Leu Met Ala
            180                 185                 190

Ala Pro Leu Ala Leu Gly Asp Val Glu Ile Glu Ile Asp Lys Leu
        195                 200                 205

Ile Ser Leu Pro Tyr Val Glu Met Thr Leu Arg Leu Met Glu Arg Phe
    210                 215                 220

Gly Val Lys Ala Glu His Ser Asp Ser Trp Asp Arg Phe Tyr Ile Lys
225                 230                 235                 240
```

```
Gly Gly Gln Lys Tyr Lys Ser Pro Gly Asn Ala Tyr Val Glu Gly Asp
            245                 250                 255

Ala Ser Ser Ala Ser Tyr Phe Leu Ala Gly Ala Ile Thr Gly Gly
        260                 265                 270

Thr Val Thr Val Gln Gly Cys Gly Thr Ala Ser Leu Gln Gly Asp Val
            275                 280                 285

Lys Phe Ala Glu Val Leu Glu Met Met Gly Ala Lys Val Thr Trp Thr
290                 295                 300

Ser Thr Ser Val Thr Val Thr Gly Pro Pro Arg Glu Pro Tyr Gly Lys
305                 310                 315                 320

Lys His Leu Lys Ala Val Asp Val Asn Met Asn Lys Met Pro Asp Val
                325                 330                 335

Ala Met Thr Leu Ala Val Val Ala Leu Phe Ala Asp Gly Pro Thr Ala
            340                 345                 350

Ile Arg Asp Val Ala Ser Trp Arg Val Lys Glu Ser Glu Arg Met Val
            355                 360                 365

Ala Ile Arg Thr Glu Leu Thr Lys Leu Gly Ala Ser Val Glu Glu Gly
        370                 375                 380

Pro Asp Tyr Cys Ile Ile Thr Pro Pro Gly Lys Leu Asn Ile Thr Ala
385                 390                 395                 400

Ile Asp Thr Tyr Gly Asp His Arg Met Ala Met Ala Phe Ser Leu Ala
            405                 410                 415

Ala Cys Gly Asp Val Pro Val Thr Ile Arg Asp Pro Gly Cys Thr Arg
            420                 425                 430

Lys Thr Phe Pro Asn Tyr Phe Asp Arg Leu Ser Gln Phe Val Arg Asn
        435                 440                 445

<210> SEQ ID NO 12
<211> LENGTH: 445
<212> TYPE: PRT
<213> ORGANISM: Artificial
<220> FEATURE:
<223> OTHER INFORMATION: mutated sorghum H6

<400> SEQUENCE: 12

Ala Arg Gly Trp Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Glu Asp Val His Tyr Met Leu Gly Ala Leu Asn Thr Leu Gly
    50                  55                  60

Leu Ser Val Glu Ala Asp Lys Gln Ala Lys Arg Ala Val Val Val Gly
65                  70                  75                  80

Cys Gly Gly Arg Phe Pro Val Glu Asp Ala Lys Glu Glu Val Gln Leu
                85                  90                  95

Phe Cys Gly Asn Ala Ala Thr Ala Met Arg Pro Leu Thr Ala Ala Val
            100                 105                 110

Thr Ala Ala Gly Gly Asn Ala Thr Tyr Val Leu Asp Gly Val Pro Arg
        115                 120                 125

Met Arg Glu Arg Pro Ile Gly Asp Leu Val Val Gly Leu Lys Gln Leu
130                 135                 140

Gly Ala Asp Val Asp Cys Phe Leu Gly Thr Asp Cys Pro Pro Val Arg
145                 150                 155                 160
```

Ile Asn Gly Ile Gly Gly Leu Pro Gly Gly Lys Val Lys Leu Ser Gly
            165                 170                 175

Ser Ile Ser Ser Gln Tyr Leu Ser Ala Leu Leu Met Ala Ala Pro Leu
        180                 185                 190

Ala Leu Gly Asp Val Glu Ile Glu Ile Asp Lys Leu Ile Ser Leu
        195                 200                 205

Pro Tyr Val Glu Met Thr Leu Arg Leu Met Glu Arg Phe Gly Val Lys
    210                 215                 220

Ala Glu His Ser Asp Ser Trp Asp Arg Phe Tyr Ile Lys Gly Gly Gln
225                 230                 235                 240

Lys Tyr Lys Ser Pro Lys Asn Ala Tyr Val Glu Gly Asp Ala Ser Ser
                245                 250                 255

Ala Ser Tyr Phe Leu Ala Gly Ala Ala Ile Thr Gly Gly Thr Val Thr
            260                 265                 270

Val Glu Gly Cys Gly Thr Ala Ser Leu Gln Gly Asp Val Lys Phe Ala
        275                 280                 285

Glu Val Leu Glu Met Met Gly Ala Lys Val Thr Trp Thr Ser Thr Ser
    290                 295                 300

Val Thr Val Thr Gly Pro Pro Arg Gln Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Ser Glu Arg Met Val Ala Ile Arg
        355                 360                 365

Thr Glu Leu Thr Lys Leu Gly Ala Ser Val Glu Glu Gly Pro Asp Tyr
    370                 375                 380

Cys Ile Ile Thr Pro Pro Gly Lys Leu Asn Val Thr Ala Ile Asp Thr
385                 390                 395                 400

Tyr Gly Asp His Arg Met Ala Met Ala Phe Ser Leu Ala Ala Cys Gly
                405                 410                 415

Glu Val Pro Val Thr Ile Arg Asp Pro Gly Cys Thr Arg Lys Thr Phe
            420                 425                 430

Pro Asp Tyr Phe Asp Arg Leu Ser Gln Phe Val Lys Asn
        435                 440                 445

<210> SEQ ID NO 13
<211> LENGTH: 451
<212> TYPE: PRT
<213> ORGANISM: Glycine max

<400> SEQUENCE: 13

Ala Ala Ala Glu Lys Pro Ser Thr Ser Pro Glu Ile Val Leu Glu Pro
1               5                   10                  15

Ile Lys Asp Phe Ser Gly Thr Ile Thr Leu Pro Gly Ser Lys Ser Leu
                20                  25                  30

Ser Asn Arg Ile Leu Leu Leu Ala Ala Leu Ser Glu Gly Thr Thr Val
            35                  40                  45

Val Asp Asn Leu Leu Tyr Ser Glu Asp Ile His Tyr Met Leu Gly Ala
        50                  55                  60

Leu Arg Thr Leu Gly Leu Arg Val Glu Asp Asp Lys Thr Thr Lys Gln
65                  70                  75                  80

Ala Ile Val Glu Gly Cys Gly Gly Leu Phe Pro Thr Ser Lys Glu Ser
                85                  90                  95

```
Lys Asp Glu Ile Asn Leu Phe Leu Gly Asn Ala Gly Thr Ala Met Arg
            100                 105                 110

Pro Leu Thr Ala Ala Val Val Ala Gly Gly Asn Ala Ser Tyr Val
        115                 120                 125

Leu Asp Gly Val Pro Arg Met Arg Glu Arg Pro Ile Gly Asp Leu Val
    130                 135                 140

Ala Gly Leu Lys Gln Leu Gly Ala Asp Val Asp Cys Phe Leu Gly Thr
145                 150                 155                 160

Asn Cys Pro Pro Val Arg Val Asn Gly Lys Gly Leu Pro Gly Gly
                165                 170                 175

Lys Val Lys Leu Ser Gly Ser Val Ser Ser Gln Tyr Leu Thr Ala Leu
            180                 185                 190

Leu Met Ala Ala Pro Leu Ala Leu Gly Asp Val Glu Ile Glu Ile Val
        195                 200                 205

Asp Lys Leu Ile Ser Val Pro Tyr Val Glu Met Thr Leu Lys Leu Met
    210                 215                 220

Glu Arg Phe Gly Val Ser Val Glu His Ser Gly Asn Trp Asp Arg Phe
225                 230                 235                 240

Leu Val His Gly Gly Gln Lys Tyr Lys Ser Pro Gly Asn Ala Phe Val
                245                 250                 255

Glu Gly Asp Ala Ser Ser Ala Ser Tyr Leu Leu Ala Gly Ala Ala Ile
            260                 265                 270

Thr Gly Gly Thr Ile Thr Val Asn Gly Cys Gly Thr Ser Ser Leu Gln
        275                 280                 285

Gly Asp Val Lys Phe Ala Glu Val Leu Glu Lys Met Gly Ala Lys Val
    290                 295                 300

Thr Trp Ser Glu Asn Ser Val Thr Val Ser Gly Pro Pro Arg Asp Phe
305                 310                 315                 320

Ser Gly Arg Lys Val Leu Arg Gly Ile Asp Val Asn Met Asn Lys Met
                325                 330                 335

Pro Asp Val Ala Met Thr Leu Ala Val Val Ala Leu Phe Ala Asn Gly
            340                 345                 350

Pro Thr Ala Ile Arg Asp Val Ala Ser Trp Arg Val Lys Glu Thr Glu
        355                 360                 365

Arg Met Ile Ala Ile Cys Thr Glu Leu Arg Lys Leu Gly Ala Thr Val
    370                 375                 380

Glu Glu Gly Pro Asp Tyr Cys Val Ile Thr Pro Pro Glu Lys Leu Asn
385                 390                 395                 400

Val Thr Ala Ile Asp Thr Tyr Asp Asp His Arg Met Ala Met Ala Phe
                405                 410                 415

Ser Leu Ala Ala Cys Gly Asp Val Pro Val Thr Ile Lys Asp Pro Gly
            420                 425                 430

Cys Thr Arg Lys Thr Phe Pro Asp Tyr Phe Glu Val Leu Glu Arg Leu
        435                 440                 445

Thr Lys His
    450

<210> SEQ ID NO 14
<211> LENGTH: 447
<212> TYPE: PRT
<213> ORGANISM: Triticum aestivum

<400> SEQUENCE: 14

Ala Pro Ser Gly Ala Glu Glu Val Val Leu Gln Pro Ile Arg Glu Ile
```

```
1               5                   10                  15
Ser Gly Ala Val Gln Leu Pro Gly Ser Lys Ser Leu Ser Asn Arg Ile
                20                  25                  30

Leu Leu Leu Ser Ala Leu Ser Glu Gly Thr Thr Val Val Asp Asn Leu
                35                  40                  45

Leu Asn Ser Glu Asp Val His Tyr Met Leu Glu Ala Leu Glu Ala Leu
 50                      55                  60

Gly Leu Ser Val Glu Ala Asp Lys Val Ala Lys Arg Ala Val Val Val
 65                  70                  75                  80

Gly Cys Gly Gly Arg Phe Pro Val Glu Lys Asp Ala Gln Glu Glu Val
                    85                  90                  95

Lys Leu Phe Leu Gly Asn Ala Gly Thr Ala Met Arg Pro Leu Thr Ala
                100                 105                 110

Ala Val Val Ala Ala Gly Gly Asn Ala Thr Tyr Val Leu Asp Gly Val
                115                 120                 125

Pro Arg Met Arg Glu Arg Pro Ile Gly Asp Leu Val Val Gly Leu Gln
                130                 135                 140

Gln Leu Gly Ala Asp Ala Asp Cys Phe Leu Gly Thr Asn Cys Pro Pro
145                 150                 155                 160

Val Arg Ile Asn Gly Lys Gly Leu Pro Gly Gly Lys Val Lys Leu
                    165                 170                 175

Ser Gly Ser Ile Ser Ser Gln Tyr Leu Ser Ser Leu Leu Met Ala Ala
                180                 185                 190

Pro Leu Ala Leu Glu Asp Val Glu Ile Glu Ile Ile Asp Lys Leu Ile
                195                 200                 205

Ser Val Pro Tyr Val Glu Met Thr Leu Lys Leu Met Glu Arg Phe Gly
                210                 215                 220

Val Thr Ala Glu His Ser Asp Ser Trp Asp Arg Phe Tyr Ile Lys Gly
225                 230                 235                 240

Gly Gln Lys Tyr Lys Ser Pro Gly Asn Ala Tyr Val Glu Gly Asp Ala
                    245                 250                 255

Ser Ser Ala Ser Tyr Phe Leu Ala Gly Ala Ala Ile Thr Gly Gly Thr
                260                 265                 270

Val Thr Val Glu Gly Cys Gly Thr Thr Ser Leu Gln Gly Asp Val Lys
                275                 280                 285

Phe Ala Glu Val Leu Glu Met Met Gly Ala Lys Val Thr Trp Thr Asp
                290                 295                 300

Thr Ser Val Thr Val Thr Gly Pro Pro Arg Gln Pro Phe Gly Arg Lys
305                 310                 315                 320

His Leu Lys Ala Val Asp Val Asn Met Asn Lys Met Pro Asp Val Ala
                    325                 330                 335

Met Thr Leu Ala Val Val Ala Leu Phe Ala Asp Gly Pro Thr Ala Ile
                340                 345                 350

Arg Asp Val Ala Ser Trp Arg Val Lys Glu Thr Glu Arg Met Val Ala
                355                 360                 365

Ile Arg Thr Glu Leu Thr Lys Leu Gly Ala Thr Val Glu Glu Gly Pro
                370                 375                 380

Asp Tyr Cys Ile Ile Thr Pro Pro Glu Lys Leu Asn Ile Thr Ala Ile
385                 390                 395                 400

Asp Thr Tyr Asp Asp His Arg Met Ala Met Ala Phe Ser Leu Ala Ala
                    405                 410                 415

Cys Ala Glu Val Pro Val Thr Ile Arg Asp Pro Gly Cys Thr Arg Lys
                420                 425                 430
```

-continued

Thr Phe Pro Asn Tyr Phe Asp Val Leu Ser Thr Phe Val Lys Asn
            435                 440                 445

<210> SEQ ID NO 15
<211> LENGTH: 446
<212> TYPE: PRT
<213> ORGANISM: Brassica rapa

<400> SEQUENCE: 15

Ala Glu Lys Ala Ser Glu Ile Val Leu Gln Pro Ile Arg Glu Ile Ser
1               5                   10                  15

Gly Leu Ile Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Asp Asp Ile Asn Tyr Met Leu Asp Ala Leu Lys Lys Leu Gly
    50                  55                  60

Leu Asn Val Glu Arg Asp Arg Val Asn Asn Arg Ala Val Val Glu Gly
65                  70                  75                  80

Cys Gly Gly Ile Phe Pro Ala Ser Leu Asp Ser Lys Ser Asp Ile Glu
                85                  90                  95

Leu Tyr Leu Gly Asn Ala Gly Thr Ala Met Arg Pro Leu Thr Ala Ala
            100                 105                 110

Val Thr Ala Ala Gly Gly Asn Ala Ser Tyr Val Leu Asp Gly Val Pro
        115                 120                 125

Arg Met Arg Glu Arg Pro Ile Gly Asp Leu Val Val Gly Leu Lys Gln
130                 135                 140

Leu Gly Ala Asp Val Glu Cys Thr Leu Gly Thr Asn Cys Pro Pro Val
145                 150                 155                 160

Arg Val Asn Ala Asn Gly Gly Leu Pro Gly Gly Lys Val Lys Leu Ser
                165                 170                 175

Gly Ser Ile Ser Ser Gln Tyr Leu Ser Ala Leu Leu Met Ala Ala Pro
            180                 185                 190

Leu Ala Leu Gly Asp Val Glu Ile Glu Ile Ile Asp Lys Leu Ile Ser
        195                 200                 205

Val Pro Tyr Val Glu Met Thr Leu Lys Leu Met Glu Arg Phe Gly Val
    210                 215                 220

Ser Ala Glu His Ser Asp Ser Trp Asp Arg Phe Phe Val Lys Gly Gly
225                 230                 235                 240

Gln Lys Tyr Lys Ser Pro Gly Asn Ala Tyr Val Glu Gly Asp Ala Ser
                245                 250                 255

Ser Ala Ser Tyr Phe Leu Ala Gly Ala Ala Ile Thr Gly Glu Thr Val
            260                 265                 270

Thr Val Glu Gly Cys Gly Thr Thr Ser Leu Gln Gly Asp Val Lys Phe
        275                 280                 285

Ala Glu Val Leu Glu Lys Met Gly Cys Lys Val Ser Trp Thr Glu Asn
    290                 295                 300

Ser Val Thr Val Thr Gly Pro Ser Arg Asp Ala Phe Gly Met Arg His
305                 310                 315                 320

Leu Gly Ala Val Asp Val Asn Met Asp Lys Met Pro Asp Val Ala Met
                325                 330                 335

Thr Leu Ala Val Val Ala Leu Phe Ala Asp Gly Pro Thr Thr Leu Arg
            340                 345                 350

Asp Val Ala Ser Trp Arg Val Lys Glu Thr Glu Arg Met Ile Ala Ile

```
                    355                 360                 365
Cys Thr Glu Leu Arg Lys Leu Gly Ala Thr Val Glu Glu Gly Ser Asp
        370                 375                 380

Tyr Cys Val Ile Thr Pro Ala Lys Val Lys Pro Ala Glu Ile Asp
385                 390                 395                 400

Thr Tyr Asp Asp His Arg Met Ala Met Ala Phe Ser Leu Ala Ala Cys
                    405                 410                 415

Ala Asp Val Pro Val Thr Ile Lys Asp Pro Gly Cys Thr Arg Lys Thr
                420                 425                 430

Phe Pro Asp Tyr Phe Gln Val Leu Glu Ser Ile Thr Lys His
            435                 440                 445

<210> SEQ ID NO 16
<211> LENGTH: 448
<212> TYPE: PRT
<213> ORGANISM: Solanum lycopersicum

<400> SEQUENCE: 16

Ala Thr Ala Glu Lys Pro His Glu Ile Val Leu Glu Pro Ile Lys Asp
1               5                   10                  15

Ile Ser Gly Thr Val Lys Leu Pro Gly Ser Lys Ser Leu Ser Asn Arg
            20                  25                  30

Ile Leu Leu Leu Ala Ala Leu Ser Glu Gly Arg Thr Val Val Asp Asn
        35                  40                  45

Leu Leu Ser Ser Asp Asp Ile His Tyr Met Leu Gly Ala Leu Lys Thr
    50                  55                  60

Leu Gly Leu His Val Glu Asp Asp Asn Glu Asn Gln Arg Ala Ile Val
65                  70                  75                  80

Glu Gly Cys Gly Gly Gln Phe Pro Val Gly Lys Lys Ser Glu Glu Glu
                85                  90                  95

Ile Gln Leu Phe Leu Gly Asn Ala Gly Thr Ala Met Arg Pro Leu Thr
            100                 105                 110

Ala Ala Val Thr Val Ala Gly Gly His Ser Arg Tyr Val Leu Asp Gly
        115                 120                 125

Val Pro Arg Met Arg Glu Arg Pro Ile Gly Asp Leu Val Asp Gly Leu
    130                 135                 140

Lys Gln Leu Gly Ala Glu Val Asp Cys Ser Leu Gly Thr Asn Cys Pro
145                 150                 155                 160

Pro Val Arg Ile Val Ser Lys Gly Gly Leu Pro Gly Gly Lys Val Lys
                165                 170                 175

Leu Ser Gly Ser Ile Ser Ser Gln Tyr Leu Thr Ala Leu Leu Met Ala
            180                 185                 190

Ala Pro Leu Ala Leu Gly Asp Val Glu Ile Glu Ile Ile Asp Lys Leu
        195                 200                 205

Ile Ser Val Pro Tyr Val Glu Met Thr Leu Lys Leu Met Glu Arg Phe
    210                 215                 220

Gly Val Phe Val Glu His Ser Ser Gly Trp Asp Arg Phe Leu Val Lys
225                 230                 235                 240

Gly Gly Gln Lys Tyr Lys Ser Pro Gly Lys Ala Phe Val Glu Gly Asp
                245                 250                 255

Ala Ser Ser Ala Ser Tyr Phe Leu Ala Gly Ala Ala Val Thr Gly Gly
            260                 265                 270

Thr Val Thr Val Glu Gly Cys Gly Thr Ser Ser Leu Gln Gly Asp Val
        275                 280                 285
```

```
Lys Phe Ala Glu Val Leu Glu Lys Met Gly Ala Glu Val Thr Trp Thr
    290                 295                 300

Glu Asn Ser Val Thr Val Lys Gly Pro Pro Arg Asn Ser Ser Gly Met
305                 310                 315                 320

Lys His Leu Arg Ala Ile Asp Val Asn Met Asn Lys Met Pro Asp Val
                325                 330                 335

Ala Met Thr Leu Ala Val Val Ala Leu Phe Ala Asp Gly Pro Thr Thr
            340                 345                 350

Ile Arg Asp Val Ala Ser Trp Arg Val Lys Thr Glu Arg Met Ile
        355                 360                 365

Ala Ile Cys Thr Glu Leu Arg Lys Leu Gly Ala Thr Val Val Glu Gly
    370                 375                 380

Ser Asp Tyr Cys Ile Ile Thr Pro Pro Glu Lys Leu Asn Val Thr Glu
385                 390                 395                 400

Ile Asp Thr Tyr Asp Asp His Arg Met Ala Met Ala Phe Ser Leu Ala
                405                 410                 415

Ala Cys Ala Asp Val Pro Val Thr Ile Lys Asp Pro Gly Cys Thr Arg
            420                 425                 430

Lys Thr Phe Pro Asp Tyr Phe Glu Val Leu Gln Lys Tyr Ser Lys His
        435                 440                 445

<210> SEQ ID NO 17
<211> LENGTH: 448
<212> TYPE: PRT
<213> ORGANISM: Solanum tuberosum

<400> SEQUENCE: 17

Ala Thr Ala Glu Lys Pro His Glu Ile Val Leu Glu Pro Ile Lys Asp
1               5                   10                  15

Ile Ser Gly Thr Val Lys Leu Pro Gly Ser Lys Ser Leu Ser Asn Arg
            20                  25                  30

Ile Leu Leu Leu Ala Ala Leu Ser Glu Gly Arg Thr Val Val Asp Asn
        35                  40                  45

Leu Leu Ser Ser Asp Asp Ile His Tyr Met Leu Gly Ala Leu Lys Thr
50                  55                  60

Leu Gly Leu His Val Glu Asp Asp Asn Glu Asn Gln Arg Ala Ile Val
65                  70                  75                  80

Glu Gly Cys Gly Gly Gln Phe Pro Val Gly Lys Lys Ser Glu Glu Glu
                85                  90                  95

Ile Gln Leu Phe Leu Gly Asn Ala Gly Thr Ala Met Arg Pro Leu Thr
            100                 105                 110

Ala Ala Val Thr Val Ala Gly Gly His Ser Arg Tyr Val Leu Asp Gly
        115                 120                 125

Val Pro Arg Met Arg Glu Arg Pro Ile Gly Asp Leu Val Asp Gly Leu
130                 135                 140

Lys Gln Leu Gly Ala Glu Val Asp Cys Ser Leu Gly Thr Asn Cys Pro
145                 150                 155                 160

Pro Val Arg Ile Val Ser Lys Gly Gly Leu Pro Gly Gly Lys Val Lys
                165                 170                 175

Leu Ser Gly Ser Ile Ser Ser Gln Tyr Leu Thr Ala Leu Leu Met Ala
            180                 185                 190

Ala Pro Leu Ala Leu Gly Asp Val Glu Ile Glu Ile Ile Asp Lys Leu
        195                 200                 205

Ile Ser Val Pro Tyr Val Glu Met Thr Leu Lys Leu Met Glu Arg Phe
210                 215                 220
```

Gly Val Phe Val Glu His Ser Ser Trp Asp Arg Phe Leu Val Lys
225                 230                 235                 240

Gly Gly Gln Lys Tyr Lys Ser Pro Gly Lys Ala Phe Val Glu Gly Asp
            245                 250                 255

Ala Ser Ser Ala Ser Tyr Phe Leu Ala Gly Ala Val Thr Gly Gly
        260                 265                 270

Thr Val Thr Val Glu Gly Cys Gly Thr Ser Ser Leu Gln Gly Asp Val
        275                 280                 285

Lys Phe Ala Glu Val Leu Glu Lys Met Gly Ala Glu Val Thr Trp Thr
        290                 295                 300

Glu Asn Ser Val Thr Val Lys Gly Pro Pro Arg Asn Ser Ser Gly Met
305                 310                 315                 320

Lys His Leu Arg Ala Ile Asp Val Asn Met Asn Lys Met Pro Asp Val
            325                 330                 335

Ala Met Thr Leu Ala Val Val Ala Leu Phe Ala Asp Gly Pro Thr Thr
        340                 345                 350

Ile Arg Asp Val Ala Ser Trp Arg Val Lys Glu Thr Glu Arg Met Ile
        355                 360                 365

Ala Ile Cys Thr Glu Leu Arg Lys Leu Gly Ala Thr Val Val Glu Gly
370                 375                 380

Ser Asp Tyr Cys Ile Ile Thr Pro Pro Glu Lys Leu Asn Val Thr Glu
385                 390                 395                 400

Ile Asp Thr Tyr Asp Asp His Arg Met Ala Met Ala Phe Ser Leu Ala
            405                 410                 415

Ala Cys Ala Asp Val Pro Val Thr Ile Lys Asp Pro Gly Cys Thr Arg
            420                 425                 430

Lys Thr Phe Pro Asp Tyr Phe Glu Val Leu Gln Lys Tyr Ser Lys His
        435                 440                 445

<210> SEQ ID NO 18
<211> LENGTH: 451
<212> TYPE: PRT
<213> ORGANISM: Artificial
<220> FEATURE:
<223> OTHER INFORMATION: mutated soy-H6

<400> SEQUENCE: 18

Ala Ala Ala Arg Lys Trp Ser Thr Ser Pro Glu Ile Val Leu Glu Pro
1               5                   10                  15

Ile Lys Asp Phe Ser Gly Thr Ile Thr Leu Pro Gly Ser Lys Ser Leu
            20                  25                  30

Ser Asn Arg Ile Leu Leu Leu Ala Ala Leu Ser Glu Gly Thr Thr Val
        35                  40                  45

Val Asp Asn Leu Leu Tyr Ser Glu Asp Ile His Tyr Met Leu Gly Ala
    50                  55                  60

Leu Arg Thr Leu Gly Leu Arg Val Glu Asp Asp Lys Gln Thr Lys Gln
65              70                  75                  80

Ala Ile Val Glu Gly Cys Gly Gly Arg Phe Pro Thr Ser Lys Glu Ser
            85                  90                  95

Lys Asp Glu Ile Asn Leu Phe Cys Gly Asn Ala Ala Thr Ala Met Arg
            100                 105                 110

Pro Leu Thr Ala Ala Val Val Ala Ala Gly Gly Asn Ala Ser Tyr Val
        115                 120                 125

Leu Asp Gly Val Pro Arg Met Arg Glu Arg Pro Ile Gly Asp Leu Val
        130                 135                 140

```
Ala Gly Leu Lys Gln Leu Gly Ala Asp Val Asp Cys Phe Leu Gly Thr
145                 150                 155                 160

Asn Cys Pro Pro Val Arg Val Asn Gly Lys Gly Gly Leu Pro Gly Gly
                165                 170                 175

Lys Val Lys Leu Ser Gly Ser Val Ser Ser Gln Tyr Leu Thr Ala Leu
            180                 185                 190

Leu Met Ala Ala Pro Leu Ala Leu Gly Asp Val Glu Ile Glu Ile Val
        195                 200                 205

Asp Lys Leu Ile Ser Leu Pro Tyr Val Glu Met Thr Leu Lys Leu Met
    210                 215                 220

Glu Arg Phe Gly Val Ser Val Glu His Ser Gly Asn Trp Asp Arg Phe
225                 230                 235                 240

Leu Val His Gly Gly Gln Lys Tyr Lys Ser Pro Gly Asn Ala Phe Val
                245                 250                 255

Glu Gly Asp Ala Ser Ser Ala Ser Tyr Leu Leu Ala Gly Ala Ala Ile
            260                 265                 270

Thr Gly Gly Thr Ile Thr Val Asn Gly Cys Gly Thr Ala Ser Leu Gln
        275                 280                 285

Gly Asp Val Lys Phe Ala Glu Val Leu Glu Lys Met Gly Ala Lys Val
    290                 295                 300

Thr Trp Ser Ser Asn Ser Val Thr Val Ser Gly Pro Pro Arg Asp Phe
305                 310                 315                 320

Ser Gly Arg Lys Val Leu Arg Gly Ile Asp Val Asn Met Asn Lys Met
                325                 330                 335

Pro Asp Val Ala Met Thr Leu Ala Val Ala Leu Phe Ala Asn Gly
            340                 345                 350

Pro Thr Ala Ile Arg Asp Val Ala Ser Trp Arg Val Lys Glu Ser Glu
        355                 360                 365

Arg Met Ile Ala Ile Cys Thr Glu Leu Arg Lys Leu Gly Ala Thr Val
    370                 375                 380

Glu Glu Gly Pro Asp Tyr Cys Val Ile Thr Pro Pro Gly Lys Leu Asn
385                 390                 395                 400

Val Thr Ala Ile Asp Thr Tyr Gly Asp His Arg Met Ala Met Ala Phe
                405                 410                 415

Ser Leu Ala Ala Cys Gly Asp Val Pro Val Thr Ile Lys Asp Pro Gly
            420                 425                 430

Cys Thr Arg Lys Thr Phe Pro Asp Tyr Phe Glu Arg Leu Glu Gln Leu
        435                 440                 445

Thr Lys His
    450

<210> SEQ ID NO 19
<211> LENGTH: 447
<212> TYPE: PRT
<213> ORGANISM: Artificial
<220> FEATURE:
<223> OTHER INFORMATION: mutated wheat H6

<400> SEQUENCE: 19

Ala Pro Arg Gly Trp Glu Glu Val Val Leu Gln Pro Ile Arg Glu Ile
1               5                   10                  15

Ser Gly Ala Val Gln Leu Pro Gly Ser Lys Ser Leu Ser Asn Arg Ile
            20                  25                  30

Leu Leu Leu Ser Ala Leu Ser Glu Gly Thr Thr Val Val Asp Asn Leu
        35                  40                  45
```

```
Leu Asn Ser Glu Asp Val His Tyr Met Leu Glu Ala Leu Glu Ala Leu
 50                  55                  60

Gly Leu Ser Val Glu Ala Asp Lys Gln Ala Lys Arg Ala Val Val Val
 65                  70                  75                  80

Gly Cys Gly Gly Arg Phe Pro Val Glu Lys Asp Ala Gln Glu Glu Val
                 85                  90                  95

Lys Leu Phe Cys Gly Asn Ala Ala Thr Ala Met Arg Pro Leu Thr Ala
            100                 105                 110

Ala Val Val Ala Ala Gly Gly Asn Ala Thr Tyr Val Leu Asp Gly Val
        115                 120                 125

Pro Arg Met Arg Glu Arg Pro Ile Gly Asp Leu Val Val Gly Leu Gln
130                 135                 140

Gln Leu Gly Ala Asp Ala Asp Cys Phe Leu Gly Thr Asn Cys Pro Pro
145                 150                 155                 160

Val Arg Ile Asn Gly Lys Gly Gly Leu Pro Gly Gly Lys Val Lys Leu
                165                 170                 175

Ser Gly Ser Ile Ser Ser Gln Tyr Leu Ser Ser Leu Leu Met Ala Ala
            180                 185                 190

Pro Leu Ala Leu Glu Asp Val Glu Ile Glu Ile Asp Lys Leu Ile
        195                 200                 205

Ser Leu Pro Tyr Val Glu Met Thr Leu Lys Leu Met Glu Arg Phe Gly
210                 215                 220

Val Thr Ala Glu His Ser Asp Ser Trp Asp Arg Phe Tyr Ile Lys Gly
225                 230                 235                 240

Gly Gln Lys Tyr Lys Ser Pro Gly Asn Ala Tyr Val Glu Gly Asp Ala
                245                 250                 255

Ser Ser Ala Ser Tyr Phe Leu Ala Gly Ala Ala Ile Thr Gly Gly Thr
            260                 265                 270

Val Thr Val Glu Gly Cys Gly Thr Ala Ser Leu Gln Gly Asp Val Lys
        275                 280                 285

Phe Ala Glu Val Leu Glu Met Met Gly Ala Lys Val Thr Trp Thr Ser
290                 295                 300

Thr Ser Val Thr Val Thr Gly Pro Pro Arg Gln Pro Phe Gly Arg Lys
305                 310                 315                 320

His Leu Lys Ala Val Asp Val Asn Met Asn Lys Met Pro Asp Val Ala
                325                 330                 335

Met Thr Leu Ala Val Val Ala Leu Phe Ala Asp Gly Pro Thr Ala Ile
            340                 345                 350

Arg Asp Val Ala Ser Trp Arg Val Lys Glu Ser Glu Arg Met Val Ala
        355                 360                 365

Ile Arg Thr Glu Leu Thr Lys Leu Gly Ala Thr Val Glu Glu Gly Pro
370                 375                 380

Asp Tyr Cys Ile Ile Thr Pro Pro Gly Lys Leu Asn Ile Thr Ala Ile
385                 390                 395                 400

Asp Thr Tyr Gly Asp His Arg Met Ala Met Ala Phe Ser Leu Ala Ala
                405                 410                 415

Cys Gly Glu Val Pro Val Thr Ile Arg Asp Pro Gly Cys Thr Arg Lys
            420                 425                 430

Thr Phe Pro Asn Tyr Phe Asp Arg Leu Ser Gln Phe Val Lys Asn
        435                 440                 445

<210> SEQ ID NO 20
<211> LENGTH: 446
```

```
<212> TYPE: PRT
<213> ORGANISM: Artificial
<220> FEATURE:
<223> OTHER INFORMATION: mutated Brassica H6

<400> SEQUENCE: 20

Ala Arg Lys Trp Ser Glu Ile Val Leu Gln Pro Ile Arg Glu Ile Ser
1               5                   10                  15

Gly Leu Ile Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Asp Asp Ile Asn Tyr Met Leu Asp Ala Leu Lys Lys Leu Gly
    50                  55                  60

Leu Asn Val Glu Arg Asp Arg Gln Asn Asn Arg Ala Val Val Glu Gly
65                  70                  75                  80

Cys Gly Gly Arg Phe Pro Ala Ser Leu Asp Ser Lys Ser Asp Ile Glu
                85                  90                  95

Leu Tyr Cys Gly Asn Ala Ala Thr Ala Met Arg Pro Leu Thr Ala Ala
            100                 105                 110

Val Thr Ala Ala Gly Gly Asn Ala Ser Tyr Val Leu Asp Gly Val Pro
        115                 120                 125

Arg Met Arg Glu Arg Pro Ile Gly Asp Leu Val Val Gly Leu Lys Gln
130                 135                 140

Leu Gly Ala Asp Val Glu Cys Thr Leu Gly Thr Asn Cys Pro Pro Val
145                 150                 155                 160

Arg Val Asn Ala Asn Gly Gly Leu Pro Gly Gly Lys Val Lys Leu Ser
                165                 170                 175

Gly Ser Ile Ser Ser Gln Tyr Leu Ser Ala Leu Leu Met Ala Ala Pro
            180                 185                 190

Leu Ala Leu Gly Asp Val Glu Ile Glu Ile Asp Lys Leu Ile Ser
        195                 200                 205

Leu Pro Tyr Val Glu Met Thr Leu Lys Leu Met Glu Arg Phe Gly Val
210                 215                 220

Ser Ala Glu His Ser Asp Ser Trp Asp Arg Phe Phe Val Lys Gly Gly
225                 230                 235                 240

Gln Lys Tyr Lys Ser Pro Gly Asn Ala Tyr Val Glu Gly Asp Ala Ser
                245                 250                 255

Ser Ala Ser Tyr Phe Leu Ala Gly Ala Ala Ile Thr Gly Glu Thr Val
            260                 265                 270

Thr Val Glu Gly Cys Gly Thr Ala Ser Leu Gln Gly Asp Val Lys Phe
        275                 280                 285

Ala Glu Val Leu Glu Lys Met Gly Cys Lys Val Ser Trp Thr Ser Asn
290                 295                 300

Ser Val Thr Val Thr Gly Pro Ser Arg Asp Ala Phe Gly Met Arg His
305                 310                 315                 320

Leu Gly Ala Val Asp Val Asn Met Asp Lys Met Pro Asp Val Ala Met
                325                 330                 335

Thr Leu Ala Val Val Ala Leu Phe Ala Asp Gly Pro Thr Thr Leu Arg
            340                 345                 350

Asp Val Ala Ser Trp Arg Val Lys Glu Ser Glu Arg Met Ile Ala Ile
        355                 360                 365

Cys Thr Glu Leu Arg Lys Leu Gly Ala Thr Val Glu Glu Gly Ser Asp
370                 375                 380
```

```
Tyr Cys Val Ile Thr Pro Gly Lys Val Lys Pro Ala Glu Ile Asp
385                 390                 395                 400

Thr Tyr Gly Asp His Arg Met Ala Met Ala Phe Ser Leu Ala Ala Cys
            405                 410                 415

Gly Asp Val Pro Val Thr Ile Lys Asp Pro Gly Cys Thr Arg Lys Thr
            420                 425                 430

Phe Pro Asp Tyr Phe Gln Val Leu Glu Ser Ile Thr Lys His
            435                 440                 445

<210> SEQ ID NO 21
<211> LENGTH: 448
<212> TYPE: PRT
<213> ORGANISM: Artificial
<220> FEATURE:
<223> OTHER INFORMATION: mutated tomato H6

<400> SEQUENCE: 21

Ala Thr Ala Arg Lys Trp His Glu Ile Val Leu Glu Pro Ile Lys Asp
1               5                   10                  15

Ile Ser Gly Thr Val Lys Leu Pro Gly Ser Lys Ser Leu Ser Asn Arg
            20                  25                  30

Ile Leu Leu Leu Ala Ala Leu Ser Glu Gly Arg Thr Val Val Asp Asn
        35                  40                  45

Leu Leu Ser Ser Asp Asp Ile His Tyr Met Leu Gly Ala Leu Lys Thr
50                  55                  60

Leu Gly Leu His Val Glu Asp Asp Asn Gln Asn Gln Arg Ala Ile Val
65                  70                  75                  80

Glu Gly Cys Gly Gly Arg Phe Pro Val Gly Lys Lys Ser Glu Glu Glu
                85                  90                  95

Ile Gln Leu Phe Cys Gly Asn Ala Ala Thr Ala Met Arg Pro Leu Thr
            100                 105                 110

Ala Ala Val Thr Val Ala Gly Gly His Ser Arg Tyr Val Leu Asp Gly
        115                 120                 125

Val Pro Arg Met Arg Glu Arg Pro Ile Gly Asp Leu Val Asp Gly Leu
130                 135                 140

Lys Gln Leu Gly Ala Glu Val Asp Cys Ser Leu Gly Thr Asn Cys Pro
145                 150                 155                 160

Pro Val Arg Ile Val Ser Lys Gly Gly Leu Pro Gly Gly Lys Val Lys
                165                 170                 175

Leu Ser Gly Ser Ile Ser Ser Gln Tyr Leu Thr Ala Leu Leu Met Ala
            180                 185                 190

Ala Pro Leu Ala Leu Gly Asp Val Glu Ile Glu Ile Asp Lys Leu
        195                 200                 205

Ile Ser Leu Pro Tyr Val Glu Met Thr Leu Lys Leu Met Glu Arg Phe
210                 215                 220

Gly Val Phe Val Glu His Ser Ser Gly Trp Asp Arg Phe Leu Val Lys
225                 230                 235                 240

Gly Gly Gln Lys Tyr Lys Ser Pro Gly Lys Ala Phe Val Glu Gly Asp
                245                 250                 255

Ala Ser Ser Ala Ser Tyr Phe Leu Ala Gly Ala Ala Val Thr Gly Gly
            260                 265                 270

Thr Val Thr Val Glu Gly Cys Gly Thr Ala Ser Leu Gln Gly Asp Val
        275                 280                 285

Lys Phe Ala Glu Val Leu Glu Lys Met Gly Ala Glu Val Thr Trp Thr
290                 295                 300
```

```
Ser Asn Ser Val Thr Val Lys Gly Pro Pro Arg Asn Ser Ser Gly Met
305                 310                 315                 320

Lys His Leu Arg Ala Ile Asp Val Asn Met Asn Lys Met Pro Asp Val
            325                 330                 335

Ala Met Thr Leu Ala Val Val Ala Leu Phe Ala Asp Gly Pro Thr Thr
            340                 345                 350

Ile Arg Asp Val Ala Ser Trp Arg Val Lys Glu Ser Glu Arg Met Ile
            355                 360                 365

Ala Ile Cys Thr Glu Leu Arg Lys Leu Gly Ala Thr Val Val Glu Gly
            370                 375                 380

Ser Asp Tyr Cys Ile Ile Thr Pro Pro Gly Lys Leu Asn Val Thr Glu
385                 390                 395                 400

Ile Asp Thr Tyr Gly Asp His Arg Met Ala Met Ala Phe Ser Leu Ala
            405                 410                 415

Ala Cys Gly Asp Val Pro Val Thr Ile Lys Asp Pro Gly Cys Thr Arg
            420                 425                 430

Lys Thr Phe Pro Asp Tyr Phe Glu Arg Leu Gln Gln Tyr Ser Lys His
            435                 440                 445
```

<210> SEQ ID NO 22
<211> LENGTH: 448
<212> TYPE: PRT
<213> ORGANISM: Artificial
<220> FEATURE:
<223> OTHER INFORMATION: mutated potato H6

<400> SEQUENCE: 22

```
Ala Thr Ala Arg Lys Trp His Glu Ile Val Leu Glu Pro Ile Lys Asp
1               5                   10                  15

Ile Ser Gly Thr Val Lys Leu Pro Gly Ser Lys Ser Leu Ser Asn Arg
            20                  25                  30

Ile Leu Leu Leu Ala Ala Leu Ser Glu Gly Arg Thr Val Val Asp Asn
            35                  40                  45

Leu Leu Ser Ser Asp Asp Ile His Tyr Met Leu Gly Ala Leu Lys Thr
50                  55                  60

Leu Gly Leu His Val Glu Asp Asn Gln Asn Gln Arg Ala Ile Val
65                  70                  75                  80

Glu Gly Cys Gly Gly Arg Phe Pro Val Gly Lys Lys Ser Glu Glu
            85                  90                  95

Ile Gln Leu Phe Cys Gly Asn Ala Ala Thr Ala Met Arg Pro Leu Thr
            100                 105                 110

Ala Ala Val Thr Val Ala Gly Gly His Ser Arg Tyr Val Leu Asp Gly
            115                 120                 125

Val Pro Arg Met Arg Glu Arg Pro Ile Gly Asp Leu Val Asp Gly Leu
130                 135                 140

Lys Gln Leu Gly Ala Glu Val Asp Cys Ser Leu Gly Thr Asn Cys Pro
145                 150                 155                 160

Pro Val Arg Ile Val Ser Lys Gly Gly Leu Pro Gly Gly Lys Val Lys
            165                 170                 175

Leu Ser Gly Ser Ile Ser Ser Gln Tyr Leu Thr Ala Leu Leu Met Ala
            180                 185                 190

Ala Pro Leu Ala Leu Gly Asp Val Glu Ile Glu Ile Ile Asp Lys Leu
            195                 200                 205

Ile Ser Leu Pro Tyr Val Glu Met Thr Leu Lys Leu Met Glu Arg Phe
210                 215                 220
```

-continued

```
Gly Val Phe Val Glu His Ser Ser Ser Trp Asp Arg Phe Leu Val Lys
225                 230                 235                 240

Gly Gly Gln Lys Tyr Lys Ser Pro Gly Lys Ala Phe Val Glu Gly Asp
                245                 250                 255

Ala Ser Ser Ala Ser Tyr Phe Leu Ala Gly Ala Ala Val Thr Gly Gly
            260                 265                 270

Thr Val Thr Val Glu Gly Cys Gly Thr Ala Ser Leu Gln Gly Asp Val
        275                 280                 285

Lys Phe Ala Glu Val Leu Glu Lys Met Gly Ala Glu Val Thr Trp Thr
    290                 295                 300

Ser Asn Ser Val Thr Val Lys Gly Pro Pro Arg Asn Ser Ser Gly Met
305                 310                 315                 320

Lys His Leu Arg Ala Ile Asp Val Asn Met Asn Lys Met Pro Asp Val
                325                 330                 335

Ala Met Thr Leu Ala Val Val Ala Leu Phe Ala Asp Gly Pro Thr Thr
            340                 345                 350

Ile Arg Asp Val Ala Ser Trp Arg Val Lys Glu Ser Glu Arg Met Ile
        355                 360                 365

Ala Ile Cys Thr Glu Leu Arg Lys Leu Gly Ala Thr Val Val Glu Gly
    370                 375                 380

Ser Asp Tyr Cys Ile Ile Thr Pro Pro Gly Lys Leu Asn Val Thr Glu
385                 390                 395                 400

Ile Asp Thr Tyr Gly Asp His Arg Met Ala Met Ala Phe Ser Leu Ala
                405                 410                 415

Ala Cys Gly Asp Val Pro Val Thr Ile Lys Asp Pro Gly Cys Thr Arg
            420                 425                 430

Lys Thr Phe Pro Asp Tyr Phe Glu Arg Leu Gln Gln Tyr Ser Lys His
        435                 440                 445

<210> SEQ ID NO 23
<211> LENGTH: 445
<212> TYPE: PRT
<213> ORGANISM: Artificial
<220> FEATURE:
<223> OTHER INFORMATION: Sorghum halapense H6T5X2 with C1 mutations
<400> SEQUENCE: 23

Ala Arg Gly Trp Glu Glu Ile Val Leu Gln Pro Ile Lys Glu Ile Ser
1               5                   10                  15

Gly Thr Val Lys Leu Pro Gly Ser Lys Ser Leu Ser Asn Arg Ile Leu
            20                  25                  30

Leu Leu Ala Ala Leu Ser Glu Gly Thr Thr Val Val Asp Asn Leu Leu
        35                  40                  45

Asn Ser Glu Asp Val His Tyr Met Leu Gly Ala Leu Asn Thr Leu Gly
    50                  55                  60

Leu Ser Val Glu Ala Asp Lys Val Ala Lys Arg Ala Val Val Val Gly
65                  70                  75                  80

Cys Gly Gly Arg Phe Pro Val Glu Asp Ala Lys Glu Glu Val Gln Leu
                85                  90                  95

Phe Cys Gly Asn Ala Ala Thr Ala Met Arg Pro Leu Thr Ala Ala Val
            100                 105                 110

Thr Ala Ala Gly Gly Asn Ala Thr Tyr Val Leu Asp Gly Val Pro Arg
        115                 120                 125

Met Arg Glu Arg Pro Ile Gly Asp Leu Val Val Gly Leu Lys Gln Leu
    130                 135                 140
```

Gly Ala Asp Val Asp Cys Phe Leu Gly Thr Asp Cys Pro Pro Val Arg
145                 150                 155                 160

Ile Asn Gly Ile Gly Gly Leu Pro Gly Gly Lys Val Lys Leu Ser Gly
            165                 170                 175

Ser Ile Ser Ser Gln Tyr Leu Ser Ala Leu Leu Met Ala Ala Pro Leu
        180                 185                 190

Ala Leu Gly Asp Val Glu Ile Glu Ile Ile Asp Lys Leu Ile Ser Leu
    195                 200                 205

Pro Tyr Val Glu Met Thr Leu Arg Leu Met Glu Arg Phe Gly Val Lys
210                 215                 220

Ala Glu His Ser Asp Ser Trp Asp Arg Phe Tyr Ile Lys Gly Gly Gln
225                 230                 235                 240

Lys Tyr Glu Ser Pro Lys Asn Ala Tyr Val Glu Gly Asp Ala Ser Ser
                245                 250                 255

Ala Ser Tyr Phe Leu Ala Gly Ala Ala Ile Thr Gly Thr Val Thr
            260                 265                 270

Val Glu Gly Cys Gly Thr Thr Ser Leu Gln Gly Asp Val Lys Phe Ala
        275                 280                 285

Glu Val Leu Glu Met Met Gly Ala Lys Val Thr Trp Thr Glu Thr Ser
290                 295                 300

Val Thr Val Thr Gly Pro Pro Arg Gln Pro Phe Gly Arg Lys His Leu
305                 310                 315                 320

Lys Ala Ile Asp Val Asn Met Asn Lys Met Pro Asp Val Ala Met Thr
                325                 330                 335

Leu Ala Val Val Ala Leu Phe Ala Asp Gly Pro Thr Ala Ile Arg Asp
            340                 345                 350

Val Ala Ser Trp Arg Val Lys Glu Thr Glu Arg Met Val Ala Ile Arg
        355                 360                 365

Thr Glu Leu Thr Lys Leu Gly Ala Ser Val Glu Glu Gly Pro Asp Tyr
370                 375                 380

Cys Ile Ile Thr Pro Pro Lys Leu Asn Val Thr Ala Ile Asp Thr
385                 390                 395                 400

Tyr Gly Asp His Arg Met Ala Met Ala Phe Ser Leu Ala Ala Cys Ala
                405                 410                 415

Glu Val Pro Val Thr Ile Arg Asp Pro Gly Cys Thr Arg Lys Thr Phe
            420                 425                 430

Pro Asp Tyr Phe Asp Val Leu Ser Thr Phe Val Lys Asn
        435                 440                 445

<210> SEQ ID NO 24
<211> LENGTH: 1362
<212> TYPE: DNA
<213> ORGANISM: Zea mays

<400> SEQUENCE: 24
gctggtgcgg aggaaattgt gctgcagcct atcaaagaaa tctctggtac cgtgaagttg    60
ccgggctcca aaagcttgtc taaccgtatc ctgctgctgg ccgcattgag cgagggtacg   120
accgttgtgg acaatctgct gaatagcgaa gatgtccact atatgctggg tgcactgcgt   180
accttgggcc tgagcgttga ggcggacaag gccgcgaagc gcgctgttgt tgtcggttgc   240
ggcggtaagt tcccggttga ggatgccaag gaagaggttc aactgttctt gggcaatgct   300
ggtaccgcaa tgcgtcctct gacggcggca gtgaccgcag ctggcggtaa tgctacctac   360
gtcctggacg gcgtgccgcg tatgcgcgag cgtccgattg gcgatctggt tgtgggtctg   420

```
aagcagttgg gcgcagatgt cgactgtttt ctgggcacgg actgcccgcc tgtccgcgtg    480
aacggtattg gtggcctgcc gggtggtaaa gtcaagctga gcggcagcat tagcagccaa    540
tacctgtccg cattgctgat ggcggcaccg ctggccctgg gcgacgtaga aattgagatc    600
atcgacaagc tgatttccat cccgtacgtc gaaatgacgc tgcgtctgat ggagcgtttc    660
ggcgtgaagg cggaacatag cgacagctgg gaccgttttt acatcaaagg tggtcagaag    720
tacaaaagcc cgaaaaacgc gtacgttgag ggcgatgcga gcagcgccag ctatttcttg    780
gcgggtgcgg cgatcacggg cggtacggtg accgttgagg gttgcggtac gacgtccctg    840
caaggcgacg tgaaattcgc tgaggttctg gaaatgatgg gtgcgaaggt cacttggacc    900
gagactagcg ttaccgtgac cggtccaccg cgcgaaccgt tcggccgcaa gcatctgaaa    960
gcgattgatg tgaacatgaa taagatgccg gatgtcgcga tgaccctggc cgtcgttgcc   1020
ctgtttgcgg acggtccgac cgcgattcgt gatgttgcat cgtggcgcgt gaaagagact   1080
gaacgtatgg tggcgattcg taccgagctg accaaactgg gtgcaagcgt tgaagagggt   1140
ccggattatt gtattatcac gccgccagaa aaactgaacg ttacggccat cgacacctat   1200
gatgaccacc gcatggcgat ggcgttcagc ctggcggcat gcgcggaggt gccggtcacc   1260
attcgtgatc cggttgtac ccgtaaaacc tttccggact attttgatgt tctgagcacc   1320
tttgtcaaaa actaccctta cgatgttcct gattacgctt aa                     1362
```

<210> SEQ ID NO 25
<211> LENGTH: 1362
<212> TYPE: DNA
<213> ORGANISM: Artificial
<220> FEATURE:
<223> OTHER INFORMATION: DNA sequence of maize EPSPS variant H6

<400> SEQUENCE: 25

```
cgtggttggg aggaaattgt gctgcagcct atcaaagaaa tctctggtac cgtgaagttg     60
ccgggctcca aaagcttgtc taaccgtatc ctgctgctgg ccgcattgag cgagggtacg    120
accgttgtgg acaatctgct gaatagcgaa gatgtccact atatgctggg tgcactgcgt    180
accttgggcc tgagcgttga ggcggacaag caggcgaagc gcgctgttgt tgtcggttgc    240
ggcggtcgtt tcccggttga ggatgccaag gaagaggttc aactgttctg cggcaatgct    300
gctactgcaa tgcgtccgct gacggcggca gtgaccgcag ctggcggtaa tgctacctac    360
gtcctggacg gcgtgccgcg tatgcgcgag cgtccgattg cgatctggt tgtgggtctg    420 aagcagttgg gcgcagatgt cgactgtttt ctgggcacgg actgcccgcc tgtccgcgtg    480
aacggtattg gtggcctgcc gggtggtaaa gtcaagctga gcggcagcat tagcagccaa    540
tacctgtccg cattgctgat ggcggcaccg ctggccctgg gcgacgtaga aattgagatc    600
atcgacaagc tgatttccct gccgtacgtc gaaatgacgc tgcgtctgat ggagcgtttc    660
ggcgtgaagg cggaacatag cgacagctgg gaccgttttt acatcaaagg tggtcagaag    720
tacaaaagcc cgaaaaacgc gtacgttgag ggcgatgcga gcagcgccag ctatttcttg    780
gcgggtgcgg cgatcacggg cggtacggtg accgttgagg gttgcggtac ggcttccctg    840
caaggcgacg tgaaattcgc tgaggttctg gaaatgatgg gtgcgaaggt cacttggacc    900
agtactagcg ttaccgtgac cggtccaccg cgcgaaccgt tcggccgcaa gcatctgaaa    960
gcgattgatg tgaacatgaa taagatgccg gatgtcgcga tgaccctggc cgtcgttgcc   1020
ctgtttgcgg acggtccgac cgcgattcgt gatgttgcat cgtggcgcgt gaaagagagt   1080
gaacgtatgg tggcgattcg taccgagctg accaaactgg gtgcaagcgt tgaagagggt   1140
```

```
ccggattatt gtattatcac gccgccagga aaactgaacg ttacggccat cgacacctat   1200
ggtgaccacc gcatggcgat ggcgttcagc ctggcggcat gcggtgaggt gccggtcacc   1260
attcgtgatc cgggttgtac ccgtaaaacc tttccggact attttgaccg gctgagtcaa   1320
tttgtcaaaa attaccctta cgatgttcct gattacgctt aa                      1362
```

<210> SEQ ID NO 26
<211> LENGTH: 186
<212> TYPE: DNA
<213> ORGANISM: Arabidopsis thaliana

<400> SEQUENCE: 26

```
atggcggcaa tggcgacgaa ggctgctgcg ggaaccgtgt ctttggacct tgccgctcca    60
agcagaagac accacagacc aagctctgct agacctccat tcagacctgc agttaggggg   120
ttacgtgctc ctggaaggag agttatcgct gcccctccag cagctgcagc ggcagccgca   180
gttcag                                                              186
```

<210> SEQ ID NO 27
<211> LENGTH: 162
<212> TYPE: DNA
<213> ORGANISM: Artificial
<220> FEATURE:
<223> OTHER INFORMATION: artificial CTP termed 6H1

<400> SEQUENCE: 27

```
atggctgcaa ctactcttac atctgcttta cctggtgctt tcagttcatc ccagagacca    60
agtgctcctt ttaacttaca agatcacct agagtgctta gaaggttcaa cagaaagaca   120
ggacgtcaac ctcgtggact tgttcgtgct gcaaaggctc aa                      162
```

<210> SEQ ID NO 28
<211> LENGTH: 993
<212> TYPE: DNA
<213> ORGANISM: Arabidopsis thaliana

<400> SEQUENCE: 28

```
agatcgataa tctatttttg ttttaaatag gagaaaacaa aaattgattt tttgtttggt    60
ttttgttttg gtgtctaaat atatgtagat tttctagttt ctagtccttc gcttccaagt   120
tcctcgatgg ctcaatgcca atttagtcag ataagattat gctgcaactg ctagagcgac   180
tctctcctac ttcattttag tccatactag ttcattttat ctccaagaaa atgactccgt   240
tttgcttcaa agctcaaaga tgattctttt tttaatgggc cctcttgaaa aatgggtaaa   300
atcttggtct ttttacagat agcaaacata tacaaattat ggagaaaaca ggattatatt   360
gatgcagctt cgttgtagac agacttgtag tcgttttctt cattttccca ttcctctgct   420
aaattattaa atccaacaaa aacaaatttt cttctgttgc ttgataaaat ctatgtggaa   480
tatctatatc tacacactac tgaagaccaa gaagtaaaca ttagtttgcc tgatcttcac   540
ctacctcaaa cgagaagtag aagttttat ggtgactttt gtatttagag aaacaatggg   600
attccagttt aagttggctc tttttaactt tgctaacata tgcctgaaag tggaagacaa   660
gaacttggtt taagaaacct caagcgattg cgatttggg tcttaagctt gaaaaaagtg   720
ttgtatggaa caaacaaact aacatatcgg aacaagcttg gctttggttt taaagctgat   780
agataatggt cgaaccataa ccggtatggc ccaagatgtg catgttttt aaaactcacc   840 aaagctatat cactaaccca cacattcttg cagaaggttt tagaatcaca aagcataact   900
```

```
cacctacccc taaaccaact ccaatttctc tcctcctcta ttaaatcttt ctcaatcatc    960
tttctttgag tcttttgcct tggaatcctg atc                                 993
```

<210> SEQ ID NO 29
<211> LENGTH: 1277
<212> TYPE: DNA
<213> ORGANISM: Arabidopsis thaliana

<400> SEQUENCE: 29

```
cggatttgga gccaagtctc ataaacgcca ttgtggaaga aagtcttgag ttggtggtaa     60
tgtaacagag tagtaagaac agagaagaga gagagtgtga gatacatgaa ttgtcgggca    120
acaaaaatcc tgaacatctt attttagcaa agagaaagag ttccgagtcg gtagcagaag    180
agtgaggaga aatttaagct cttggacttg tgaattgttc cgcctcttga atacttcttc    240
aatcctcata tattcttctt ctatgttacc tgaaaaccgg catttaatct cgcgggttta    300
ttccggttca acattttttt tgttttgagt tattatctgg gcttaataac gcaggcctga    360
aataaattca aggcccaact gttttttttt aagaagttgc tgttaaaaaa aaaaggggga    420
ttaacaacaa caacaaaaaa agataaagaa aataataaca attactttaa ttgtagacta    480
aaaaaacata gattttatca tgaaaaaaag agaaaagaaa taaaaacttg gatcaaaaaa    540
aaaacataca gatcttctaa ttattaactt ttcttaaaaa ttaggtcctt tttcccaaca    600
attaggttta gagttttgga attaaaccaa aaagattgtt ctaaaaaata ctcaaatttg    660
gtagataagt ttccttattt taattagtca atggtagata cttttctttc ttttctttat    720
tagagtagat tagaatcttt tatgccaagt attgataaat taaatcaaga agataaaacta   780 tcataatcaa catgaaatta aaagaaaaat ctcatatata gtattagtat tctctatata    840
tattatgatt gctattctt aatgggttgg gttaaccaag acatagtctt aatggaagaa     900
atcttttttg aacttttttcc ttattgatta aattcttcta tagaaaagaa agaaattatt    960
tgaggaaaag tatatacaaa aagaaaaata gaaaaatgtc agtgaagcag atgtaatgga   1020
tgacctaatc caaccaccac cataggatgt ttctacttga gtcggtcttt taaaaacgca   1080
cggtggaaaa tatgacacgt accatatgat tccttccttt agtttcgtga taataatcct   1140
caactgatat cttccttttt ttgttttggc taaagatatt ttattctcat taatagaaaa   1200
gacggttttg ggcttttggt ttgcgatata aagaagacct tcgtgtggaa gataataatt   1260
catcctttcg tctttt                                                   1277
```

<210> SEQ ID NO 30
<211> LENGTH: 917
<212> TYPE: DNA
<213> ORGANISM: Arabidopsis thaliana

<400> SEQUENCE: 30

```
atcaggatat tcttgtttaa gatgttgaac tctatggagg tttgtatgaa ctgatgatct     60
aggaccggat aagttcccct cttcatagcg aacttattca agaatgtttt tgtgtatcat    120
tcttgttaca ttgttattaa tgaaaaaata ttattggtca ttggactgaa cacgagtgtt    180
aaatatggac caggccccaa ataagatcca ttgatatatg aattaaataa caagaataaa    240
tcgagtcacc aaaccacttg cctttttttaa cgagacttgt tcaccaactt gatacaaaag    300
tcattatcct atgcaaatca ataatcatac aaaaatatcc aataacacta aaaaattaaa    360
agaaatggat aatttcacaa tatgttatac gataaagaag ttacttttcc aagaaattca    420
ctgattttat aagcccactt gcattagata aatggcaaaa aaaaacaaaa aggaaaagaa    480
```

```
ataaagcacg aagaattcta gaaaatacga aatacgcttc aatgcagtgg gacccacggt    540
tcaattattg ccaattttca gctccaccgt atatttaaaa aataaaacga taatgctaaa    600
aaaatataaa tcgtaacgat cgttaaatct caacggctgg atcttatgac gaccgttaga    660
aattgtggtt gtcgacgagt cagtaataaa cggcgtcaaa gtggttgcag ccggcacaca    720
cgagtcgtgt ttatcaactc aaagcacaaa tactttcct caacctaaaa ataaggcaat     780
tagccaaaaa caactttgcg tgtaaacaac gctcaataca cgtgtcattt tattattagc    840
tattgcttca ccgccttagc tttctcgtga cctagtcgtc ctcgtctttt cttcttcttc    900
ttctataaaa caatacc                                                    917

<210> SEQ ID NO 31
<211> LENGTH: 27
<212> TYPE: DNA
<213> ORGANISM: Human Influenza Virus

<400> SEQUENCE: 31 taccccttacg atgttcctga ttacgct                                         27

<210> SEQ ID NO 32
<211> LENGTH: 1157
<212> TYPE: DNA
<213> ORGANISM: Phaseolus vulgaris

<400> SEQUENCE: 32
aagtatgaac taaaatgcat gtaggtgtaa gagctcatgg agagcatgga atattgtatc     60
cgaccatgta acagtataat aactgagctc catctcactt cttctatgaa taaacaaagg    120
atgttatgat atattaacac tctatctatg caccttattg ttctatgata aatttcctct    180
tattattata aatcatctga atcgtgacgg cttatggaat gcttcaaata gtacaaaaac    240
aaatgtgtac tataagactt tctaaacaat tctaacctta gcattgtgga cgagacataa    300
gtgttaagaa gacataacaa ttataatgga agaagtttgt ctccatttat atattatata    360
ttacccactt atgtattata ttaggatgtt aaggagacat aacaattata agagagaag     420 tttgtatcca tttatatatt atatactacc cattatatata ttatacttat ccacttattt    480
aatgtcttta taaggtttga tccatgatat ttctaatatt ttagttgata tgtatatgaa    540
aaggtactat ttgaactctc ttactctgta taaaggttgg atcatcctta aagtgggtct    600
atttaatttt attgcttctt acagataaaa aaaaaattat gagttggttt gataaaatat    660
tgaaggattt aaaataataa taataacat ataatatatg tatataaatt tattataata    720
taacatttat ctataaaaaa gtaaatattg tcataaatct atacaatcgt ttagccttgc    780
tggaacgaat ctcaattatt taaacgagag taaacatatt tgacttttg gttatttaac     840 aaattattat ttaacactat atgaaatttt tttttttatc agcaaagaat aaaattaaat    900
taagaaggac aatggtgtcc caatccttat acaaccaact tccacaagaa agtcaagtca    960
gagacaacaa aaaaacaagc aaaggaaatt ttttaatttg agttgtcttg tttgctgcat   1020
aatttatgca gtaaaacact acacataacc cttttagcag tagagcaatg gttgaccgtg   1080
tgcttagctt cttttatttt atttttttat cagcaaagaa taaataaaat aaaatgagac   1140
acttcaggga tgtttca                                                  1157

<210> SEQ ID NO 33
<211> LENGTH: 1362
<212> TYPE: DNA
```

<213> ORGANISM: Artificial
<220> FEATURE:
<223> OTHER INFORMATION: DNA sequence of maize EPSPS variant C1

<400> SEQUENCE: 33

| | | | | | |
|---|---|---|---|---|---|
| cgtggttggg | aggaaattgt | gctgcagcct | atcaaagaaa | tctctggtac | cgtgaagttg | 60 |
| ccgggctcca | aaagcttgtc | taaccgtatc | ctgctgctgg | ccgcattgag | cgagggtacg | 120 |
| accgttgtgg | acaatctgct | gaatagcgaa | gatgtccact | atatgctggg | tgcactgcgt | 180 |
| accttgggcc | tgagcgttga | ggcggacaag | gccgcgaagc | gcgctgttgt | tgtcggttgc | 240 |
| ggcggtcgtt | tcccggttga | ggatgccaag | gaagaggttc | aactgttctg | cggcaatgct | 300 |
| gctaccgcaa | tgcgtcctct | gacggcggca | gtgaccgcag | ctggcggtaa | tgctacctac | 360 |
| gtcctggacg | gcgtgccgcg | tatgcgcgag | cgtccgattg | gcgatctggt | tgtgggtctg | 420 |
| aagcagttgg | gcgcagatgt | cgactgtttt | ctgggcacgg | actgcccgcc | tgtccgcgtg | 480 |
| aacggtattg | gtggcctgcc | gggtggtaaa | gtcaagctga | gcggcagcat | tagcagccaa | 540 |
| tacctgtccg | cattgctgat | ggcggcaccg | ctggccctgg | gcgacgtaga | aattgagatc | 600 |
| atcgacaagc | tgatttcctt | accgtacgtc | gaaatgacgc | tgcgtctgat | ggagcgtttc | 660 |
| ggcgtgaagg | cggaacatag | cgacagctgg | gaccgttttt | acatcaaagg | tggtcagaag | 720 |
| tacgaaagcc | cgaaaaacgc | gtacgttgag | ggcgatgcga | gcagcgccag | ctatttcttg | 780 |
| gcgggtgcgg | cgatcacggg | cggtacggtg | accgttgagg | gttgcggtac | gacgtccctg | 840 |
| caaggcgacg | tgaaattcgc | tgaggttctg | gaaatgatgg | gtgcgaaggt | cacttggacc | 900 |
| gagactagcg | ttaccgtgac | cggtccaccg | cgcgaaccgt | tcggccgcaa | gcatctgaaa | 960 |
| gcgattgatg | tgaacatgaa | taagatgccg | gatgtcgcga | tgaccctggc | cgtcgttgcc | 1020 |
| ctgtttgcgc | acgtccgac | cgcgattcgt | gatgttgcat | cgtggcgcgt | gaaagagact | 1080 |
| gaacgtatgg | tggcgattcg | taccgagctg | accaaactgg | gtgcaagcgt | tgaagagggt | 1140 |
| ccggattatt | gtattatcac | gccgccacca | aaactgaacg | ttacggccat | cgacacctat | 1200 |
| ggtgaccacc | gcatggcgat | ggcgttcagc | ctggcggcat | gcgcggaggt | gccggtcacc | 1260 |
| attcgtgatc | cggggttgtac | ccgtaaaaacc | tttccggact | attttgatgt | tctgagcacc | 1320 |
| tttgtcaaaa | actacccctta | cgatgttcct | gattacgctt | aa | | 1362 |

<210> SEQ ID NO 34
<211> LENGTH: 1362
<212> TYPE: DNA
<213> ORGANISM: Artificial
<220> FEATURE:
<223> OTHER INFORMATION: DNA sequence of maize EPSPS variant C2

<400> SEQUENCE: 34

| | | | | | |
|---|---|---|---|---|---|
| gctggttggg | aggaaattgt | gctgcagcct | atcaaagaaa | tctctggtac | cgtgaagttg | 60 |
| ccgggctcca | aaagcttgtc | taaccgtatc | ctgctgctgg | ccgcattgag | cgagggtacg | 120 |
| accgttgtgg | acaatctgct | gaatagcgaa | gatgtcatgt | atatgctggg | tgcactgcgt | 180 |
| accttgggcc | tgagcgttga | ggcggacaag | gccgcgaagc | gcgctgttgt | tgtcggttgc | 240 |
| ggcggtaagt | tcccggttga | ggatgccaag | gaagaggttc | aactgttctg | cggcaatgct | 300 |
| gctactgcaa | tgcgtccgct | gacggcggca | gtgaccgcag | ctggcggtaa | tgctacctac | 360 |
| gtcctggacg | gcgtgccgcg | tatgcgcgag | cgtccgattg | gcgatctggt | tgtgggtctg | 420 |
| aagcagttgg | gcgcagatgt | cgactgtttt | ctgggcacgg | actgcccgcc | tgtccgcgtg | 480 |
| aacggtattg | gtggcctgcc | gggtggtaaa | gtccgcctga | gcggcagcat | tagcagccaa | 540 |

```
                                        -continued tacctgtccg cattgctgat ggcggcaccg ctggccctgg gcgacgtaga aattgagatc    600
atcgacaagc tgatttccct gccgtacgtc gaaatgacgc tgcgtctgat ggagcgtttc    660
ggcgtgaagg cggaacatag cgacagctgg gaccgttttt acatcaaagg tggtcagaag    720
tacgaaagcc cgaaaaacgc gtacgttgag ggcgatgcga gcagcgccag ctatttcttg    780
gcgggtgcgg cgatcacggg cggtacggtg accgttgagg gttgcggtac gacgtccctg    840
caaggcgacg tgaaattcgc tgaggttctg gaaatgatgg gtgcgaaggt cacttggacc    900
agtactagcg ttaccgtgac cggtccaccg cgcgaaccgt tcggccgcaa gcatctgaaa    960
gcgattgatg tgaacatgaa taagatgccg gatgtcgcga tgaccctggc cgtcgttgcc   1020
ctgtttgcgg acggtccgac cgcgattcgt gatgttgcat cgtggcgcgt gaaagagagt   1080
gaacgtatgg tggcgattcg taccgagctg accaaactgg gtgcaagcgt tgaagagggt   1140
ccggattatt gtattatcac gccgccaccc aaactgaacg ttacggccat cgacacctat   1200
ggtgaccacc gcatggcgat ggcgttcagc ctggcggcat gcggtgaggt gccggtcacc   1260
attcgtgatc cgggttgtac ccgtaaaacc tttccggact attttgaccg gctgcgtcaa   1320
gttgtcaaaa attaccctta cgatgttcct gattacgctt aa                      1362
```

PLANT EPSP SYNTHASES AND METHODS OF USE

CROSS REFERENCE TO RELATED APPLICATIONS

This application claims the benefit of U.S. Provisional Application No. 62/234,818, filed Sep. 30, 2015, the entire contents of which are hereby incorporated by reference.

FIELD

The field relates to the field of molecular biology. More specifically, it pertains to sequences that confer tolerance to glyphosate.

REFERENCE TO SEQUENCE LISTING SUBMITTED ELECTRONICALLY

The official copy of the sequence listing is submitted electronically via EFS-Web as an ASCII formatted sequence listing with a file named BB2501 PCT_SequenceListing_ST25.txt created on Sep. 19, 2016 and having a size 96 kilobytes and is filed concurrently with the specification. The sequence listing contained in this ASCII formatted document is part of the specification and is herein incorporated by reference in its entirety.

BACKGROUND

EPSP (5-enolpyruvylshikimate-3-phosphate) synthase is an enzyme that catalyzes the conversion of phosphoenolpyruvate and 3-phosphoshikimate to phosphate and 5-enolpyruvylshikimate-3-phosphate (EPSP), and it participates in the biosynthesis of the aromatic amino acids phenylalanine, tyrosine, and tryptophan. Glyphosate, the top selling herbicide in the world, acts a competitive inhibitor for phosphoenolpyruvate.

Glyphosate tolerant crops have been created by introducing glyphosate-insensitive 5-enolpyruvylshikimate-3-phosphate synthase (EPSPS) enzymes into plants. In one example, maize event NK603 uses EPSPS from *Agrobacterium* sp. strain CP4. The enzyme is highly insensitive to inhibition by glyphosate while retaining catalytic efficiency similar to native plant enzymes (Sikorski and Gruys. 1997. *Acc. Chem. Res.* 30:2-8). In another example, maize event GA21 uses a double mutant maize EPSPS in which threonine at position 103 is changed to isoleucine and proline at position 107 is changed to serine.

Plant EPSP synthases having kinetic properties that provide adequate tolerance to glyphosate and catalytic capacity to sustain normal rates of metabolic flux are desired.

SUMMARY

Plant EPSP synthases (herein referred to as EPSPS) and the polynucleotides that encode them are provided herein. Methods for generating glyphosate tolerant plants that are tolerant to the plant EPSPS enzymes are also provided.

Polynucleotides are provided herein that encode plant EPSPS polypeptides that comprise G102A and at least one or more amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the plant EPSPS polypeptide comprises a sequence that is at least 90% identical to SEQ ID NO:2. In some embodiments, the polynucleotides encode plant EPSPS polypeptides that comprise G102A and at least two or more, three or more, or four or more amino acid mutations selected from the group consisting of (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the plant EPSPS polypeptide comprises a sequence that is at least 90% identical to SEQ ID NO:2.

In other embodiments, the polynucleotide encodes a plant EPSPS polypeptide that comprises A4W, H54M, L98C, G102A, K173R, I208L, K243E, E302S, T361S, E391P, D402G, A416G, V438R, S440R, T441Q, and F442V. In still other embodiments, the polynucleotide encodes a plant EPSPS polypeptide that comprises A2R, A4W, A72Q, K84R, L98C, G102A, I208L, T279A, E302S, T361S, E391G, D402G, A416G, V438R, and T441Q. In still other embodiments, the polynucleotide encodes a plant EPSPS polypeptide that comprises A2R, A4W, K84R, L98C, G102A, I208L, K243E, E391P, and D402G. In still other embodiments, the polynucleotide encodes the plant EPSPS polypeptide set forth in SEQ ID NO:4, SEQ ID NO:5, or SEQ ID NO:6.

Also provided are recombinant DNA constructs comprising the polynucleotides disclosed herein; plant cells comprising in their genomes a polynucleotide disclosed herein or a recombinant DNA construct comprising such; and plants comprising in their genomes a polynucleotide disclosed herein or a recombinant DNA construct comprising such. In some embodiments, the plant cell is a maize cell. In some embodiments, the plant is maize.

Methods of generating glyphosate tolerant plants are provided herein. The methods comprise expressing in a regenerable plant cell a recombinant DNA construct comprising a polynucleotide operably linked to at least one regulatory sequence, wherein the polynucleotide encodes a plant EPSPS polypeptide that comprises G102A and at least one amino acid mutation selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the plant EPSPS polypeptide comprises a sequence that is at least 90% identical to SEQ ID NO:2; and generating a glyphosate tolerant plant that comprises in its genome the recombinant DNA construct. In some embodiments, the methods include expressing in a plant cell a recombinant DNA construct comprising a polynucleotide encoding a plant EPSPS polypeptide comprising G102A and at least two, at least three, or at least four amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS polypeptide comprises a sequence that is at least 90% identical to SEQ ID NO:2.

In other embodiments, the method comprises expressing in a plant cell a recombinant DNA comprising a polynucleotide that encodes a plant EPSPS polypeptide that comprises A4W, H54M, L98C, G102A, K173R, I208L, K243E, E302S, T361S, E391P, D402G, A416G, V438R, S440R, T441Q, and F442V. In still other embodiments, the method comprises expressing in a plant cell a recombinant DNA comprising a polynucleotide that encodes a plant EPSPS polypeptide that comprises A2R, A4W, A72Q, K84R, L98C, G102A, I208L, T279A, E302S, T361S, E391G, D402G, A416G, V438R, and T441Q. In still other embodiments, the method comprises expressing in a plant cell a recombinant DNA comprising a polynucleotide that encodes a plant EPSPS polypeptide that comprises A2R, A4W, K84R, L98C, G102A, I208L, K243E, E391P, and D402G. In still other embodiments, the method comprises expressing in a plant cell a recombinant DNA comprising a polynucleotide that encodes the plant EPSPS polypeptide set forth in SEQ ID NO:4, SEQ ID NO:5, or SEQ ID NO:6.

Methods of generating glyphosate tolerant plants are provided herein, in which an endogenous plant EPSPS gene (in a plant cell) is modified to encode a glyphosate tolerant EPSPS protein that comprises G102A and at least one amino acid mutation selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the endogenous plant EPSPS gene encodes a polypeptide comprising a sequence that is at least 90% identical to SEQ ID NO:2; and a glyphosate tolerant plant is grown from the plant cell. In some embodiments the modified endogenous plant EPSPS gene encodes a glyphosate tolerant EPSPS protein that comprises G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the endogenous plant EPSPS gene encodes a polypeptide comprising a sequence that is at least 90% identical to SEQ ID NO:2.

In other embodiments, the modified endogenous plant EPSPS gene encodes a glyphosate tolerant EPSPS protein that comprises: A4W, H54M, L98C, G102A, K173R, I208L, K243E, E302S, T361S, E391P, D402G, A416G, V438R, S440R, T441Q, and F442V. In still other embodiments, the modified endogenous plant EPSPS gene encodes a glyphosate tolerant EPSPS protein that comprises: A2R, A4W, A72Q, K84R, L98C, G102A, I208L, T279A, E302S, T361S, E391G, D402G, A416G, V438R, and T441Q. In still other embodiments, the modified endogenous plant EPSPS gene encodes a glyphosate tolerant EPSPS protein that comprises A2R, A4W, K84R, L98C, G102A, I208L, K243E, E391P, and D402G. In still other embodiments, the modified endogenous plant EPSPS gene encodes a glyphosate tolerant EPSPS protein that comprises the plant EPSPS polypeptide set forth in SEQ ID NO:4, SEQ ID NO:5, or SEQ ID NO:6.

The endogenous plant EPSPS gene may be modified by a CRISPR/Cas guide RNA-mediated system, a Zn-finger nuclease-mediated system, a meganuclease-mediated system, or an oligonucleobase-mediated system.

Polynucleotide constructs that provide a guide RNA in a plant cell are provided herein in which the guide RNA targets an endogenous EPSPS gene of the plant cell and the polynucleotide construct further comprises one or more polynucleotide modification templates to generate a modified endogenous EPSPS gene that encodes a plant EPSPS polypeptide comprising G102A and at least one amino acid mutation selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the endogenous plant EPSPS gene encodes a polypeptide comprising a sequence that is at least 90% identical to SEQ ID NO:2. In some embodiments, the polynucleotide construct comprises one or more polynucleotide modification templates to generate a modified endogenous EPSPS gene encoding a plant EPSPS polypeptide that comprises G102A and at least two, at least three, or at least four amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (5) T441Q, and (t) F442V, wherein each amino acid position corresponds to the amino acid mutation position set forth in SEQ ID NO:1 and wherein the endogenous plant EPSPS gene encodes a polypeptide comprising a sequence that is at least 90% identical to SEQ ID NO:2.

In other embodiments, the polynucleotide construct comprises one or more polynucleotide modification templates to generate a modified endogenous EPSPS gene encoding a plant EPSPS polypeptide that comprises: A4W, H54M, L98C, G102A, K173R, I208L, K243E, E302S, T361S, E391P, D402G, A416G, V438R, S440R, T441Q, and F442V. In still other embodiments, the polynucleotide construct comprises one or more polynucleotide modification templates to generate a modified endogenous EPSPS gene encoding a plant EPSPS polypeptide that comprises: A2R, A4W, A72Q, K84R, L98C, G102A, I208L, T279A, E302S, T361S, E391G, D402G, A416G, V438R, and T441Q. In still other embodiments, the polynucleotide construct comprises one or more polynucleotide modification templates to generate a modified endogenous EPSPS gene encoding a plant EPSPS polypeptide that comprises: A2R, A4W, K84R, L98C, G102A, I208L, K243E, E391P, and D402G. In still other embodiments, the polynucleotide construct comprises one or more polynucleotide modification templates to generate a modified endogenous EPSPS gene encoding a plant EPSPS polypeptide that has the amino acid sequence set forth in SEQ ID NO:4, SEQ ID NO:5, or SEQ ID NO:6.

Methods for producing glyphosate tolerant plants are provided herein in which a guide RNA, one or more polynucleotide modification templates, and one or more Cas endonucleases are provided to a plant cell. The Cas endonuclease(s) introduces a double strand break at an endogenous EPSPS gene in the plant cell, and the polynucleotide modification template(s) is used to generate a modified EPSPS gene that encodes a plant EPSPS polypeptide that comprises G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the endogenous plant EPSPS gene encodes a polypeptide comprising a sequence that is at least 90% identical to SEQ ID NO:2. A plant is obtained from the plant cell, and a glyphosate tolerant progeny plant that is void of the guide RNA and Cas endonuclease is generated. In some embodiments, the one or more polynucleotide modification templates are used to generate a modified endogenous EPSPS gene encoding a plant EPSPS polypeptide that comprises G102A and at least two, at least three, or at least four amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid mutation position set forth in SEQ ID NO:1 and wherein the endogenous plant EPSPS gene encodes a polypeptide comprising a sequence that is at least 90% identical to SEQ ID NO:2.

In other embodiments, the one or more polynucleotide modification templates are used to generate a modified endogenous EPSPS gene encoding a plant EPSPS polypeptide that comprises: A4W, H54M, L98C, G102A, K173R, I208L, K243E, E302S, T361S, E391P, D402G, A416G, V438R, S440R, T441Q, and F442V. In still other embodiments, the one or more polynucleotide modification templates are used to generate a modified endogenous EPSPS gene encoding a plant EPSPS polypeptide that comprises: A2R, A4W, A72Q, K84R, L98C, G102A, I208L, T279A, E302S, T361S, E391G, D402G, A416G, V438R, and T441Q. In still other embodiments, the one or more polynucleotide modification templates are used to generate a modified endogenous EPSPS gene encoding a plant EPSPS polypeptide that comprises: A2R, A4W, K84R, L98C, G102A, I208L, K243E, E391P, and D402G. In still other embodiments, the one or more polynucleotide modification templates are used to generate a modified endogenous EPSPS gene encoding a plant EPSPS polypeptide that has the amino acid sequence set forth in SEQ ID NO:4, SEQ ID NO:5, or SEQ ID NO:6.

Also provided herein are glyphosate tolerant maize plants that express an endogenous EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the endogenous plant EPSPS gene encodes a polypeptide comprising a sequence that is at least 90% identical to SEQ ID NO:2. A glyphosate tolerant maize plant may express a plant EPSPS polypeptide having the sequence set forth in SEQ ID NO:4, SEQ ID NO:5, or SEQ ID NO:6.

Also provided herein are glyphosate tolerant sunflower plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:9. A glyphosate tolerant sunflower plant may express a plant EPSPS polypeptide having the sequence set forth in SEQ ID NO:10.

Also provided herein are glyphosate tolerant rice plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:7. A glyphosate tolerant rice plant may express a plant EPSPS polypeptide having the sequence set forth in SEQ ID NO:11.

Also provided herein are glyphosate tolerant *sorghum* plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:8. A glyphosate tolerant *sorghum* plant may express a plant EPSPS polypeptide having the sequence set forth in SEQ ID NO:12.

Also provided herein are glyphosate tolerant soybean plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:13. A glyphosate tolerant soybean plant may express a plant EPSPS polypeptide having the sequence set forth in SEQ ID NO:18. Also provided herein are glyphosate tolerant wheat plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:14. A glyphosate tolerant wheat plant may express a plant EPSPS polypeptide having the sequence set forth in SEQ ID NO:19.

Also provided herein are glyphosate tolerant *Brassica rapa* plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:15. A glyphosate tolerant *Brassica rapa* plant may express a plant EPSPS polypeptide having the sequence set forth in SEQ ID NO:20.

Also provided herein are glyphosate tolerant tomato plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:17. A glyphosate tolerant tomato plant may express a plant EPSPS polypeptide having the sequence set forth in SEQ ID NO:21.

Also provided herein are glyphosate tolerant potato plants that express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:18. A glyphosate tolerant potato plant may express a plant EPSPS polypeptide having the sequence set forth in SEQ ID NO:22.

Methods of weed control in which an effective amount of glyphosate is applied over a population of glyphosate tolerant plants provided herein are also provided. The plants may be maize, sunflower, rice, wheat, tomato, potato, oil seed rape, *sorghum*, or soy. The effective amount of glyphosate applied may be about 50 gram acid equivalent/acre to about 2000 gram acid equivalent/acre.

Polynucleotide modification templates comprising a partial EPSP synthase (EPSPS) sequence, wherein a polynucleotide modification template comprises one or more nucleotide mutations that correspond to G102A and to at least one or more amino acid mutations selected from the group consisting of: a) A2R, b) A4W, c) H54M, d) A72Q, e) K84R, f) L98C, g) K173R, h) I208L, i) K243E, j) T279A, k) E302S, l) T361S, m) E391P, n) E391G, o) D402G, p) A416G, q) V438R, r) S440R, s) T441Q, and t) F442V, wherein each amino acid mutation position corresponds to the amino acid position set forth in SEQ ID NO: 1, are also provided. Plant cells comprising a polynucleotide modification template presented herein, a guide RNA, and CRISPR/Cas9 endonuclease are also provided wherein said combination targets an endogenous maize EPSPS sequence that encodes an EPSPS polypeptide that is at least 90% identical to SEQ ID NO:2.

Also provided is a method of rapidly assaying catalytic efficiency of a plurality of enzyme variants in the presence of an inhibitor. The method includes (a) providing a plurality of enzyme variants; (b) providing the inhibitor; (c) providing the substrate; (d) performing a reaction involving the plurality of enzyme variants and the substrate, at no more than two different inhibitor concentrations; (e) measuring reaction rate at no more than two different inhibitor concentrations; and (f) calculating (kcat/KM)*KI of the plurality of enzyme variants. In some embodiments, one of the inhibitor concentrations is zero. In other embodiments, the substrate is at a concentration that is substantially similar to Michaelis-Menten constant (KM) of a parental enzyme for the enzyme variant. In still other embodiments, the enzyme is at a sufficient concentration to result in a substantially linear reaction rate at the two different inhibitor concentrations. In still other embodiments, one of the inhibitor concentrations is sufficient to result in at least about 50% inhibition. In still other embodiments, the assay is performed in a high-throughput system. In still other embodiments, the catalytic capacity in the presence of the inhibitor is estimated by obtaining a numerical value for (kcat/KM)*KI, wherein kcat is maximum enzyme turnover rate, KM is Michaelis-Menten constant and KI is inhibitor dissociation constant. In some embodiments, the substrate is PEP; the inhibitor is glyphosate; and the plurality of enzyme variants are EPSPS enzyme variants. In some embodiments, the enzyme and the substrate concentrations are the same, at the two inhibitor concentrations.

BRIEF DESCRIPTION OF THE DRAWINGS

FIG. 1 shows an alignment of maize wild-type EPSPS amino acid sequence (SEQ ID NO:1) and a mutated H6 version (SEQ ID NO:5) of the EPSPS sequence.

FIG. 2 shows an alignment of soybean wild-type EPSPS amino acid sequence (SEQ ID NO:13) and a mutated H6 version (SEQ ID NO:18) of the EPSPS sequence.

FIG. 3 shows an alignment of sunflower wild-type EPSPS amino acid sequence (SEQ ID NO:9) and a mutated H6 version (SEQ ID NO:10) of the EPSPS sequence FIG. 4 shows an alignment of rice wild-type EPSPS amino acid sequence (SEQ ID NO:7) and a mutated H6 version (SEQ ID NO:11) of the EPSPS sequence.

FIG. 5 shows an alignment of *sorghum* wild-type EPSPS amino acid sequence (SEQ ID NO:8) and a mutated H6 version (SEQ ID NO:12) of the EPSPS sequence.

FIG. 6 shows an alignment of wheat wild-type EPSPS amino acid sequence (SEQ ID NO:14) and a mutated H6 version (SEQ ID NO:19) of the EPSPS sequence.

FIG. 7 shows an alignment of *B. rapa* wild-type EPSPS amino acid sequence (SEQ ID NO:15) and a mutated H6 version (SEQ ID NO:20) of the EPSPS sequence.

FIG. 8 shows an alignment of *Sorghum* wild-type EPSPS amino acid sequence (SEQ ID NO:8) and a mutated C1 version (SEQ ID NO:23) of the EPSPS sequence.

BRIEF DESCRIPTION OF THE SEQUENCE LISTING

Figure 9:
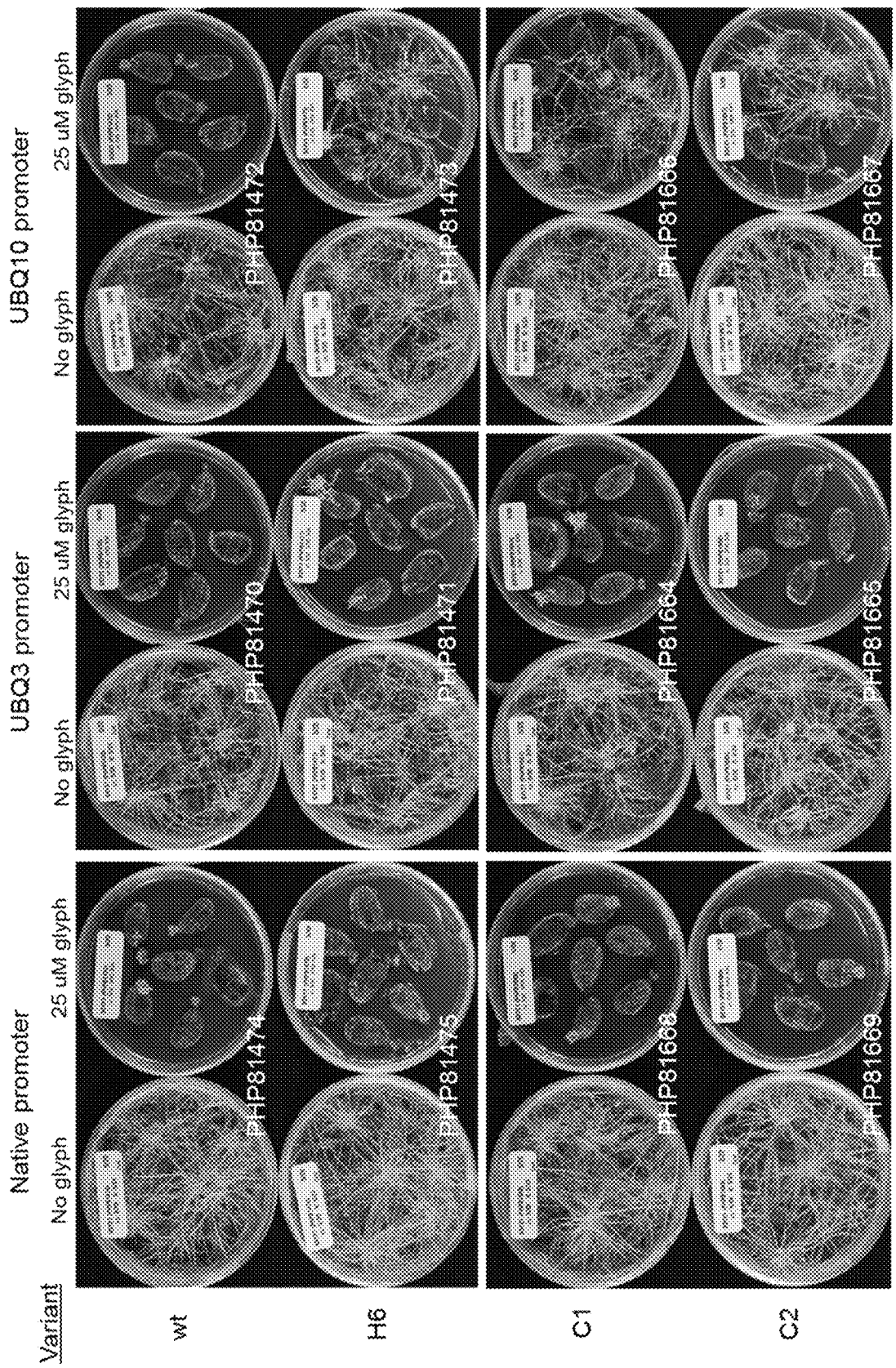
FIG. 9 shows the growth of hairy roots from soybean cotyledons transformed with native maize EPSPS or one of the shuffled variants.

The sequence descriptions and Sequence Listing attached hereto comply with the rules governing nucleotide and/or amino acid sequence disclosures in patent applications as set forth in 37 C.F.R. § 1.821 1.825. The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (2):345 373 (1984) which are herein incorporated by reference. The symbols and format used for nucleotide and amino acid sequence data comply with the rules set forth in 37 C.F.R. § 1.822.

SEQ ID NO:1 is the amino acid sequence of an expressed protein obtained by cloning a synthetic EPSP synthase (in which the nucleotide sequence of the gene encoding SEQ ID NO:2 was modified to add an N-terminal methionine to SEQ ID NO:2 and to optimize codon usage for its expression in *E. coli*) into an expression vector. SEQ ID NO:1 is to be used herein as a reference EPSPS sequence.

SEQ ID NO:2 is the amino acid sequence of a maize EPSPS presented as GenBank entry CAA44974.1 (NCBI GI No. 1524383).

SEQ ID NO:3 is the amino acid sequence of the N-terminal extension.

SEQ ID NO:4 is the amino acid sequence of a maize EPSPS encoded by the nucleotide sequence present in clone 771-C2.

SEQ ID NO:5 is the amino acid sequence of a maize EPSPS encoded by the nucleotide sequence present in clone 868-H6.

SEQ ID NO:6 is the amino acid sequence of a maize EPSPS encoded by the nucleotide sequence present in clone 123-C1.

SEQ ID NO:7 is the amino acid sequence of a native EPSPS from rice (*Oryza sativa*) including the chloroplast transit peptide sequence.

SEQ ID NO:8 is the amino acid sequence of a native EPSPS from sorghum (*Sorghum halepense*) including the chloroplast transit peptide sequence.

SEQ ID NO:9 is an annotated amino acid sequence of a native EPSPS from sunflower (*Helianthus annus*) including the chloroplast transit peptide sequence.

SEQ ID NO:10 is a mutated version of the EPSPS sequence from sunflower (SEQ ID NO:9) that contains the 868-H6 mutations.

SEQ ID NO:11 is a mutated version of the EPSPS sequence from rice (SEQ ID NO:7) that contains the 868-H6 mutations.

SEQ ID NO:12 is a mutated version of the EPSPS sequence from sorghum (SEQ ID NO:8) that contains the 868-H6 mutations.

SEQ ID NO:13 is an amino acid sequence of a native EPSPS from soybean (*Glycine max*) including the chloroplast transit peptide sequence.

SEQ ID NO:14 is an amino acid sequence of a native EPSPS from wheat (*Triticum aestivum*) including the chloroplast transit peptide sequence.

SEQ ID NO:15 is an amino acid sequence of a native EPSPS from *Brassica rapa* including the chloroplast transit peptide sequence.

SEQ ID NO:16 is an amino acid sequence of a native EPSPS from tomato (*Solanum lycopersicum*) including the chloroplast transit peptide sequence.

SEQ ID NO:17 is an amino acid sequence of a native EPSPS from potato (*Solanum tuberosum*) including the chloroplast transit peptide sequence.

SEQ ID NO:18 is a mutated version of the EPSPS sequence from soybean (SEQ ID NO:13) that contains the 868-H6 mutations.

SEQ ID NO:19 is a mutated version of the EPSPS sequence from wheat (SEQ ID NO:14) that contains the 868-H6 mutations.

SEQ ID NO:20 is a mutated version of the EPSPS sequence from *Brassica rapa* (SEQ ID NO:15) that contains the 868-H6 mutations.

SEQ ID NO:21 is a mutated version of the EPSPS sequence from tomato (SEQ ID NO:16) that contains the 868-H6 mutations.

SEQ ID NO:22 is a mutated version of the EPSPS sequence from potato (SEQ ID NO:17) that contains the 868-H6 mutations.

SEQ ID NO:23 is a mutated version of the EPSPS sequence from sorghum (SEQ ID NO:8) that contains the 123-C1 mutations.

SEQ ID NO:24 is the DNA sequence that encodes the native maize EPSPS and the C-terminal hemagglutinin affinity tag (but not the chloroplast transit peptide).

SEQ ID NO:25 is the DNA sequence that encodes maize EPSPS variant 868-H6 and the C-terminal hemaglutinin affinity tag (but not the chloroplast transit peptide).

SEQ ID NO:26 is the DNA sequence coding for the chloroplast targeting peptide from the *Arabidopsis* EPSPS.

SEQ ID NO:27 is the nucleotide sequence encoding an artificial CTP termed 6H1 (U.S. Pat. No. 7,345,143).

SEQ ID NO:28 is the nucleotide sequence of the native *Arabidopsis* EPSPS promoter (AT1G48860; NCBI GI No. CP002684.1, *Arabidopsis thaliana* chromosome 1, base pairs 18071332 to Ser. No. 18/072,324).

SEQ ID NO:29 is the nucleotide sequence of the *Arabidopsis thaliana* ubiquitin-3 promoter (NCBI GI No. Gen-Bank L05363.1).

SEQ ID NO:30 is the nucleotide sequence of the promoter of the *Arabidopsis thaliana* ubiquitin-10 (UBQ10) promoter.

SEQ ID NO:31 is the sequence of polynucleotide coding for the hemagglutinin affinity tag.

SEQ ID NO:32 is the nucleotide sequence of a phaseolin terminator.

SEQ ID NO:33 is the DNA sequence encoding the maize EPSPS variant C1 and the C-terminal hemagglutinin affinity tag (but not the chloroplast transit peptide).

SEQ ID NO:34 is the DNA sequence encoding the maize EPSPS variant C2 and the C-terminal hemagglutinin affinity tag (but not the chloroplast transit peptide).

DETAILED DESCRIPTION

I. Compositions

A. EPSP Synthase Polynucleotides and Polypeptides

Various methods and compositions are provided which employ polynucleotides and polypeptides having EPSP synthase (EPSPS) activity. Such EPSPS polypeptides include those that encode plant EPSPS polypeptides that comprise G102A and at least one or more amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS polypeptide comprises a sequence that is at least 90% identical to SEQ ID NO:2.

In some embodiments, the polynucleotides encode plant EPSPS polypeptides that comprise G102A and at least two or more, three or more, or four or more amino acid mutations selected from the group consisting of (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the plant EPSPS polypeptide comprises a sequence that is at least 90% identical to SEQ ID NO:2.

In other embodiments, the polynucleotide encodes a plant EPSPS polypeptide that comprises A4W, H54M, L98C, G102A, K173R, I208L, K243E, E302S, T361S, E391P, D402G, A416G, V438R, S440R, T441Q, and F442V (the mutations present in clone 771-C2). In still other embodiments, the polynucleotide encodes a plant EPSPS polypeptide that comprises A2R, A4W, A72Q, K84R, L98C, G102A, I208L, T279A, E302S, T361S, E391G, D402G, A416G, V438R, and T441Q (the mutations present in clone 868-H6). In still other embodiments, the polynucleotide encodes a plant EPSPS polypeptide that comprises A2R, A4W, K84R, L98C, G102A, I208L, K243E, E391P, and D402G (the mutations present in clone 123-C1). In still other embodiments, the polynucleotide encodes the plant EPSPS polypeptide set forth in SEQ ID NO:4, SEQ ID NO:5, or SEQ ID NO:6 which represent the amino acid sequences of maize EPSPS polypeptides encoded by the nucleotide sequences present in 771-C2, 868-H6, and 123-C1, respectively.

The EPSPS polypeptides and active variants and fragments thereof disclosed herein may have improved catalytic capacity in the presence of glyphosate when compared to previously identified EPSPS polypeptides. The parameter that best indicates the fitness of this trait in vivo is $k_{cat}/K_M*K_I$. The EPSPS polypeptides disclosed herein can have an increased $k_{cat}/K_M*K_I$, when compared to previously known EPSPS enzymes. By "increase" is intended any statistically significant increase when compared to an appropriate control. In some embodiments, an appropriate control is a previously known EPSPS sequence, such as that set forth in SEQ ID NO:2 (maize), SEQ ID NO:7 (rice), SEQ ID NO:8 (sorghum), SEQ ID NO:9 (sunflower), SEQ ID NO:13 (soybean), SEQ ID NO:14 (wheat), SEQ ID NO:15 (Brassica rapa), SEQ ID NO:16 (tomato), or SEQ ID NO:17 (potato). In some embodiments, the increase in the $k_{cat}/K_M*K_I$ when compared to SEQ ID NO:2, 7, 8 9, 13, 14, 15, 16, or 17 can comprise about a 150, 200, 250, 300, 350, 400, 450, 500, 550, 600, 650, 700, 750, 800-fold or greater increase. In still further embodiments, $k_{cat}/K_M*K_I$ may include, for example, a $k_{cat}/K_M*K_I$ of more than about 2000, 2500, 3000, 3500, 4000, 4500, 5000, 5500, 6000, 6500, 7000, 7500, 8000, 8500, 9000, 9500, 10000, or more. The $k_{cat}/K_M*K_I$ for the wild-type maize EPSPS is 11.8, while the $k_{cat}/K_M*K_I$ of an EPSPS enzyme comprising 103I, 107S, and 445G is 2254.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For purposes of this disclosure, "isolated" or "recombinant" when used to refer to nucleic acid molecules excludes isolated unmodified chromosomes. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the disclosure or a biologically active portion thereof is recombinantly produced, optimally culture medium represents less than about 30%, 20%, 10%, 5%, or 1% (by dry weight) of chemical precursors or non-protein-of-interest chemicals.

As used herein, a "recombinant" polynucleotide comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by the deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence.

A "recombinant polypeptide" comprises a combination of two or more chemically linked amino acid segments which are not found directly joined in nature. In specific embodiments, the recombinant polypeptide comprises an additional chemically linked amino acid segment that is located either at the N-terminal, C-terminal or internal to the recombinant polypeptide. Alternatively, the chemically-linked amino acid segment of the recombinant polypeptide can be formed by deletion of at least one amino acid. The additional chemically linked amino acid segment or the deleted chemically linked amino acid segment can be of any length, including for example, 1, 2, 3, 4, 5, 6, 7, 8, 9, 10, 15, 20 or amino acids.

B. Active Fragments and Variants of EPSPS Sequences

Methods and compositions are provided which employ polynucleotides and polypeptides having EPSPS activity. Moreover, any given variant or fragment of an EPSPS sequence may further comprise an improved catalytic capacity in the presence of the inhibitor glyphosate when compared to an appropriate control.

i. Polynucleotide and Polypeptide Fragments

Fragments and variants of the EPSPS polynucleotides and polypeptides provided herein are also encompassed by the present disclosure. By "fragment" is intended a portion of the polynucleotide or a portion of the amino acid sequence and hence protein encoded thereby. Fragments of a polynucleotide may encode protein fragments that retain EPSPS activity, and in specific embodiments, can further comprise an improved property such as improved catalytic capacity in the presence of glyphosate. Alternatively, fragments of a polynucleotide that are useful as hybridization probes or PCR primers generally do not encode fragment proteins retaining biological activity. In specific embodiments, a fragment of a recombinant polynucleotide or a recombinant polynucleotide construct comprises at least one junction of the two or more chemically linked or operably linked nucleic acid segments which are not found directly joined in nature. Thus, fragments of a nucleotide sequence may range from at least about 20 nucleotides, about 50 nucleotides, about 100 nucleotides, about 200 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides, and up to the full-length polynucleotide encoding the EPSPS polypeptides. A fragment of an EPSPS polynucleotide that encodes a biologically active portion of an EPSPS protein of the disclosure will encode at least 25, 50, 75, 100, 125, 150, 175, 200, 225, 250, 275, 300, 325, 350, 375, 400, or 425 amino acids, or up to the total number of amino acids present in a full-length EPSPS polypeptide.

Thus, a fragment of an EPSPS polynucleotide may encode a biologically active portion of an EPSPS polypeptide, or it may be a fragment that can be used as a hybridization probe or PCR primer using methods disclosed below. A biologically active portion of an EPSPS polypeptide can be prepared by isolating a portion of one of the EPSPS polynucleotides, expressing the encoded portion of the EPSPS polypeptides (e.g., by recombinant expression in vitro), and assessing the activity of the EPSPS portion of the EPSPS protein. Polynucleotides that are fragments of a EPSPS nucleotide sequence comprise at least 20, 50, 100, 200, 300, 400, 500, 600, 700, 800, 900, 1000, 1100, 1200, or 1300 contiguous nucleotides, or up to the number of nucleotides present in a full-length EPSPS polynucleotide disclosed herein.

Fragments of a polypeptide may encode protein fragments that retain EPSPS activity, and in specific embodiments, can further comprise an improved catalytic capacity in the presence of glyphosate when compared to an appropriate control. A fragment of a EPSPS polypeptide disclosed herein will encode at least 25, 50, 75, 100, 125, 150, 175, 200, 225, 250, 275, 300, 325, 350, 375, 400, or 425 contiguous amino acids, or up to the total number of amino acids present in a full-length EPSPS polypeptide. In specific embodiments, such polypeptide fragments are active fragments, and in still other embodiments, the polypeptide fragment comprises a recombinant polypeptide fragment. As used herein, a fragment of a recombinant polypeptide comprises at least one of a combination of two or more chemically linked amino acid segments which are not found directly joined in nature.

ii. Polynucleotide and Polypeptide Variants

"Variant" protein is intended to mean a protein derived from the protein by deletion (i.e., truncation at the 5' and/or 3' end) and/or a deletion or addition of one or more amino acids at one or more internal sites in the native protein and/or substitution of one or more amino acids at one or more sites in the native protein. Variant proteins encompassed are biologically active, that is they continue to possess the desired biological activity, that is, have EPSPS activity. Moreover, any given variant or fragment may further comprise an improved specificity for glyphosate when compared to an appropriate control resulting in decreased non-specific acetylation of, e.g. an amino acid such as aspartate. Such variants may result from, for example, genetic polymorphism or from human manipulation.

"Variants" is intended to mean substantially similar sequences. For polynucleotides, a variant comprises a polynucleotide having a deletion (i.e., truncations) at the 5' and/or 3' end and/or a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the EPSPS polypeptides provided herein. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis or gene synthesis but which still encode an EPSPS polypeptide.

Biologically active variants of an EPSPS polypeptide disclosed herein (and the polynucleotide encoding the same) will have at least about 85%, 90%, 91%, 92%, 93%, 93.5%, 94%, 94.5%, 95%, 95.5%, 96%, 96.5%, 97%, 97.5%, 98%, 98.5%, 99%, 99.5%, or more sequence identity to the polypeptide of any one of SEQ ID NO:1, 2, 4, 5, 6, 7, 8, 9, and 10, as determined by sequence alignment programs and parameters described elsewhere herein.

The EPSPS polypeptide and the active variants and fragments thereof may be altered in various ways including amino acid substitutions, deletions, truncations, and insertions. Methods for such manipulations are generally known in the art. For example, amino acid sequence variants and fragments of the EPSPS proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The mutations that will be made in the DNA encoding the variant must not place the sequence out of reading frame and optimally will not create complementary regions that could produce secondary mRNA structure. See, EP Patent Application Publication No. 75,444.

C. Sequence Comparisons

The following terms are used to describe the sequence relationships between two or more polynucleotides or polypeptides.

As used herein, "reference sequence" is a predetermined sequence used as a basis for sequence comparison. A reference sequence may be a subset or the entirety of a specified sequence; for example, as a segment of a full-length cDNA or gene sequence, or the complete cDNA or gene sequence or protein sequence.

As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acids in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTP for proteins) can be used. Alignment may also be performed manually by inspection.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

D. Plants and Other Host Cells of Interest

Further provided are engineered host cells that are transduced (transformed or transfected) with one or more EPSPS sequences or active variants or fragments thereof. The EPSPS polypeptides or variants and fragments thereof can be expressed in any organism, including in non-animal cells such as plants, yeast, fungi, bacteria and the like. Details regarding non-animal cell culture can be found in Payne et al. (1992) *Plant Cell and Tissue Culture in Liquid Systems*, John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin, Heidelberg, New York); and Atlas and Parks (eds.) *The Handbook of Microbiological Media* (1993) CRC Press, Boca Raton, Fla.

Plants, plant cells, plant parts and seeds, and grain having the EPSPS sequences disclosed herein are also provided. In specific embodiments, the plants and/or plant parts have stably incorporated at least one heterologous EPSPS polypeptide disclosed herein or an active variant or fragment thereof. In addition, the plants or organism of interest can comprise multiple EPSPS polynucleotides (i.e., at least 1, 2, 3, 4, 5, 6 or more).

In specific embodiments, the heterologous plant EPSPS polynucleotide in the plant or plant part is operably linked to a heterologous regulatory element, such as but not limited to a constitutive, tissue-preferred, or other promoter for expression in plants or a constitutive enhancer.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the disclosure, provided that these parts comprise the introduced polynucleotides.

The EPSPS sequences and active variants and fragments thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. raga, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, conifers, turf grasses (including cool seasonal grasses and warm seasonal grasses).

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tu/ipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing that which is disclosed include, for example, pines such as loblolly pine (*Pinus taeda*), slash pine (*Pinus elliotil*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and *Eucalyptus*. In specific embodiments, plants of the present disclosure are crop plants (for example, corn, alfalfa, sunflower, *Brassica*, soybean, cotton, safflower, peanut, *sorghum*, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

Additional host cells of interest can be a eukaryotic cell, an animal cell, a protoplast, a tissue culture cell, prokaryotic cell, a bacterial cell, such as *E. coli, B. subtilis, Streptomyces, Salmonella typhimurium*, a gram positive bacteria, a purple bacteria, a green sulfur bacteria, a green non-sulfur bacteria, a cyanobacteria, a spirochetes, a thermatogale, a flavobacteria, bacteroides; a fungal cell, such as *Saccharomyces cerevisiae, Pichia pastoris*, and *Neurospora crassa*; an insect cell such as *Drosophila* and *Spodoptera frugiperda*; a mammalian cell such as CHO, COS, BHK, HEK 293 or Bowes melanoma, archaebacteria (i.e., Korarchaeota, Thermoproteus, Pyrodictium, Thermococcales, Methanogens, Archaeoglobus, and extreme Halophiles) and others.

For example, in some embodiments, glyphosate tolerant maize plants are provided, in which the glyphosate tolerant maize plants express an endogenous EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the endogenous plant EPSPS gene encodes a polypeptide comprising a sequence that is at least 90% identical to SEQ ID NO:2. Further, the glyphosate tolerant maize plant may express an endogenous EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the endogenous plant EPSPS gene encodes a polypeptide comprising a sequence that is at least 90% identical to SEQ ID NO:2. Still further, the glyphosate tolerant maize plant may express an endogenous EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G; or has the sequence set forth in SEQ ID NO:4, SEQ ID NO:5, or SEQ ID NO:6.

For example, in some embodiments, glyphosate tolerant sunflower plants are provided, in which the glyphosate tolerant sunflower plants express an EPSPS polypeptide that has G102A and at least one amino acid mutation selected from the group consisting of: a) A2R, (b) A4W, (c) H54M, (d) A72R, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:9. Further, the glyphosate tolerant sunflower plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:9. Still further, the glyphosate tolerant sunflower plant may express an endogenous EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant sunflower plant may express an EPSPS polypeptide having the sequence set forth in SEQ ID NO:10.

For example, in some embodiments, glyphosate tolerant rice plants are provided, in which the glyphosate tolerant rice plants express an EPSPS polypeptide that has G102A and at least one amino acid mutation selected from the group consisting of: a) A2R, (b) A4W, (c) H54M, (d) A72Q, (e)

K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:7. Further, the glyphosate tolerant rice plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:7. Still further, the glyphosate tolerant rice plant may express an EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant rice plant may express the EPSPS polypeptide set forth in SEQ ID NO:11.

For example, in some embodiments, glyphosate tolerant *sorghum* plants are provided, in which the glyphosate tolerant *sorghum* plants express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:8. Further, the glyphosate tolerant *sorghum* plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:8. Still further, the glyphosate tolerant *sorghum* plant may express an EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant *sorghum* plant may express an EPSPS polypeptide having the sequence set forth in SEQ ID NO:12.

For example, in some embodiments, glyphosate tolerant soybean plants are provided, in which the glyphosate tolerant soybean plants express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:13. Further, the glyphosate tolerant soybean plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:13. Still further, the glyphosate tolerant soybean plant may express an EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant soybean plant may express a plant EPSPS polypeptide having the sequence set forth in SEQ ID NO:18. For example, in some embodiments, glyphosate tolerant wheat plants are provided, in which the glyphosate tolerant wheat plants express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:14. Further, the glyphosate tolerant wheat plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:14. Still further, the glyphosate tolerant wheat plant may express an EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant wheat plant may express a plant EPSPS polypeptide having the sequence set forth in SEQ ID NO:19.

For example, in some embodiments, glyphosate tolerant *Brassica rapa* plants are provided, in which the glyphosate tolerant *Brassica rapa* plants express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m)

E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:15. Further, the glyphosate tolerant *Brassica rapa* plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:15. Still further, the glyphosate tolerant *Brassica rapa* plant may express an EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant *Brassica rapa* plant may express a plant EPSPS polypeptide having the sequence set forth in SEQ ID NO:20.

For example, in some embodiments, glyphosate tolerant tomato plants are provided, in which the glyphosate tolerant tomato plants express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:17. Further, the glyphosate tolerant tomato plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:17. Still further, the glyphosate tolerant tomato plant may express an EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant tomato plant may express a plant EPSPS polypeptide having the sequence set forth in SEQ ID NO:21.

For example, in some embodiments, glyphosate tolerant potato plants are provided, in which the glyphosate tolerant potato plants express an EPSPS polypeptide that has G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the analogous amino acid position set forth in SEQ ID NO:1 and wherein the plant EPSPS gene encodes a polypeptide comprising a sequence that is at least 90% identical to SEQ ID NO:18. Further, the glyphosate tolerant potato plant may express an EPSPS polypeptide that has G102A and at least two, at least three, or at least four of the amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS gene encodes a polypeptide comprising a sequence that is at least 90% identical to SEQ ID NO:18. Still further, the glyphosate tolerant potato plant may express an EPSPS polypeptide that has: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. A glyphosate tolerant potato plant may express a plant EPSPS polypeptide having the sequence set forth in SEQ ID NO:22.

E. Polynucleotide Constructs

The use of the term "polynucleotide" is not intended to limit a polynucleotide of the disclosure to a polynucleotide comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the disclosure also encompass all forms of sequences including, but not limited to, single-stranded forms, double-stranded forms, hairpins, stem-and-loop structures, and the like.

For example, a polynucleotide construct may be a recombinant DNA construct. A "recombinant DNA construct" comprises two or more operably linked DNA segments which are not found operably linked in nature. Non-limiting examples of recombinant DNA constructs include a polynucleotide of interest or active variant or fragment thereof operably linked to heterologous sequences which aid in the expression, autologous replication, and/or genomic insertion of the sequence of interest. Such heterologous and operably linked sequences include, for example, promoters, termination sequences, enhancers, etc., or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

The EPSPS polynucleotides disclosed herein can be provided in expression cassettes for expression in the plant of interest or any organism of interest. The cassette can include 5' and 3' regulatory sequences operably linked to an EPSPS polynucleotide or active variant or fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the EPSPS polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), a EPSPS polynucleotide or active variant or fragment thereof, and a transcriptional and translational termination region (i.e., termination region) functional in plants. The regulatory regions (i.e., promoters, transcriptional regulatory regions, and translational termination regions) and/or the EPSPS polynucleotide or active variant or fragment thereof may be native/analogous to the host cell or to each other. Alternatively, the regulatory regions and/or the EPSPS polynucleotide of or active variant or fragment thereof may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region or active variant or fragment thereof, may be native with the plant host, or may be derived from another source (i.e., foreign or heterologous) to the promoter, the EPSPS polynucleotide or active fragment or variant thereof, the plant host, or any combination thereof.

The expression cassettes may additionally contain 5' leader sequences. Such leader sequences can act to enhance translation. Translation leaders are known in the art and include viral translational leader sequences.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various EPSPS sequences disclosed herein, including the native promoter of the polynucleotide sequence of interest. The promoters can be selected based on the desired outcome. Such promoters include, for example, constitutive, inducible, tissue-preferred, or other promoters for expression in plants or in any organism of interest.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Synthetic promoters can be used to express EPSPS sequences or biologically active variants and fragments thereof. Synthetic promoters include for example a combination of one or more heterologous regulatory elements.

In another aspect, the EPSPS sequences disclosed herein or active variants or fragments thereof can also be used as a selectable marker gene. In this embodiment, the presence of the EPSPS polynucleotide in a cell or organism confers upon the cell or organism the detectable phenotypic trait of glyphosate resistance, thereby allowing one to select for cells or organisms that have been transformed with a gene of interest linked to the EPSPS polynucleotide. Thus, for example, the EPSPS polynucleotide can be introduced into a nucleic acid construct, e.g., a vector, thereby allowing for the identification of a host (e.g., a cell or transgenic plant) containing the nucleic acid construct by growing the host in the presence of glyphosate and selecting for the ability to survive and/or grow at a rate that is discernibly greater than a host lacking the nucleic acid construct would survive or grow. An EPSPS polynucleotide can be used as a selectable marker in a wide variety of hosts that are sensitive to glyphosate, including plants, most bacteria (including *E. coli*), actinomycetes, yeasts, algae and fungi.

In specific embodiments, the EPSPS polypeptides and active variants and fragments thereof, and polynucleotides encoding the same, further comprise a chloroplast transit peptide. As used herein, the term "chloroplast transit peptide" will be abbreviated "CTP" and refers to the N-terminal portion of a chloroplast precursor protein that directs the latter into chloroplasts and is subsequently cleaved off by the chloroplast processing protease. When a CTP is operably linked to the N-terminus of a polypeptide, the polypeptide is translocated into the chloroplast. Removal of the CTP from a native protein reduces or abolishes the ability of the native protein from being transported into the chloroplast. An operably linked chloroplast transit peptide is found at the N-terminus of the protein to be targeted to the chloroplast and is located upstream and immediately adjacent to the transit peptide cleavage site that separates the transit peptide from the mature protein to be targeted to the chloroplast.

The term "chloroplast transit peptide cleavage site" refers to a site between two amino acids in a chloroplast-targeting sequence at which the chloroplast processing protease acts. Chloroplast transit peptides target the desired protein to the chloroplast and can facilitate the proteins translocation into the organelle. This is accompanied by the cleavage of the transit peptide from the mature polypeptide or protein at the appropriate transit peptide cleavage site by a chloroplast processing protease, native to the chloroplast. Accordingly, a chloroplast transit peptide further comprises a suitable cleavage site for the correct processing of the pre-protein to the mature polypeptide contained within the chloroplast.

As used herein, a "heterologous" CTP comprises a transit peptide sequence which is foreign to the polypeptide it is operably linked to. Such heterologous chloroplast transit peptides are known, including but not limited to those derived from *Pisum* (JP 1986224990; E00977), carrot (Luo et al. (1997) *Plant Mol. Biol.,* 33 (4), 709-722 (Z33383), *Nicotiana* (Bowler et al., EP 0359617; A09029), *Oryza* (de Pater et al. (1990) *Plant Mol. Biol.,* 15 (3), 399-406 (X51911), as well as synthetic sequences such as those provided in EP 0189707; U.S. Pat. Nos. 5,728,925; 5,717,084 (A10396 and A10398). In one embodiment, the heterologous chloroplast transit peptide is from the ribulose-1,5-bisphosphate carboxylase (Rubisco) small subunit precursor protein isolated from any plant. The Rubisco small subunit is well characterized from a variety of plants and the transit peptide from any of them will be suitable for use disclosed herein. See for example, *Physcomitrella* (Quatrano et al., AW599738); Lotus (Poulsen et al., AW428760); *Citrullus* (J. S. Shin, A1563240); *Nicotiana* (Appleby et al. (1997) *Heredity* 79(6), 557-563); alfalfa (Khoudi et al. (1997) *Gene,* 197(1/2), 343-351); potato and tomato (Fritz et al. (1993) Gene, 137(2), 271-4); wheat (Galili et al. (1991) *Theor. Appl. Genet.* 81(1), 98-104); and rice (Xie et al. (1987) Sci. Sin., Ser. B (Engl. Ed.), 30(7), 706-19). For example, transit peptides may be derived from the Rubisco small subunit isolated from plants including but not limited to, soybean, rapeseed, sunflower, cotton, corn, tobacco, alfalfa, wheat, barley, oats, *sorghum*, rice, *Arabidopsis*, sugar beet, sugar cane, canola, millet, beans, peas, rye, flax, and forage grasses. Preferred for use in the present disclosure is the Rubisco small subunit precursor protein from, for example, *Arabidopsis* or tobacco.

F. Stacking Other Traits of Interest

In some embodiments, the EPSPS polynucleotides or active variants and fragments thereof disclosed herein are engineered into a molecular stack. Thus, the various host cells, plants, plant cells and seeds disclosed herein can further comprise one or more traits of interest, and in more specific embodiments, the host cell, plant, plant part or plant cell is stacked with any combination of polynucleotide sequences of interest in order to create plants with a desired combination of traits. As used herein, the term "stacked" includes having the multiple traits present in the same plant or organism of interest. In one non-limiting example, "stacked traits" comprise a molecular stack where the sequences are physically adjacent to each other. A trait, as used herein, refers to the phenotype derived from a particular sequence or groups of sequences. In one embodiment, the molecular stack comprises at least one additional polynucleotide that also confers tolerance to at least one sequence that confers tolerance to glyphosate by the same and/or different mechanism and/or at least one additional polynucleotide that confers tolerance to a second herbicide.

Thus, in one embodiment, the host cells, plants, plant cells or plant part having the EPSPS polynucleotide or active variants or fragments thereof disclosed herein is stacked with at least one other EPSPS sequence. Such EPSPS sequence include the EPSPS sequence and variants and fragment thereof disclosed herein, as well as other EPSPS sequences, which include but are not limited to, the EPSPS sequences set forth in WO02/36782, US Publication 2004/0082770 and WO 2005/012515, U.S. Pat. Nos. 7,462,481, 7,405,074, each of which is herein incorporated by reference.

The mechanism of glyphosate tolerance produced by the EPSPS sequences disclosed herein may be combined with other modes of herbicide resistance to provide host cells, plants, plant explants and plant cells that are tolerant to glyphosate and one or more other herbicides. For instance, the mechanism of glyphosate tolerance conferred by EPSPS may be combined with other modes of glyphosate tolerance known in the art. In other embodiments, the plant or plant cell or plant part having the EPSPS sequence or an active variant or fragment thereof may be stacked with, for example, one or more sequences that confer tolerance to: an ALS inhibitor; an HPPD inhibitor; 2,4-D; other phenoxy auxin herbicides; aryloxyphenoxypropionate herbicides; dicamba; glutamine synthetase (GS); glufosinate herbicides; herbicides which target the protox enzyme (also referred to as "protox inhibitors").

The plant or plant cell or plant part having the EPSPS sequence or an active variant or fragment thereof can also be combined with at least one other trait to produce plants that further comprise a variety of desired trait combinations. For instance, the plant or plant cell or plant part having the EPSPS sequence or an active variant or fragment thereof may be stacked with polynucleotides encoding polypeptides having pesticidal and/or insecticidal activity, or a plant or plant cell or plant part having the EPSPS sequence or an active variant or fragment thereof may be combined with a plant disease resistance gene.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Any plant having at EPSPS sequence disclosed herein or an active variant or fragment thereof can be used to make a food or a feed product. Such methods comprise obtaining a plant, explant, seed, plant cell, or cell comprising the EPSPS sequence or active variant or fragment thereof and processing the plant, explant, seed, plant cell, or cell to produce a food or feed product.

II. Methods of Use

A. Methods of Generating Glyphosate Tolerant Plants

The terms "glyphosate tolerance" and "glyphosate resistance" are used interchangeably herein.

i. Introducing

Various methods can be used to introduce a sequence of interest into a host cell, plant or plant part. "Introducing" is intended to mean presenting to the host cell, plant, plant cell or plant part the polynucleotide or polypeptide in such a manner that the sequence gains access to the interior of a cell of the plant or organism. The methods of the disclosure do not depend on a particular method for introducing a sequence into an organism or a plant or plant part, only that the polynucleotide or polypeptides gains access to the interior of at least one cell of the organism or the plant. Methods for introducing polynucleotide or polypeptides into various organisms, including plants, are known in the art including, but not limited to, stable transformation methods, transient transformation methods, and virus-mediated methods.

"Stable transformation" is intended to mean that the nucleotide construct introduced into a plant integrates into the genome of the plant or organism of interest and is capable of being inherited by the progeny thereof. "Transient transformation" is intended to mean that a polynucleotide is introduced into the plant or organism of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the EPSPS sequences or active variants or fragments thereof can be provided to a plant using a variety of transient transformation methods. Such transient transformation methods include, but are not limited to, the introduction of the EPSPS protein or active variants and fragments thereof directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107: 775-784, all of which are herein incorporated by reference.

In other embodiments, the EPSPS polynucleotide disclosed herein or active variants and fragments thereof may be introduced into plants by contacting plants with a virus or viral nucleic acids. Generally, such methods involve incorporating a nucleotide construct of the disclosure within a DNA or RNA molecule. It is recognized that the EPSPS sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide disclosed herein can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein, for example, as part of an expression cassette, stably incorporated into their genome.

Transformed plant cells which are derived by plant transformation techniques, including those discussed above, can be cultured to regenerate a whole plant which possesses the transformed genotype (i.e., a EPSPS polynucleotide), and thus the desired phenotype, such as acquired resistance (i.e., tolerance) to glyphosate or a glyphosate analog. For transformation and regeneration of maize see, Gordon-Kamm et al., *The Plant Cell*, 2:603-618 (1990). Plant regeneration from cultured protoplasts is described in Evans et al. (1983) *Protoplasts Isolation and Culture, Handbook of Plant Cell Culture*, pp 124-176, Macmillan Publishing Company, New York; and Binding (1985) Regeneration of Plants, *Plant Protoplasts* pp 21-73, CRC Press, Boca Raton. Regeneration can also be obtained from plant callus, explants, organs, or parts thereof. Such regeneration techniques are described generally in Klee et al. (1987) *Ann Rev of Plant Phys* 38:467. See also, e.g., Payne and Gamborg.

One of skill will recognize that after the expression cassette containing the EPSPS gene is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included, provided that these parts comprise cells comprising the EPSPS nucleic acid. Progeny and variants, and mutants of the regenerated plants are also included, provided that these parts comprise the introduced nucleic acid sequences.

In one embodiment, a homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

Animal and lower eukaryotic (e.g., yeast) host cells are competent or rendered competent for transfection by various means. There are several well-known methods of introducing DNA into animal cells. These methods include: calcium phosphate precipitation; fusion of the recipient cells with bacterial protoplasts containing the DNA; treatment of the recipient cells with liposomes containing the DNA; DEAE dextran; electroporation; biolistics; and micro-injection of the DNA directly into the cells. The transfected cells are cultured by means well known in the art. See, Kuchler, R. J., *Biochemical Methods in Cell Culture and Virology*, Dowden, Hutchinson and Ross, Inc. (1977).

In some embodiments, the methods comprise introducing by way of expressing in a regenerable plant cell a recombinant DNA construct comprising a polynucleotide operably linked to at least one regulatory sequence, wherein the polynucleotide encodes a plant EPSPS polypeptide that comprises G102A and at least one amino acid mutation selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the plant EPSPS polypeptide comprises a sequence that is at least 90% identical to SEQ ID NO:2; and generating a glyphosate tolerant plant that comprises in its genome the recombinant DNA construct. In some embodiments, the methods include expressing in a plant cell a recombinant DNA construct comprising a polynucleotide encoding a plant EPSPS polypeptide comprising G102A and at least two, at least three, or at least four amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the plant EPSPS polypeptide comprises a sequence that is at least 90% identical to SEQ ID NO:2.

The recombinant DNA may comprise: (a) a polynucleotide that encodes a plant EPSPS polypeptide that comprises A4W, H54M, L98C, G102A, K173R, I208L, K243E, E302S, T361S, E391P, D402G, A416G, V438R, S440R, T441Q, and F442V; (b) a polynucleotide that encodes a plant EPSPS polypeptide that comprises A2R, A4W, A72Q, K84R, L98C, G102A, I208L, T279A, E302S, T361S, E391G, D402G, A416G, V438R, and T441Q; or (c) a polynucleotide that encodes a plant EPSPS polypeptide that comprises A2R, A4W, K84R, L98C, G102A, I208L, K243E, E391P, and D402G. The recombinant DNA may also comprise a polynucleotide that encodes the plant EPSPS polypeptide set forth in SEQ ID NO:4, SEQ ID NO:5, or SEQ ID NO:6.

ii. Modifying

In general, methods to modify or alter the host genomic DNA are available. For example, a pre-existing or endogenous EPSPS sequence in a host plant can be modified or altered in a site-specific fashion using one or more site-specific engineering systems. This includes altering the host DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" or engineered endonucleases such as meganucleases produced to modify plant genomes (see e.g., WO 2009/114321; Gao et al. (2010) *Plant Journal* 1:176-187). Another site-directed engineering is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. A transcription activator-like (TAL) effector-DNA modifying enzyme (TALE or TALEN) is also used to engineer changes in plant genome. See e.g., US20110145940, Cermak et al., (2011) *Nucleic Acids Res.* 39(12) and Boch et al., (2009), *Science* 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), *Plant Methods* 9: 39; The CRISPR/Cas system allows targeted cleavage of genomic DNA guided by a customizable small noncoding RNA.

For instance, an endogenous plant EPSPS gene in a plant cell may be modified to encode a glyphosate tolerant EPSPS protein that comprises G102A and at least one amino acid mutation selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the endogenous plant EPSPS gene encodes a polypeptide comprising a sequence that is at least 90% identical to SEQ ID NO:2. A glyphosate tolerant plant may be grown from the plant cell. The modified endogenous plant EPSPS gene may encode a glyphosate tolerant EPSPS protein that comprises G102A and at least two, at least three, or at least four of the amino acid mutations selected from the group consisting of: (a) A2R, (b) A4W, (c) H54M, (d) A72Q, (e) K84R, (f) L98C, (g)

K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid position set forth in SEQ ID NO:1 and wherein the endogenous plant EPSPS gene encodes a polypeptide comprising a sequence that is at least 90% identical to SEQ ID NO:2. The modified endogenous plant EPSPS gene may encode a glyphosate tolerant EPSPS protein that comprises: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. The modified endogenous plant EPSPS gene may encode a glyphosate tolerant EPSPS protein that comprises the plant EPSPS polypeptide set forth in SEQ ID NO:4, SEQ ID NO:5, or SEQ ID NO:6.

The endogenous plant EPSPS gene may be modified by a CRISPR/Cas guide RNA-mediated system, a Zn-finger nuclease-mediated system, a meganuclease-mediated system, an oligonucleobase-mediated system, or any gene modification system known to one of ordinary skill in the art.

Moreover, for the purposes herein, an endogenous plant EPSPS gene includes coding DNA and genomic DNA within and surrounding the coding DNA, such as for example, the promoter, intron, and terminator sequences.

In some embodiments, the CRISPR/Cas guide RNA-mediated system is used to modify the endogenous plant EPSPS gene. CRISPRs are arrays of clustered, regularly interspaced, short palindromic repeats within the bacterial genome. The recent discovery of CRISPR-associated protein 9 nuclease (Cas9) from *Streptococcus pyogenes* presents the possibility of introducing mutations into a native gene (Sander and Joung, 2014). To introduce double strand breaks into the target gene, Cas9 is guided to the target gene DNA by normal base-pairing with an engineered RNA. Following double-strand break, the desired mutation(s) in EPSPS can be introduced from an engineered template through the homology-directed repair process. EPSPS coded by modified genes will be under the control of the native promoter. Thus, all tissues will express the enzyme according to their native spatial and temporal program, a condition that may confer an advantage over transgenic expression in providing appropriate catalytic capacity.

As used herein, the term "guide polynucleotide", refers to a polynucleotide sequence that can form a complex with a Cas endonuclease and enables the Cas endonuclease to recognize and optionally cleave a DNA target site. The guide polynucleotide can include a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, Phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. In some embodiment of this disclosure, the guide polynucleotide does not solely comprise ribonucleic acids (RNAs). A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. In one embodiment, the size of the fragment of the crRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site.

One aspect of using a single guide polynucleotide versus a duplex guide polynucleotide is that only one expression cassette needs to be made to express the single guide polynucleotide.

The term "variable targeting domain" or "VT domain" is used interchangeably herein and refers to a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence (see for example modifications described herein), or any combination thereof.

The term "Cas endonuclease recognition domain" or "CER domain" of a guide polynucleotide is used interchangeably herein and refers to a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In one embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In one embodiment of the disclosure, the composition comprises a guide polynucleotide comprising: (i) a first nucleotide sequence domain (VT domain) that is complementary to a nucleotide sequence in a target DNA; and, (ii) a second nucleotide sequence domain (CER domain) that interacts with a Cas endonuclease, wherein the first nucleotide sequence domain and the second nucleotide sequence domain are composed of deoxyribonucleic acids (DNA), ribonucleic acids (RNA), or a combination thereof. The % complementation between the first nucleotide sequence domain (Variable Targeting domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 950/o, 96%, 97%, 98%, 99% or 100%.

In one embodiment of the disclosure, the first nucleotide sequence domain (VT domain) and the second nucleotide sequence domain (CER domain) of the guide polynucleotide are located on a single molecule. In another embodiment, the second nucleotide sequence domain (Cas Endonuclease Recognition domain) comprises two separate molecules that are capable of hybridizing along a region of complementarity.

In one embodiment, the composition comprises a guide polynucleotide, wherein the first nucleotide sequence domain (VT domain) is a DNA sequence and the second nucleotide sequence domain (CER domain) is selected from the group consisting of a DNA sequence, a RNA sequence, and a combination thereof.

In one embodiment the guide polynucleotide can be introduce into the plant cell directly using any method known to one skilled in the art, such as for example, but not limited to, particle bombardment or topical applications.

When the guide polynucleotide comprises solely of RNA sequences (also referred to as "guide RNA") it can be introduced indirectly by introducing a recombinant DNA molecule comprising the corresponding guide DNA sequence operably linked to a plant specific promoter that is capable of transcribing the guide polynucleotide in said plant cell. The term "corresponding guide DNA" refers to a DNA molecule that is identical to the RNA molecule but has a "T" substituted for each "U" of the RNA molecule.

In some embodiments, the guide polynucleotide is introduced via particle bombardment or *Agrobacterium* transformation of a recombinant DNA construct comprising the corresponding guide DNA operably linked to a plant U6 polymerase III promoter.

The terms "target site", "target sequence", "target DNA", "target locus", "genomic target site", "genomic target sequence", and "genomic target locus" are used interchangeably herein and refer to a polynucleotide sequence in the genome (including chloroplastic and mitochondrial DNA) of a cell at which a double-strand break is induced in the cell genome by a Cas endonuclease. The target site can be an endogenous site in the genome of a cell or organism, or alternatively, the target site can be heterologous to the cell or organism and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a cell or organism and is at the endogenous or native position of that target sequence in the genome of a cell or organism. Cells include, but are not limited to animal, bacterial, fungal, insect, yeast, and plant cells as well as plants and seeds produced by the methods described herein.

In one embodiments, the target site, in association with the particular gene editing system that is being used, can be similar to a DNA recognition site or target site that is specifically recognized and/or bound by a double-strand break inducing agent, such as but not limited to a Zinc Finger endonuclease, a meganuclease, or a TALEN endonuclease.

An "artificial target site" or "artificial target sequence" are used interchangeably herein and refer to a target sequence that has been introduced into the genome of a cell or organism, such as but not limiting to a plant or yeast. Such an artificial target sequence can be identical in sequence to an endogenous or native target sequence in the genome of a cell but be located in a different position (i.e., a non-endogenous or non-native position) in the genome of a cell or organism.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Polynucleotide constructs that provide a guide RNA which targets an endogenous EPSPS gene of a plant cell are provided herein. The polynucleotide construct may further comprise one or more polynucleotide modification templates to generate a modified endogenous EPSPS gene that encodes a plant EPSPS polypeptide that comprises G102A and at least one amino acid mutation selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the endogenous plant EPSPS gene encodes a polypeptide comprising a sequence that is at least 90% identical to SEQ ID NO:2. The modified endogenous EPSPS gene may encode a plant EPSPS polypeptide that comprises G102A and at least two, at least three, or at least four amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid mutation position set forth in SEQ ID NO:1 and wherein the endogenous plant EPSPS gene encodes a polypeptide comprising a sequence that is at least 90% identical to SEQ ID NO:2. The modified endogenous EPSPS gene may encode a plant EPSPS polypeptide that comprises: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. The modified endogenous EPSPS gene may encode a plant EPSPS polypeptide that has the amino acid sequence set forth in SEQ ID NO:4, SEQ ID NO:5, or SEQ ID NO:6.

Methods for producing glyphosate tolerant plants are provided herein in which a guide RNA, one or more polynucleotide modification templates, and one or more Cas endonucleases are provided to a plant cell. The Cas endonuclease(s) introduces a double strand break at an endogenous EPSPS gene in the plant cell, and the polynucleotide modification template(s) is used to generate a modified EPSPS gene that encodes a plant EPSPS polypeptide that comprises G102A and at least one amino acid mutation selected from the group consisting of: a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid mutation position corresponds to the amino acid position set forth in SEQ ID NO:1 and wherein the endogenous plant EPSPS gene encodes a polypeptide comprising a sequence that is at least 90% identical to SEQ ID NO:2. A plant is obtained from the plant cell, and a glyphosate tolerant progeny plant that is void of the guide RNA and Cas endonuclease is generated. The modified endogenous EPSPS gene may encode a plant EPSPS polypeptide that comprises G102A and at least two, at least three, or at least four amino acid mutations selected from the group consisting of: (a) A2R, (b) A4W, (c) H54M, (d) A72Q, (e) K84R, (f) L98C, (g) K173R, (h) I208L, (i) K243E, (j) T279A, (k) E302S, (l) T361S, (m) E391P, (n) E391G, (o) D402G, (p) A416G, (q) V438R, (r) S440R, (s) T441Q, and (t) F442V, wherein each amino acid position corresponds to the amino acid mutation position set forth in SEQ ID NO:1 and wherein the endogenous plant EPSPS gene encodes a polypeptide comprising a sequence that is at least 90% identical to SEQ ID NO:2. The modified endogenous EPSPS gene may encode a plant EPSPS polypeptide that comprises: (a) A4W, H54M, L98C, G102A, K173R, I208L, K243E, E302S, T361S, E391P, D402G, A416G, V438R, S440R, T441Q, and F442V; (b) A2R, A4W, A72Q, K84R, L98C, G102A, I208L, T279A, E302S, T361S, E391G, D402G, A416G, V438R, and T441Q; or (c) A2R, A4W, K84R, L98C, G102A, I208L, K243E, E391P, and D402G. The modified endogenous EPSPS gene may encode a plant EPSPS polypeptide that has the amino acid sequence set forth in SEQ ID NO:4, SEQ ID NO:5, or SEQ ID NO:6.

Polynucleotide modification templates that are used for endogenous modification of a gene through CRISPR/Cas9 gene editing are also provided herein. The polynucleotide modification templates may comprise a partial EPSP synthase (EPSPS) sequence and may further comprise one or more nucleotide mutations that correspond to G102A and to at least one or more amino acid mutations selected from the group consisting of: a) A2R, b) A4W, c) H54M, d) A72Q, e) K84R, f) L98C, g) K173R, h) I208L, i) K243E, j) T279A, k) E302S, l) T361S, m) E391P, n) E391G, o) D402G, p) A416G, q) V438R, r) S440R, s) T441Q, and t) F442V, wherein each amino acid mutation position corresponds to the amino acid position set forth in SEQ ID NO: 1, are also provided.

B. Methods for Increasing Expression and/or Activity Level of at Least One EPSPS Sequence or an Active Variant or Fragment Thereof in a Host Cell of Interest, a Plant or Plant Part Various methods are provided for the expression of an EPSPS sequence or active variant or fragment thereof in a host cell of interest. For example, the host cell of interest is transformed with the EPSPS sequence and the cells are cultured under conditions which allow for the expression of the EPSPS sequence. In some embodiments, the cells are harvested by centrifugation, disrupted by physical or chemical means, and the resulting crude extract retained for further purification. Microbial cells employed in the expression of proteins can be disrupted by any convenient method, including freeze-thaw cycling, sonication, mechanical disruption, or use of cell lysing agents, or other methods, which are well known to those skilled in the art.

As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, $3^{rd}$ Ed., Wiley-Liss, New York and the references cited therein; Doyle and Griffiths (1997) *Mammalian Cell Culture: Essential Techniques* John Wiley and Sons, NY; Humason (1979) *Animal Tissue Techniques*, 4th Ed. W.H. Freeman and Company; and Ricciardelli, et al., (1989) *In vitro Cell Dev. Biol.* 25:1016-1024. For plant cell culture and regeneration see, Payne et al. (1992) *Plant Cell and Tissue Culture in Liquid Systems* John Wiley & Sons, Inc. New York, N.Y.; Gamborg and Phillips (eds.) (1995) s; Fundamental Methods Springer Lab Manual, Springer-Verlag (Berlin, Heidelberg, New York); Jones, ed. (1984) *Plant Gene Transfer and Expression Protocols*, Humana Press, Totowa, N.J.; and *Plant Molecular Biology* (1993) R. R. D. Croy, ed. Bios Scientific Publishers, Oxford, U.K. ISBN 0 12 198370 6. Cell culture media in general are set forth in Atlas and Parks (eds.) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc. (St Louis, Mo.) ("Sigma-LSRCCC") and, e.g., *The Plant Culture Catalogue* and supplement (1997) also from Sigma-Aldrich, Inc. (St Louis, Mo.) ("Sigma-PCCS").

A method for increasing the activity of an EPSPS polypeptide disclosed herein or an active variant or fragment thereof in a plant, plant cell, plant part, explant, and/or seed is provided. In further embodiments, the activity of the EPSPS polypeptide is increased in a plant or plant part by at least 10%, 20%, 30%, 40%, 50%, 60%, 70%, 80%, 90%, 100%, 200%, 500%, 1000%, 5000%, or 10,000% relative to an appropriate control plant, plant part, or cell. In still other embodiments, the activity level of the EPSPS polypeptide in the plant or plant part is increased by 10, 20, 30, 40, 50, 60, 70, 80, 90, 100 fold or more relative to an appropriate control plant, plant part, or cell. Such an increase in the activity of the EPSPS polypeptide in the cell can be achieved in a variety of ways including, for example, by the expression of multiple copies of one or more EPSPS polypeptide, by employing a promoter to drive higher levels of expression of the sequence, or by employing a EPSPS sequence having an increased level of activity.

In specific embodiments, the polypeptide or the EPSPS polynucleotide or active variant or fragment thereof is introduced into the plant, plant cell, explant or plant part. Subsequently, a plant cell having an introduced sequence disclosed herein is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the temporal or spatial expression of polypeptides disclosed herein in the plant. Plant forming conditions are well known in the art and discussed briefly elsewhere herein.

In one embodiment, a method of producing a glyphosate tolerant plant cell is provided and comprises transforming a plant cell with the polynucleotide encoding an EPSPS polypeptide or active variant or fragment thereof. In specific embodiments, the method further comprises selecting a plant cell which is resistant or tolerant to a glyphosate by growing the plant cells in a sufficient concentration of glyphosate, such that the herbicide kills the plant cells which do not comprise the EPSPS polypeptide of interest.

C. Method of Producing Crops and Controlling Weeds

Methods for controlling weeds in an area of cultivation, preventing the development or the appearance of herbicide resistant weeds in an area of cultivation, producing a crop, and increasing crop safety are provided. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc.), a greenhouse, a growth chamber, etc.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 10%, 5%, or 1% of the crop plants are significantly damaged or killed.

Methods provided comprise planting the area of cultivation with a plant having a EPSPS sequence or active variant or fragment thereof disclosed herein or transgenic seed derived therefrom, and in specific embodiments, applying to the crop, seed, weed or area of cultivation thereof an effective amount of a herbicide of interest. It is recognized that the herbicide can be applied before or after the crop is planted in the area of cultivation. Such herbicide applications can include an application of glyphosate.

Accordingly, the term "glyphosate" should be considered to include any herbicidally effective form of N-phosphonomethylglycine (including any salt thereof) and other forms which result in the production of the glyphosate anion in planta.

In specific methods, glyphosate is applied to the plants having the EPSPS sequence or active variant or fragment thereof or their area of cultivation. In specific embodiments, the glyphosate is in the form of a salt, such as, ammonium, isopropylammonium, potassium, sodium (including sesquisodium) or trimesium (alternatively named sulfosate). In still further embodiments, a mixture of a synergistically effective amount of a combination of glyphosate and an ALS inhibitor (such as a sulfonylurea) is applied to the plants or their area of cultivation.

Generally, the effective amount of herbicide applied to the field is sufficient to selectively control the weeds without significantly affecting the crop. In some embodiments, the effective amount of glyphosate applied is about 50 gram acid equivalent/acre to about 2000 gram acid equivalent/acre. It is important to note that it is not necessary for the crop to be totally insensitive to the herbicide, so long as the benefit derived from the inhibition of weeds outweighs any negative impact of the glyphosate or glyphosate analog on the crop or crop plant.

"Weed" as used herein refers to a plant which is not desirable in a particular area. Conversely, a "crop plant" as used herein refers to a plant which is desired in a particular area, such as, for example, a maize or soy plant. Thus, in some embodiments, a weed is a non-crop plant or a non-crop species, while in some embodiments, a weed is a crop species which is sought to be eliminated from a particular area, such as, for example, an inferior and/or non-transgenic soy plant in a field planted with a plant having the EPSPS sequence disclosed herein or an active variant or fragment thereof.

Accordingly, the current disclosure provides methods for selectively controlling weeds in a field containing a crop that involve planting the field with crop seeds or plants which are glyphosate-tolerant as a result of being transformed with a gene encoding a EPSPS disclosed herein or an active variant or fragment thereof, and applying to the crop and weeds in the field a sufficient amount of glyphosate to control the weeds without significantly affecting the crop.

Further provided are methods for controlling weeds in a field and preventing the emergence of glyphosate resistant weeds in a field containing a crop which involve planting the field with crop seeds or plants that are glyphosate tolerant as a result of being transformed with a gene encoding EPSPS and a gene encoding a polypeptide imparting glyphosate tolerance by another mechanism, such as, a glyphosate tolerant glyphosate-N-acetyltransferase and/or a glyphosate-tolerant glyphosate oxido-reductase and applying to the crop and the weeds in the field a sufficient amount of glyphosate to control the weeds without significantly affecting the crop. Various plants that can be used in this method are discussed in detail elsewhere herein.

In further embodiments, the current disclosure provides methods for controlling weeds in a field and preventing the emergence of herbicide resistant weeds in a field containing a crop which involve planting the field with crop seeds or plants that are glyphosate tolerant as a result of being transformed with a gene encoding EPSPS, a gene encoding a polypeptide imparting glyphosate tolerance by another mechanism, such as, a glyphosate tolerant glyphosate-N-acetyltransferase and/or a glyphosate oxido-reductase and a gene encoding a polypeptide imparting tolerance to an additional herbicide, such as, a mutated hydroxyphenylpyruvatedioxygenase, a sulfonylurea-tolerant acetolactate synthase, a sulfonylurea-tolerant acetohydroxy acid synthase, a sulfonamide-tolerant acetolactate synthase, a sulfonamide-tolerant acetohydroxy acid synthase, an imidazolinone-tolerant acetolactate synthase, an imidazolinone-tolerant acetohydroxy acid synthase, a phosphinothricin acetyl transferase and a mutated protoporphyrinogen oxidase and applying to the crop and the weeds in the field a sufficient amount of glyphosate and an additional herbicide, such as, a hydroxyphenylpyruvatedioxygenase inhibitor, sulfonamide, imidazolinone, bialaphos, phosphinothricin, azafenidin, butafenacil, sulfosate, glufosinate, and a protox inhibitor to control the weeds without significantly affecting the crop. Various plants and seeds that can be used in this method are discussed in detail elsewhere herein.

Further provided are methods for controlling weeds in a field and preventing the emergence of herbicide resistant weeds in a field containing a crop which involve planting the field with crop seeds or plants that are glyphosate tolerant as a result of being transformed with a gene encoding an EPSPS and a gene encoding a polypeptide imparting tolerance to an additional herbicide, such as, a mutated hydroxyphenylpyruvatedioxygenase, a sulfonamide-tolerant acetolactate synthase, a sulfonamide-tolerant acetohydroxy acid synthase, an imidazolinone-tolerant acetolactate synthase, an imidazolinone-tolerant acetohydroxy acid synthase, a phosphinothricin acetyl transferase and a mutated protoporphyrinogen oxidase and applying to the crop and the weeds in the field a sufficient amount of glyphosate and an additional herbicide, such as, a hydroxyphenylpyruvatedioxygenase inhibitor, sulfonamide, imidazolinone, bialaphos, phosphinothricin, azafenidin, butafenacil, sulfosate, glufosinate, and a protox inhibitor to control the weeds without significantly affecting the crop. Various plants and seeds that can be used in this method are discussed in detail elsewhere herein.

Further provided is a method for producing a crop by growing a crop plant that is tolerant to glyphosate as a result of being transformed with a EPSPS polynucleotide or active variant or fragment thereof disclosed herein or as a result of the endogenous plant EPSPS gene being modified, under conditions such that the crop plant produces a crop, and harvesting the crop. Preferably, the glyphosate is applied to the plant, or in the vicinity of the plant, at a concentration effective to control weeds without preventing the transgenic crop plant from growing and producing the crop. The application of the glyphosate can be before planting, or at any time after planting up to and including the time of harvest. Glyphosate can be applied once or multiple times. The timing of glyphosate application, amount applied, mode of application, and other parameters will vary based upon the specific nature of the crop plant and the growing environment, and can be readily determined by one of skill in the art. A crop produced by this method is also provided.

Further provided are methods for the propagation of a plant containing an EPSPS polypeptide or active variant or fragment thereof. The plant can be, for example, a monocot or a dicot. In one aspect, propagation entails crossing a plant containing an EPSPS polynucleotide transgene with a second plant, such that at least some progeny of the cross display glyphosate tolerance.

The methods herein further allow for the development of herbicide applications to be used with the plants having the EPSPS sequence or active variants or fragments thereof. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, and seed of the crop or area of cultivation.

Any herbicide or combination of herbicides can be applied to the plant having the EPSPS sequence or active variant or fragment thereof disclosed herein or transgenic seed derived there from, crop part, or the area of cultivation containing the crop plant. By "treated with a combination of" or "applying a combination of" herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. The application of each herbicide and/or chemical may be simultaneous or the applications may be at different times (sequential), so long as the desired effect is achieved. Furthermore, the application can occur prior to the planting of the crop.

Classifications of herbicides (i.e., the grouping of herbicides into classes and subclasses) are well-known in the art and include classifications by HRAC (Herbicide Resistance Action Committee) and WSSA (the Weed Science Society of America) (see also, Retzinger and Mallory-Smith (1997) *Weed Technology* 11: 384-393).

Herbicides can be classified by their mode of action and/or site of action and can also be classified by the time at which they are applied (e.g., preemergent or postemergent), by the method of application (e.g., foliar application or soil application), or by how they are taken up by or affect the plant or by their structure. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action.

Often, an herbicide-tolerance gene that confers tolerance to a particular herbicide or other chemical on a plant expressing it will also confer tolerance to other herbicides or chemicals in the same class or subclass. Thus, in some embodiments, a transgenic plant is tolerant to more than one herbicide or chemical in the same class or subclass, such as, for example, an HPPD inhibitor, glyphosate, an ALS chemistry, an inhibitor of PPO, a sulfonylurea, and/or a synthetic auxin.

Typically, the plants of the present disclosure can tolerate treatment with different types of herbicides (i.e., herbicides having different modes of action and/or different sites of action) thereby permitting improved weed management strategies that are recommended in order to reduce the incidence and prevalence of herbicide-tolerant weeds.

In some embodiments, a plant of the disclosure is not significantly damaged by treatment with a glyphosate herbicide applied to that plant at a dose equivalent to a rate of at least 0.5, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 150, 170, 200, 300, 400, 500, 600, 700, 800, 800, 1000, 2000, 3000, 4000, 5000, 5400 or more grams or ounces (1 ounce=29.57 ml) of active ingredient or commercial product or herbicide formulation per acre or per hectare, whereas an appropriate control plant is significantly damaged by the same glyphosate treatment.

Additional ranges of the effective amounts of herbicides can be found, for example, in various publications from University Extension services. See, for example, Bernards, et al., (2006) *Guide for Weed Management in Nebraska* (www.ianrpubs.url.edu/sendlt/ec130); Regher, et al., (2005) Chemical Weed Control for Fields Crops, Pastures, Rangeland, and Noncropland, Kansas State University Agricultural Extension Station and Corporate Extension Service; Zollinger, et al., (2006) North Dakota Weed Control Guide, North Dakota Extension Service and the Iowa State University Extension at www.weeds.iastate.edu, each of which is herein incorporated by reference.

In some embodiments of the disclosure, glyphosate is applied to an area of cultivation and/or to at least one plant in an area of cultivation at rates between 8 and 32 ounces of acid equivalent per acre, or at rates between 10, 12, 14, 16, 18, 20, 22, 24, 26, 28 and 30 ounces of acid equivalent per acre at the lower end of the range of application and between 12, 14, 16, 18, 20, 22, 24, 26, 28, 30 and 32 ounces of acid equivalent per acre at the higher end of the range of application (1 ounce=29.57 ml). In other embodiments, glyphosate is applied at least at 1, 5, 10, 20, 30, 40, 50, 60, 70, 80, 90 or greater ounce of active ingredient per hectare (1 ounce=29.57 ml). In some embodiments of the disclosure, a sulfonylurea herbicide is applied to a field and/or to at least one plant in a field at rates between 0.04 and 1.0 ounces of active ingredient per acre, or at rates between 0.1, 0.2, 0.4, 0.6 and 0.8 ounces of active ingredient per acre at the lower end of the range of application and between 0.2, 0.4, 0.6, 0.8 and 1.0 ounces of active ingredient per acre at the higher end of the range of application. (1 ounce=29.57 ml). In some embodiments, as described herein, glyphosate treatment can be made at a stage starting from pre-emergence to early reproductive stages of the crop plant for weed control.

III. A Rapid Assay for Catalytic Efficiency of a Plurality of Enzyme Variants

One of the commercial applications of directed evolution is to desensitize an enzyme to inhibition by, for example, a herbicide. kcat, 1/KM, and KI are three dimensions that when multiplied are a measure of an enzyme's intrinsic capacity for catalysis in the presence of an inhibitor. The ideal values for the individual dimensions depend on substrate and inhibitor concentrations under the conditions of the application. When attempting to optimize those values by directed evolution, (kcat/KM)*KI can be an informative parameter for evaluating libraries of variants. However, evaluating (kcat/KM)*KI for hundreds of variants by substrate saturation analysis may not provide adequate throughput. A manipulation of the Michaelis-Menten equation that enables isolation of (kcat/KM)*KI on one side of the equation is presented herein. If substrate and enzyme concentrations are identical but velocity is measured at two different inhibitor concentrations (one of which can be 0), the data are sufficient to calculate (kcat/KM)*KI with just two rate measurements. The procedure has been validated by correlating values obtained with the rapid method with those obtained by substrate saturation kinetics.

The method includes (a) providing a plurality of enzyme variants; (b) providing the inhibitor; (c) providing the substrate; (d) performing a reaction involving the plurality of enzyme variants and the substrate, at no more than two different inhibitor concentrations; (e) measuring reaction rate at no more than two different inhibitor concentrations; and (f) calculating (kcat/KM)*KI of the plurality of enzyme variants. In some embodiments, one of the inhibitor concentrations is zero. In other embodiments, the substrate is at a concentration that is substantially similar to Michaelis-Menten constant (KM) of a parental enzyme for the enzyme variant. In still other embodiments, the enzyme is at a sufficient concentration to result in a substantially linear reaction rate at the two different inhibitor concentrations. In still other embodiments, one of the inhibitor concentrations is sufficient to result in at least about 50% inhibition. In still other embodiments, the assay is performed in a high-throughput system. In still other embodiments, the catalytic capacity in the presence of the inhibitor is estimated by obtaining a numerical value for (kcat/KM)*KI, wherein kcat is maximum enzyme turnover rate, KM is Michaelis-Menten constant and KI is inhibitor dissociation constant. In some embodiments, the substrate is PEP; the inhibitor is glyphosate; and the plurality of enzyme variants are EPSPS enzyme variants. In still other embodiments, the enzyme and the substrate concentrations are the same, at the two inhibitor concentrations.

EXAMPLES

In the following Examples, unless otherwise stated, in which parts and percentages are by weight and degrees are Celsius. It should be understood that these Examples, while indicating embodiments of the invention, are given by way of illustration only. From the above discussion and these Examples, one skilled in the art, can make various changes and modifications of the invention to adapt it to various usages and conditions. Such modifications are also intended to fall within the scope of the appended embodiments.

Example 1

Expression, Purification, and Assessment of Plant EPSP Synthases

The amino acid sequence of mature *Zea mays* EPSP synthase (EPSPS) was obtained from GenBank entry CAA44974.1 (NCBI GI No. 1524383; presented herein as SEQ ID NO:2). A nucleotide sequence was created to add an N-terminal methionine and to optimize codon usage for expression in *E. coli*. The synthetic gene was supplied by a commercial vendor. The gene was cloned into an expression vector that provides a T7 promoter driving expression of the protein. The vector was modified to change a 6× N-terminal histidine tag to a 10× tag. The resulting coding region of the vector yields an expressed protein with the amino acid sequence shown in Table 1 (represented by SEQ ID NO:1). The coding region is preceded by an N-terminal extension represented by SEQ ID NO:3.

TABLE 1

Amino acid sequence of the variant termed "native maize EPSPS". This sequence is the reference for all position numbers provided herein as it relates to maize EPSPS mutations disclosed herein.

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| M | A | G | A | E | E | I | V | L | Q  | P  | I  | K  | E  | I  |
| 16 | 17 | 18 | 19 | 20 | 21 | 22 | 23 | 24 | 25 | 26 | 27 | 28 | 29 | 30 |
| S | G | T | V | K | L | P | G | S | K | S | L | S | N | R |
| 31 | 32 | 33 | 34 | 35 | 36 | 37 | 38 | 39 | 40 | 41 | 42 | 43 | 44 | 45 |
| I | L | L | L | A | A | L | S | E | G | T | T | V | V | D |
| 46 | 47 | 48 | 49 | 50 | 51 | 52 | 53 | 54 | 55 | 56 | 57 | 58 | 59 | 60 |
| N | L | L | N | S | E | D | V | H | Y | M | L | G | A | L |
| 61 | 62 | 63 | 64 | 65 | 66 | 67 | 68 | 69 | 70 | 71 | 72 | 73 | 74 | 75 |
| R | T | L | G | L | S | V | E | A | D | K | A | A | K | R |
| 76 | 77 | 78 | 79 | 80 | 81 | 82 | 83 | 84 | 85 | 86 | 87 | 88 | 89 | 90 |
| A | V | V | V | G | C | G | G | K | F | P | V | E | D | A |
| 91 | 92 | 93 | 94 | 95 | 96 | 97 | 98 | 99 | 100 | 101 | 102 | 103 | 104 | 105 |
| K | E | E | V | Q | L | F | L | G | N | A | G | T | A | M |
| 106 | 107 | 108 | 109 | 110 | 111 | 112 | 113 | 114 | 115 | 116 | 117 | 118 | 119 | 120 |
| R | P | L | T | A | A | V | T | A | A | G | G | N | A | T |
| 121 | 122 | 123 | 124 | 125 | 126 | 127 | 128 | 129 | 130 | 131 | 132 | 133 | 134 | 135 |
| Y | V | L | D | G | V | P | R | M | R | E | R | P | I | G |
| 136 | 137 | 138 | 139 | 140 | 141 | 142 | 143 | 144 | 145 | 146 | 147 | 148 | 149 | 150 |
| D | L | V | V | G | L | K | Q | L | G | A | D | V | D | C |
| 151 | 152 | 153 | 154 | 155 | 156 | 157 | 158 | 159 | 160 | 161 | 162 | 163 | 164 | 165 |
| F | L | G | T | D | C | P | P | V | R | V | N | G | I | G |
| 166 | 167 | 168 | 169 | 170 | 171 | 172 | 173 | 174 | 175 | 176 | 177 | 178 | 179 | 180 |
| G | L | P | G | G | K | V | K | L | S | G | S | I | S | S |
| 181 | 182 | 183 | 184 | 185 | 186 | 187 | 188 | 189 | 190 | 191 | 192 | 193 | 194 | 195 |
| Q | Y | L | S | A | L | L | M | A | A | P | L | A | L | G |
| 196 | 197 | 198 | 199 | 200 | 201 | 202 | 203 | 204 | 205 | 206 | 207 | 208 | 209 | 210 |
| D | V | E | I | E | I | I | D | K | L | I | S | I | P | Y |
| 211 | 212 | 213 | 214 | 215 | 216 | 217 | 218 | 219 | 220 | 221 | 222 | 223 | 224 | 225 |
| V | E | M | T | L | R | L | M | E | R | F | G | V | K | A |
| 226 | 227 | 228 | 229 | 230 | 231 | 232 | 233 | 234 | 235 | 236 | 237 | 238 | 239 | 240 |
| E | H | S | D | S | W | D | R | F | Y | I | K | G | G | Q |
| 241 | 242 | 243 | 244 | 245 | 246 | 247 | 248 | 249 | 250 | 251 | 252 | 253 | 254 | 255 |
| K | Y | K | S | P | K | N | A | Y | V | E | G | D | A | S |
| 256 | 257 | 258 | 259 | 260 | 261 | 262 | 263 | 264 | 265 | 266 | 267 | 268 | 269 | 270 |
| S | A | S | Y | F | L | A | G | A | A | I | T | G | G | T |
| 271 | 272 | 273 | 274 | 275 | 276 | 277 | 278 | 279 | 280 | 281 | 282 | 283 | 284 | 285 |
| V | T | V | E | G | C | G | T | T | S | L | Q | G | D | V |
| 286 | 287 | 288 | 289 | 290 | 291 | 292 | 293 | 294 | 295 | 296 | 297 | 298 | 299 | 300 |
| K | F | A | E | V | L | E | M | M | G | A | K | V | T | W |

TABLE 1-continued

Amino acid sequence of the variant termed "native maize EPSPS". This sequence is the reference for all position numbers provided herein as it relates to maize EPSPS mutations disclosed herein.

| 301 | 302 | 303 | 304 | 305 | 306 | 307 | 308 | 309 | 310 | 311 | 312 | 313 | 314 | 315 |
|---|---|---|---|---|---|---|---|---|---|---|---|---|---|---|
| T | E | T | S | V | T | V | T | G | P | P | R | E | P | F |
| 316 | 317 | 318 | 319 | 320 | 321 | 322 | 323 | 324 | 325 | 326 | 327 | 328 | 329 | 330 |
| G | R | K | H | L | K | A | I | D | V | N | M | N | K | M |
| 331 | 332 | 333 | 334 | 335 | 336 | 337 | 338 | 339 | 340 | 341 | 342 | 343 | 344 | 345 |
| P | D | V | A | M | T | L | A | V | V | A | L | F | A | D |
| 346 | 347 | 348 | 349 | 350 | 351 | 352 | 353 | 354 | 355 | 356 | 357 | 358 | 359 | 360 |
| G | P | T | A | I | R | D | V | A | S | W | R | V | K | E |
| 361 | 362 | 363 | 364 | 365 | 366 | 367 | 368 | 369 | 370 | 371 | 372 | 373 | 374 | 375 |
| T | E | R | M | V | A | I | R | T | E | L | T | K | L | G |
| 376 | 377 | 378 | 379 | 380 | 381 | 382 | 383 | 384 | 385 | 386 | 387 | 388 | 389 | 390 |
| A | S | V | E | E | G | P | D | Y | C | I | I | T | P | P |
| 391 | 392 | 393 | 394 | 395 | 396 | 397 | 398 | 399 | 400 | 401 | 402 | 403 | 404 | 405 |
| E | K | L | N | V | T | A | I | D | T | Y | D | D | H | R |
| 406 | 407 | 408 | 409 | 410 | 411 | 412 | 413 | 414 | 415 | 416 | 417 | 418 | 419 | 420 |
| M | A | M | A | F | S | L | A | A | C | A | E | V | P | V |
| 421 | 422 | 423 | 424 | 425 | 426 | 427 | 428 | 429 | 430 | 431 | 432 | 433 | 434 | 435 |
| T | I | R | D | P | G | C | T | R | K | T | F | P | D | Y |
| 436 | 437 | 438 | 439 | 440 | 441 | 442 | 443 | 444 | 445 |     |     |     |     |     |
| F | D | V | L | S | T | F | V | K | N |     |     |     |     |     |

AroA Knock-Out Strain

The *E. coli* gene coding for EPSPS (AroA) was functionally deleted by P1 phage viral transduction. The donor strain was JW0891 (CGSC), in which the AroA gene is disrupted with a Kanamycin resistant gene. The recipient strain was BI21 DE3-Tuner (Novagen). Virus particles were propagated in untransformed Top10 cells. A stock of $10^9$ plaque forming units was diluted 1:10 and 1:100. From each dilution, 10 uL of phage was added to 0.3 ml of JW0891 donor cells at a density of 0.4 OD. After 30 min at 37° C., the mixture of phage and cells was plated on top agar (0.6%) and grown overnight at 37° C. Five ml of liquid LB medium containing 10 mM $CaCl_2$) was added to the top agar to harvest the plaques. The collected liquid was combined with 1 ml of chloroform and mixed thoroughly. The mixture was then spun and the supernatant was stored at 4° C. Transduction mixtures contained 0.3 ml of BL21(DE3) Tuner cells in LB at a density of 0.5 OD, 10 mM $CaCl_2$) and 10 ul of virus particles harvested from the donor cells, at 10-, 100- and 1000-fold dilution. Transduction was allowed to proceed at 37° C. for 1 hour. 120 ul of LB containing 100 mM sodium citrate was added to each cell and phage mixture and the mixtures were shaken for 1 hour at 37° C. Cells were plated on selective medium containing 40 mg/L Kanamycin and sodium citrate. Transduction of the disrupted AroA gene into Tuner was confirmed by sequencing the region of the AroA gene. The Tuner knockout strain was made electrocompetent by washing and resuspending in 10% glycerol.

EPSPS Production and Purification

Whether protein production was done in BL21(DE3) or with the Tuner AroA knockout, the vector was electroporated into cells and transformants were selected for growth on LB agar containing 100 ug carbennicillin/ml. Cells were grown in Magic Medium, in which induction occurs when the medium becomes depleted of glucose. After 4 hours of growth at 37° C., cells were transferred to 30° C. and grown another 16 hrs. Pelleted cells were lysed with BPER (Pierce) protein extraction reagent containing 0.2 mg/ml lysozyme, 1 mM dithiothreitol, protease inhibitor cocktail (Sigma, bacterial cocktail) and endonuclease. Insoluble cellular debris was removed by centrifugation. EPSPS protein was purified from the soluble protein solution by affinity chromatography on the nickel form of nitrilotriacetic acid (Ni-NTA) resin (Qiagen). Protein concentration was measured by absorbance at 280 nm using an extinction coefficient of 0.676 OD/mg/ml, provided by Vector NTI.

EPSPS Assay

Shikimate-3-phosphate (S3P) was prepared from cultures of *Klebsiella pneumonia* aroA- (ATCC 25597). Cells from a 500 ml culture grown in 2×YT were used to inoculate 6 L of minimal medium augmented with 55 uM tyrosine, 60 uM phenylalanine, 25 uM tryptophan, 0.1 uM 4-aminobenzoate and 0.1 uM 4-hydroxybenzoate (Weiss et al., 1953. *J Amer Chem Soc* 75:5572-5576). Accumulation of S3P was monitored by anion exchange HPLC. After about 4 days shaking at 37 C, the concentration reached ~1 mM. S3P was purified from the culture supernatant by anion exchange chromatography in ammonium bicarbonate at pH 7.3, with gradient elution up to 0.7 M. S3P was cleanly separated from phosphate, which eluted earlier.

EPSPS activity was determined by quantifying the phosphate generated from the EPSPS reaction. Release of inorganic phosphate was coupled to reaction with 2-amino-6-mercapto-7-methylpurine ribonucleoside, catalyzed by purine-nucleoside phosphorylase (M R Webb, Proc. Natl. Acad. Sci. 89:4884-4887, 1992). The absorbance change that occurs was monitored at 360 nm, where the extinction is 11,200 $M^{-1}$ $cm^{-1}$, with a Spectramax plate reader (Molecular Devices). To determine kinetic parameters, the varied substrate was present at seven concentrations (the eighth being the blank, containing no substrate) ranging from 4 to 400 uM and the unvaried substrate present at saturation. Six microliters of 50-fold concentrated stock solutions of the varied substrate were placed in the wells of the 96-well assay plate and reactions were started with the addition of a mixture containing 25 mM Hepes, pH 7, 100 mM KCl, 0.3 mM 2-amino-6-mercapto-7-methylpurine ribonucleosde, 1 uM (1 unit/ml) purine-nucleoside phosphorylase (Sigma N8264) and 200 uM of the non-varied substrate. Reactions were monitored with a Spectramax plate reader. The Michaelis-Menten kinetics protocol of the Spectramax software was customized for the substrate concentrations used. The software returns values of $K_M$ and $V_{max}$ using the Lineweaver-Burke transformation of the Michaelis-Menten equation. To determine $k_{cat}$, $V_{max}$ (uM/min) was divided by the enzyme concentration (uM). To determine $K_I$, substrate saturation was repeated at a higher range of PEP concentrations in the presence of a concentration of glyphosate that yielded approximately 2-fold elevation in apparent $K_M$ for PEP. $K_I$ was then calculated from the following form of the Michaelis-Menten equation for competitive inhibition:

$$K_I = K_M[I]/(K_{M\,app} - K_M)$$

$K_M$ approximates the dissociation constant of the enzyme-substrate complex while $k_{cat}$ is the rate of conversion of substrate to product when the substrate concentration is saturating. $k_{cat}/K_M$ is a widely accepted parameter for catalytic efficiency when substrate concentration is low ($\sim K_M$). $K_I$ is the dissociation constant of the enzyme-inhibitor complex, with a higher value indicating that the equilibrium lies more toward free enzyme and higher insensitivity. The parameter $k_{cat}/K_M \times K_I$ is used to quantify both catalytic efficiency and insensitivity and thus the overall fitness of the enzyme.

Example 2

Directed Evolution of Maize EPSPS

Saturation Mutagenesis

The mature form of native maize EPSPS was subjected to saturation mutagenesis to discover novel mutations that reduce sensitivity to glyphosate. Libraries of substitutions for each position in the EPSPS polypeptide chain were created using NNK (where N represents a 25% mix each of adenine, thymine, guanine, and cytosine nucleotides; and K represents a 50% mix each of thymine and guanine nucleotides) as the degenerate codon for the position to be mutagenized. PCR reaction mixtures contained a mutagenic forward primer (NNK codon flanked by 28 nucleotides matching with template at each side of the NNK) and a reverse primer that was the complement of the sequence preceding the forward primer, 28 nucleotides in length. To make circular double stranded DNA plasmids from the blunt ended PCR products, the products were digested with T4 polynucleotide kinase, T4 DNA ligase, and DpnI (to disrupt the parental DNA template). After desalting by ultrafiltration, the ligation products were ready for transformation and downstream applications.

Screen for Beneficial Mutations

The requirement for flux through the EPSPS reaction for growth on minimal medium is a powerful selection for a functional EPSPS expressed from a plasmid, provided that the native AroA gene is knocked out. Thus, the Tuner knock out strain was used in the early phase of optimization where insensitivity to glyphosate would be in a range similar to that of the endogenous EPSPS. Single mutations in native EPSPS were not expected to confer significant insensitivity to glyphosate, so the glyphosate concentration in the selection medium was a relatively low concentration of 10 mM. Colonies were isolated and heterologously expressed EPSPS was produced and purified as above. Purified variants were then assayed by measuring reaction rates in the presence of 50 uM phosphoenolpyruvate (PEP) and shikimate-3-phosphate (S3P), with or without 10 uM glyphosate. Mutations beneficial for activity or insensitivity to glyphosate are shown in Table 2.

TABLE 2

Activity of maize EPSPS variants in the presence of 50 uM PEP and shikimate-3-phosphate, with or without the addition of 10 uM glyphosate. Values represent the rate of phosphate formation (uM per min) per uM EPSPS. The rate in the second column is the rate in the presence of 10 μM glyphosate, expressed as a % of the rate with no glyphosate.

| | Reaction rate | |
|---|---|---|
| Variant | No glyph | 10 μM glyph, % no glyph |
| 224R 249V | 768 | 3.09 |
| 241A 278G | 730 | 3.75 |
| 311S | 701 | 4.37 |
| 4R | 662 | 7.38 |
| 278V | 622 | 3.25 |
| 208V 313G | 607 | 3.21 |
| 202R | 586 | 7.48 |
| 4N | 571 | 7.56 |
| 194M | 508 | 11.5 |
| 78L | 506 | 13.4 |
| 328C | 497 | 11.1 |
| 6S | 489 | 8.29 |
| 437R | 481 | 11.3 |
| 402G | 465 | 19.1 |
| 4L | 431 | 13.2 |
| Maize wild-type | 424 | 9.49 |
| 76T | 404 | 18.8 |
| 438R | 377 | 19.1 |
| 2P | 365 | 13.3 |
| 445G | 335 | 18.5 |
| 313G | 330 | 9.04 |
| 310V | 323 | 7.98 |
| 391G | 317 | 10.5 |
| 338S | 294 | 15.2 |
| 101S | 216 | 29.1 |
| 302S | 189 | 19.3 |
| 107S | 179 | 33.2 |
| 156Y | 170 | 28.8 |
| 107G | 161 | 45.4 |
| 156G | 148 | 30.0 |
| 246G | 130 | 23.7 |
| 107L | 120 | 51.7 |
| 107V | 51 | 71.7 |
| 107Q | 37 | 95.4 |

Saturation Mutagenesis at Positions 103 and 107

NNK-enabled saturation mutagenesis was performed at positions 103 and 107 in the maize EPSPS sequence, and transformed BL21 DE3 cells were screened as described above. Representative results are presented in Table 3.

TABLE 3

Kinetic parameters of variants selected after simultaneous saturation mutagenesis at positions 103 and 107

| 103-107 | $k_{cat}$ | $K_M$ | $k_{cat}/K_M$ | $K_I$ | $k_{cat}/K_M$ * $K_I$ |
|---|---|---|---|---|---|
| G-W | 379 | 82.2 | 4.62 | 403 | 1862 |
| L-T | 184 | 45.8 | 4.02 | 289 | 1163 |
| L-A | 125 | 50.6 | 2.47 | 463 | 1143 |
| S-N | 161 | 38.1 | 4.23 | 244 | 1033 |
| V-G | 324 | 133 | 2.44 | 480 | 1170 |
| Native | 1464 | 15.7 | 93.8 | 0.13 | 11.8 |

The EPSPS-TGPW protein version is about 3,000 fold less sensitive to glyphosate. However, its catalytic efficiency ($k_{cat}/K_M$) is only 5% of that of native maize EPSPS due to its 4-fold lower $k_{cat}$ and 5-fold higher $K_M$ for PEP.

Combinatorial Shuffling of Native Maize EPSPS

The preceding investigation revealed no novel single mutations that confer significant insensitivity to glyphosate, nor any novel combinations of amino acids at positions 103 and 107 that confer insensitivity while preserving catalytic efficiency. However, some combination of the substitutions identified may yield a variant with the desired properties. Therefore a combinatorial library was designed and synthesized. The complete list of variable amino acid positions that were randomly combined in the library is shown in Table 4.

TABLE 4

| Diversity used to construct combinatorial library WT-FS. Shown are the position numbers and the substitutions in the native maize EPSPS (SEQ ID NO: 1). |
|---|
| 2P |
| 4LNR |
| 6S |
| 76T |
| 78L |
| 101S |
| 102A |
| 103IALGV |
| 107GLQSWA |
| 156GY |
| 194M |
| 202R |
| 208V |
| 224R |
| 241A |
| 246G |
| 249V |
| 278VG |
| 302S |
| 310V |
| 311S |
| 313G |
| 328C |
| 338S |
| 391G |
| 402G |
| 437R |
| 438R |
| 445G |

The diversity used in combinatorial library WT-FS is the same diversity shown in Tables 2 and 3 with the addition of G102A, 103A and 103I. 102A was added because of its known effect in desensitizing EPSPS to glyphosate (Sost and Amrhein. 1990. *Arch Biochem Biophy* 282:433-436; Eschenburg et al. 2002. *Planta* 216:129-35). The library was synthesized by fully synthetic shuffling (Ness, J. E. et al. 2002. *Nature Biotechnology* 20:1251-1255). The theoretical number of unique members the library could comprise assuming 1 to 10 mutations per gene is $5.6\times10^8$.

The vector DNA of the library was transformed into the BL21(DE3) Tuner AroA knockout strain and the cells were plated onto M9 medium containing 50 mM glyphosate. A small aliquot of the transformed cells was plated on LB, by which it was determined that $1.1\times10^8$ colony forming units, or 20% of the theoretical library size, were plated and screened. 115 colonies were picked and subjected to a second tier of screening in which EPSPS proteins were purified as described in Example 1 and activity measured under three conditions: 0.2 mM PEP and S3P, 0.05 mM PEP and S3P, and 0.05 mM PEP and S3P plus 10 uM glyphosate. Hits were selected by considering the reaction rate at high substrate concentrations (reflecting $k_{cat}$), the ratio of activity at low to high substrate concentrations (reflecting $K_M$), and the ratio of activity with to without glyphosate (reflecting $K_I$). The selected variants were subjected to substrate saturation kinetic analysis as described in Example 1. Kinetic parameters for selected variants are shown in Table 5.

TABLE 5

Kinetic parameters for variants selected from the WT-FS combinatorial library (see text for description)

| Variant | Mutations on wild-type | $k_{cat}$ $min^{-1}$ | $K_M$ uM | $k_{cat}/K_M$ $min^{-1}uM^{-1}$ | $K_I$ uM | $K_{cat}/K_M*K_I$ |
|---|---|---|---|---|---|---|
| WT-FS-B | 103I 107S 278G 338S | 97.2 | 27.7 | 3.57 | 552 | 1971 |
| WT-FS-D | 101S 107L 302S 338S | 1853 | 20.5 | 92.3 | 3.81 | 346 |
| WT-FS-E | 102A 302S 391G 438R | 398 | 165 | 2.41 | 1146 | 2763 |
| WT-FS-E2 | 102A 302S 391G 438R I208L | 596 | 87.7 | 6.80 | 663 | 4512 |
| G102A | 102A | 695 | 310 | 2.2 | 2290 | 5137 |
| P107L | 107L | 1452 | 67.1 | 22.1 | 3.6 | 79 |
| Native | | 1464 | 15.7 | 93.8 | 0.13 | 11.8 |

Variant B contains the T103I and P107S mutations present in the GA21 maize transformation event (e.g. U.S. Pat. Nos. 6,566,587 and 6,040,497). Kinetic analysis indicates that the TIPS mutations confer a high level of insensitivity to glyphosate while retaining near native affinity for PEP but with only ~5% of the native $k_{cat}$ (Funke et al. 2009. *J Biological Chemistry* 284:9854-9860; Yu et al. 2015. *Plant Physiology*. February 2015 pp. 00146.2015). Step-wise acquisition of both T103I and P107S mutations was documented in a population of *Eleusine indica* (Yu et al. 2015 supra). However, out of a population of 193 individual plants, only 1.6% were homozygous for TIPS, indicating that the normal catalytic capacity contributed from the P107S allele was more important for fitness than having the second allele contribute a highly insensitive, but catalytically deficient enzyme.

Variant E has alanine substituted for glycine at position 102. Alanine is present at the homologous position in the Type II EPSPS from *Agrobacterium* sp. Strain CP4, an enzyme with a high degree of insensitivity to glyphosate combined with a low $K_M$ for PEP of 12 uM (U.S. Pat. No. 5,633,435). Because PEP is shorter than glyphosate, it is hypothesized that the alanine methyl group in CP4 EPSPS is suitably positioned to interfere with binding of glyphosate but not PEP. There is only 24-26% homology between the CP4 enzyme and *E. coli* or maize EPSPS (U.S. Pat. No. 5,633,435).

The three additional mutations in variant WT-FS-E compared to G102A alone (Table 5) already confer a 2-fold improvement in $K_M$ for PEP. From those observations, it was reasoned that further mutagenesis of variant FS-WT-E could result in a context for the A102 methyl group such that its position could provide favorable kinetic parameters.

Likewise, the additional mutations present in variant WT-FS-D versus P107L alone provided improved kinetic parameters (Table 5). Further optimization of variants WT-FS-B, -D and -E, representing each of the previously known mechanisms for rendering an EPSPS that is less sensitive to inhibition by glyphosate, was attempted. The objectives were to increase the $k_{cat}$ of B, increase the $K_I$ of D and improve $k_{cat}/K_M$ for PEP of E. Each was subjected to saturation mutagenesis as described in Example 1. The neutral or beneficial single substitutions identified for each is shown in Table 6. (The table includes the results from saturation mutagenesis of variant 868-H6, discussed below.)

TABLE 6

Amino acid sequence diversity resulting from saturation mutagenesis of native maize EPSPS and variants WT-FS-B, WT-FS-D, WT-FS-E and 868-H6. Only the positions that vary from native maize EPSPS are included. Bold indicates the amino acids that were present in the backbone sequence prior to saturation mutagenesis.

| AA in native | Position | Native | B | D | E | H6 |
|---|---|---|---|---|---|---|
| A | 2 | P | | | R | R |
| A | 4 | LNR | | | PVW | W |
| E | 6 | S | | | | |
| A | 36 | | | M | G | |
| E | 39 | | | | G | |
| N | 46 | | | E | | |
| H | 54 | | W | R | M | E |
| L | 65 | | | | | V |
| A | 69 | | | | | V |
| A | 72 | | R | VP | GQ | QE |
| K | 74 | | | | | V |
| A | 76 | T | | | | V |
| V | 78 | L | | | | |
| K | 84 | | | | R | R |
| V | 87 | | | | | T |
| D | 89 | | | | | F |
| K | 91 | | | | | G |
| E | 92 | | | | | G |
| L | 98 | | | | C | C |
| A | 101 | S | | S | | |
| G | 102 | AG | | | A | A |
| T | 103 | IALGV | I | | | |
| P | 107 | GLQSWA | S | L | | |
| A | 111 | | V | | | |
| N | 118 | | | | | C |
| D | 124 | | | | N | |
| V | 126 | | A | | | |
| P | 127 | | | R | | |
| E | 131 | | | L | | |
| L | 137 | | | | M | |
| Q | 143 | | | G | | |
| L | 152 | | | VY | G | |
| C | 156 | GY | | | | |
| I | 164 | | | | V | |
| K | 171 | | G | | | |
| K | 173 | | G | G | R | |
| S | 177 | | | | | M |
| M | 188 | | C | | | |
| A | 190 | | S | | S | |
| L | 194 | M | | | | |
| D | 196 | | | | | E |
| E | 202 | R | | | | |
| I | 208 | V | | | LASREG | L |
| R | 216 | | | A | | |
| K | 224 | R | DN | E | RQ | |
| R | 233 | | | | M | |
| G | 239 | | | E | M | |
| K | 241 | A | | | AV | |
| K | 243 | | | W | | |
| K | 246 | G | | | | G |
| N | 247 | | | | LQ | |
| Y | 249 | V | | | | |
| E | 274 | | | Q | | |
| T | 279 | | | | A | A |
| T | 278 | VG | GTV | | | |
| K | 297 | | | | | SR |
| E | 302 | S | | S | S | S |
| T | 308 | | | A | | |
| P | 310 | V | | | | |
| P | 311 | S | | | | |
| E | 313 | G | | | | |
| N | 328 | C | | R | | |
| A | 338 | S | | AS | S | |
| A | 349 | | | I | | |
| T | 361 | | | | S | S |
| P | 382 | | | E | | D |
| E | 391 | G | | | G | G |
| D | 402 | G | | | | G |
| A | 416 | | | | | G |
| Y | 435 | | | F | | |
| D | 437 | R | | | | |
| V | 438 | R | | | R | R |
| T | 441 | | | | | Q |
| N | 445 | G | | | | |

There are several positions (54, 72, 173, and 224) at which saturation mutagenesis yielded neutral or beneficial mutations in multiple backbones. However, in most cases, the particular amino acid substitution was specific for a particular backbone. At only six positions (173, 190, 224, 241, 246, and 278) was the identical substitution found in more than two of the five backbones, and in no case was one found in four backbones. The general case is that there is little overlap in the neutral or beneficial single mutations among the backbones in which the diversity is generated, indicating that the impact on the fitness of the enzyme that accrues from a mutation depends on the sequence context in which the mutation occurs. Given the sequence homology among various plant EPSP synthases, the corresponding sequence context of the specific mutations provided herein for the maize EPSPS sequence, are readily ascertainable in another species such as rice, sorghum, and sunflower, based on the guidance of this disclosure. It is significant to note that none of the changes shown in Table 6 confers more than 2-fold improvement in $k_{cat}/K_M \times K_I$, found with the I208L mutation in variant WT-FS-E (Table 5).

both enzymes were toggled with the native amino acid. This would allow all positions to acquire a substitution or revert to the native amino acid, thus creating all possible combinations of the mutation present in the two variants and eliminating non-essential or deleterious mutations. The design of the library is seen in Table 8. Semi-synthetic shuffling was used to toggle the diversity at each position shown among the amino acids present in native maize EPSPS, 771-C2 and 868-H6. The procedure did not result in significant improvement. However, variant 123-C1 (herein also referred to as "C1") has kinetic parameters that were modestly improved over 868-H6, while having only 9 mutations compared with 15 for 868-H6. The 123-C1 sequence is shown in Table 8 and its kinetic data in Table 7.

TABLE 8

Diversity associated with descendants of variant WT-FS-E

| Variant | 2 | 4 | 54 | 72 | 84 | 98 | 102 | 173 | 208 | 243 |
|---|---|---|---|---|---|---|---|---|---|---|
| native | A | A | H | A | K | L | G | K | I | K |
| 771-C2 | A | W | M | A | K | C | A | R | L | E |
| 868-H6 | R | W | H | Q | R | C | A | K | L | K |
| 123-C1 | R | W | H | A | R | C | A | K | L | E |

| Variant | 279 | 302 | 361 | 391 | 402 | 416 | 438 | 440 | 441 | 442 |
|---|---|---|---|---|---|---|---|---|---|---|
| native | T | E | T | E | D | A | V | S | T | F |
| 771-C2 | T | S | S | P | G | G | R | R | Q | V |
| 868-H6 | A | S | S | G | G | G | R | S | Q | F |
| 123-C1 | T | E | T | P | G | A | V | S | T | F |

No fill: native
Gray fill, unique to the variant
Dark fill with white font: shared by more than one variant From the functional diversity identified for each, combinatorial libraries were constructed and screened. In the case of WT-FS-E, the I208L mutation was fixed into the backbone of the combinatorial library. Kinetic parameters of selected hits from the three combinatorial libraries are shown in Table 7.

TABLE 7

Kinetic parameters of selected variants following saturation mutagenesis and combinatorial shuffling of EPSPS variants FS-WT-B, -D and -E.

|  | $k_{cat}$, min$^{-1}$ | $K_M$, uM | $k_{cat}/K_M$ | $K_I$, uM | $k_{cat}/K_M * K_I$ |
|---|---|---|---|---|---|
| Native | 1464 | 15.7 | 93.8 | 0.13 | 12 |
| WT-FS-E2 | 596 | 87.7 | 6.80 | 663 | 4512 |
| 771-C2 | 348 | 21.0 | 16.5 | 350 | 5800 |
| 868-H6 | 386 | 24.0 | 16.1 | 629 | 10070 |
| 123-C1 | 438 | 24.2 | 18.1 | 559 | 10100 |

The improvements intended for FS-WT-B and -D, namely, improved $k_{cat}$ and $K_I$, respectively, did not ensue from one round of diversity generation and combinatorial shuffling and no attempt was made to further improve them (data not shown). However, two variants, 771-C2 and 868-H6 (herein also referred to as "C2" and "H6", respectively), were significantly improved relative to FS-WT-E-I208L. To fully explore the diversity present in 771-C2 and 868-H6, a library was constructed in which the variable positions of Example 3

Mutations of 868-H6 and 123-C1 are Transferable to EPSPS from Other Plant Species An alignment of the amino acid sequences of EPSPS from various plant species shows a level of homology ranging from 80% to 99%, suggesting that the mutations defined in the maize background would have a similar effect in EPSPS from other species. The alignment in Table 9 was used to map the 868-H6 and 123-C1 mutations onto the sequences shown.

Native EPSPS amino acid sequences of rice (*Oryza sativa*) (SEQ ID NO:7), sorghum (*Sorghum halepense*) (SEQ ID NO:8), and sunflower (*Helianthus annus*) (SEQ ID NO:9) including the chloroplast transit peptide sequences were assembled and analyzed for mapping the corresponding amino acid mutations from the maize 868-H6. If complete EPSPS sequences were not available, appropriate adjustments were made based on sequence alignments and conserved residue mapping.

There is no complete sequence available for *Helianthus annuus*. The sequence shown below is a composite of a partial *H. annuus* sequence (GE499295) coding for amino acids 61-323 in Table 9 and cDNA data for *H. salicifolius* (AY545662.1), *H. ciliaris* (EL428089) and TC22032 (unidentified species).

TABLE 9 represents the mapping of maize 868-H6 EPSPS mutations onto EPSPS from other crop species.
The 15 mutations present in 868-H6 are shown in reverse highlight. Zm: *Zea mays*;
Hel an: *Helianthus annuus*; Ory sa: *Oryza sativa*; Sor ha: *Sorghum halepense*.

|        | 1 | 2 | 3 | 4 | 5 | 6 | 7 | 8 | 9 | 10 | 11 | 12 | 13 | 14 | 15 | 16 | 17 | 18 | 19 | 20 |
|--------|---|---|---|---|---|---|---|---|---|----|----|----|----|----|----|----|----|----|----|----|
| Zm     | — | A | G | A | E | E | I | V | L | Q  | P  | I  | K  | E  | I  | S  | G  | T  | V  | K  |
| Zm H6, C1 | M | R | G | W | E | E | I | V | L | Q | P | I | K | E | I | S | G | T | V | K |
| Hel an | S | T | A | P | E | E | I | V | L | K  | P  | I  | K  | E  | I  | S  | G  | T  | V  | N  |
| Ory sa | A | A | K | A | E | E | I | V | L | Q  | P  | I  | R  | E  | I  | S  | G  | A  | V  | Q  |
| Sor ha | — | A | G | A | E | E | I | V | L | Q  | P  | I  | K  | E  | I  | S  | G  | T  | V  | K  |

|        | 21 | 22 | 23 | 24 | 25 | 26 | 27 | 28 | 29 | 30 | 31 | 32 | 33 | 34 | 35 | 36 | 37 | 38 | 39 | 40 |
|--------|----|----|----|----|----|----|----|----|----|----|----|----|----|----|----|----|----|----|----|----|
| Zm     | L  | P  | G  | S  | K  | S  | L  | S  | N  | R  | I  | L  | L  | L  | A  | A  | L  | S  | E  | G  |
| Zm H6, C1 | L | P | G | S | K | S | L | S | N | R | I | L | L | L | A | A | L | S | E | G |
| Hel an | L  | P  | G  | S  | K  | S  | L  | S  | N  | R  | I  | L  | L  | L  | A  | A  | L  | A  | E  | G  |
| Ory sa | L  | P  | G  | S  | K  | S  | L  | S  | N  | R  | I  | L  | L  | L  | S  | A  | L  | S  | E  | G  |
| Sor ha | L  | P  | G  | S  | K  | S  | L  | S  | N  | R  | I  | L  | L  | L  | A  | A  | L  | S  | E  | G  |

|        | 41 | 42 | 43 | 44 | 45 | 46 | 47 | 48 | 49 | 50 | 51 | 52 | 53 | 54 | 55 | 56 | 57 | 58 | 59 | 60 |
|--------|----|----|----|----|----|----|----|----|----|----|----|----|----|----|----|----|----|----|----|----|
| Zm     | T  | T  | V  | V  | D  | N  | L  | L  | N  | S  | E  | D  | V  | H  | Y  | M  | L  | G  | A  | L  |
| Zm H6, C1 | T | T | V | V | D | N | L | L | N | S | E | D | V | H | Y | M | L | G | A | L |
| Hel an | T  | T  | V  | V  | D  | N  | L  | L  | N  | S  | D  | D  | V  | H  | Y  | M  | L  | G  | A  | L  |
| Ory sa | T  | T  | V  | V  | D  | N  | L  | L  | N  | S  | E  | D  | V  | H  | Y  | M  | L  | E  | A  | L  |
| Sor ha | T  | T  | V  | V  | D  | N  | L  | L  | N  | S  | E  | D  | V  | H  | Y  | M  | L  | G  | A  | L  |

|        | 61 | 62 | 63 | 64 | 65 | 66 | 67 | 68 | 69 | 70 | 71 | 72 | 73 | 74 | 75 | 76 | 77 | 78 | 79 | 80 |
|--------|----|----|----|----|----|----|----|----|----|----|----|----|----|----|----|----|----|----|----|----|
| Zm     | R  | T  | L  | G  | L  | S  | V  | E  | A  | D  | K  | A  | A  | K  | R  | A  | V  | V  | V  | G  |
| Zm H6, C1 | R | T | L | G | L | S | V | E | A | D | K | Q | A | K | R | A | V | V | V | G |
| Hel an | R  | A  | L  | G  | L  | N  | V  | E  | E  | N  | G  | E  | I  | K  | R  | A  | T  | V  | E  | G  |
| Ory sa | K  | A  | L  | G  | L  | S  | V  | E  | A  | D  | K  | V  | A  | K  | R  | A  | V  | V  | V  | G  |
| Sor ha | N  | T  | L  | G  | L  | S  | V  | E  | A  | D  | K  | V  | A  | K  | R  | A  | V  | V  | V  | G  |

|        | 81 | 82 | 83 | 84 | 85 | 86 | 87 | 88 |    | 89 | 90 | 91 | 92 | 93 | 94 | 95 | 96 | 97 | 98 | 99 |
|--------|----|----|----|----|----|----|----|----|----|----|----|----|----|----|----|----|----|----|----|----|
| Zm     | C  | G  | G  | K  | F  | P  | V  | E  |    | —  | D  | A  | K  | E  | E  | V  | Q  | L  | F  | L  | G  |
| Zm H6, C1 | C | G | G | R | F | P | V | E |    | — | D | A | K | E | E | V | Q | L | F | C | G |
| Hel an | C  | G  | G  | V  | F  | P  | V  | G  |    | K  | E  | A  | K  | D  | E  | I  | Q  | L  | F  | L  | G  |
| Ory sa | C  | G  | G  | K  | F  | P  | V  | E  |    | K  | D  | A  | K  | E  | E  | V  | Q  | L  | F  | L  | G  |
| Sor ha | C  | G  | G  | K  | F  | P  | V  | E  |    | —  | D  | A  | K  | E  | E  | V  | Q  | L  | F  | L  | G  |

|        | 100 | 101 | 102 | 103 | 104 | 105 | 106 | 107 | 108 | 109 | 110 | 111 | 112 | 113 | 114 | 115 | 116 | 117 | 118 | 119 |
|--------|-----|-----|-----|-----|-----|-----|-----|-----|-----|-----|-----|-----|-----|-----|-----|-----|-----|-----|-----|-----|
| Zm     | N   | A   | G   | T   | A   | M   | R   | P   | L   | T   | A   | A   | V   | T   | A   | A   | G   | G   | N   | A   |
| Zm H6, C1 | N | A | R | T | A | M | R | P | L | T | A | A | V | T | A | A | G | G | N | A |
| Hel an | N   | A   | G   | T   | A   | M   | R   | P   | L   | T   | A   | A   | V   | T   | A   | A   | G   | G   | N   | S   |
| Ory sa | N   | A   | G   | T   | A   | M   | R   | P   | L   | T   | A   | A   | V   | T   | A   | A   | G   | G   | N   | A   |
| Sor ha | N   | A   | G   | T   | A   | M   | R   | P   | L   | T   | A   | A   | V   | T   | A   | A   | G   | G   | N   | A   |

|        | 120 | 121 | 122 | 123 | 124 | 125 | 126 | 127 | 128 | 129 | 130 | 131 | 132 | 133 | 134 | 135 | 136 | 137 | 138 | 139 |
|--------|-----|-----|-----|-----|-----|-----|-----|-----|-----|-----|-----|-----|-----|-----|-----|-----|-----|-----|-----|-----|
| Zm     | T   | Y   | V   | L   | D   | G   | V   | P   | R   | M   | R   | E   | R   | P   | I   | G   | D   | L   | V   | V   |
| Zm H6, C1 | T | Y | V | L | D | G | V | P | R | M | R | E | R | P | I | G | D | L | V | V |
| Hel an | S   | Y   | I   | L   | D   | G   | V   | P   | R   | M   | R   | E   | R   | P   | I   | G   | D   | L   | V   | T   |
| Ory sa | T   | Y   | V   | L   | D   | G   | V   | P   | R   | M   | R   | E   | R   | P   | I   | G   | D   | L   | V   | V   |
| Sorha  | T   | Y   | V   | L   | D   | G   | V   | P   | R   | M   | R   | E   | R   | P   | I   | G   | D   | L   | V   | V   |

|        | 140 | 141 | 142 | 143 | 144 | 145 | 146 | 147 | 148 | 149 | 150 | 151 | 152 | 153 | 154 | 155 | 156 | 157 | 158 | 159 |
|--------|-----|-----|-----|-----|-----|-----|-----|-----|-----|-----|-----|-----|-----|-----|-----|-----|-----|-----|-----|-----|
| Zm     | G   | L   | K   | Q   | L   | G   | A   | D   | V   | D   | C   | F   | L   | G   | T   | D   | C   | P   | P   | V   |
| Zm H6, C1 | G | L | K | Q | L | G | A | D | V | D | C | F | L | G | T | D | C | P | P | V |
| Hel an | G   | L   | K   | Q   | L   | G   | A   | D   | V   | D   | C   | F   | L   | G   | T   | N   | C   | P   | P   | V   |
| Ory sa | G   | L   | K   | Q   | L   | G   | A   | D   | V   | D   | C   | F   | L   | G   | T   | E   | C   | P   | P   | V   |
| Sor ha | G   | L   | K   | Q   | L   | G   | A   | D   | V   | D   | C   | F   | L   | G   | T   | D   | C   | P   | P   | V   |

|        | 160 | 161 | 162 | 163 | 164 | 165 | 166 | 167 | 168 | 169 | 170 | 171 | 172 | 173 | 174 | 175 | 176 | 177 | 178 | 179 |
|--------|-----|-----|-----|-----|-----|-----|-----|-----|-----|-----|-----|-----|-----|-----|-----|-----|-----|-----|-----|-----|
| Zm     | R   | V   | N   | G   | I   | G   | G   | L   | P   | G   | G   | K   | V   | K   | L   | S   | G   | S   | I   | S   |
| Zm H6  | R   | V   | N   | G   | I   | G   | G   | L   | P   | G   | G   | K   | V   | K   | L   | S   | G   | S   | I   | S   |
| Hel an | R   | V   | A   | N   | G   | G   | G   | L   | P   | G   | G   | K   | V   | K   | L   | S   | G   | S   | I   | S   |
| Ory sa | R   | V   | K   | G   | I   | G   | G   | L   | P   | G   | G   | K   | V   | K   | L   | S   | G   | S   | I   | S   |
| Sor ha | R   | I   | N   | G   | I   | G   | G   | L   | P   | G   | G   | K   | V   | K   | L   | S   | G   | S   | I   | S   |

|        | 180 | 181 | 182 | 183 | 184 | 185 | 186 | 187 | 188 | 189 | 190 | 191 | 192 | 193 | 194 | 195 | 196 | 197 | 198 | 199 |
|--------|-----|-----|-----|-----|-----|-----|-----|-----|-----|-----|-----|-----|-----|-----|-----|-----|-----|-----|-----|-----|
| Zm     | S   | Q   | Y   | L   | S   | A   | L   | L   | M   | A   | A   | P   | L   | A   | L   | G   | D   | V   | E   | I   |
| Zm H6, C1 | S | Q | Y | L | S | A | L | L | M | A | A | P | L | A | L | G | D | V | E | I |

TABLE 9-continued represents the mapping of maize 868-H6 EPSPS mutations onto EPSPS from other crop species. The 15 mutations present in 868-H6 are shown in reverse highlight. Zm: *Zea mays*; Hel an: *Helianthus annuus*; Ory sa: *Oryza sativa*; Sor ha: *Sorghum halepense*.

| | | | | | | | | | | | | | | | | | | | |
|---|---|---|---|---|---|---|---|---|---|---|---|---|---|---|---|---|---|---|---|
| Hel an | S | Q | Y | L | T | A | L | L | M | A | A | P | L | A | L | G | D | V | E | I |
| Ory sa | S | Q | Y | L | S | A | L | L | M | A | A | P | L | A | L | G | D | V | E | I |
| Sorha | S | Q | Y | L | S | A | L | L | M | A | A | P | L | A | L | G | D | V | E | I |

| | 200 | 201 | 202 | 203 | 204 | 205 | 206 | 207 | 208 | 209 | 210 | 211 | 212 | 213 | 214 | 215 | 216 | 217 | 218 | 219 |
|---|---|---|---|---|---|---|---|---|---|---|---|---|---|---|---|---|---|---|---|---|
| Zm | E | I | I | D | K | L | I | S | I | P | Y | V | E | M | T | L | R | L | M | E |
| Zm H6, C1 | E | I | I | D | K | L | I | S | L | P | Y | V | E | M | T | L | R | L | M | E |
| Hel an | E | I | I | D | K | L | I | S | V | P | Y | Y | V | E | M | T | L | R | L | M | E |
| Ory sa | E | I | I | D | K | L | I | S | I | P | Y | V | E | M | T | L | R | L | M | E |
| Sor ha | E | I | I | D | K | L | I | S | I | P | Y | V | E | M | T | L | R | L | M | E |

| | 220 | 221 | 222 | 223 | 224 | 225 | 226 | 227 | 228 | 229 | 230 | 231 | 232 | 233 | 234 | 235 | 236 | 237 | 238 | 239 |
|---|---|---|---|---|---|---|---|---|---|---|---|---|---|---|---|---|---|---|---|---|
| Zm | R | F | G | V | K | A | E | H | S | D | S | W | D | R | F | Y | I | K | G | G |
| Zm H6, C1 | R | F | G | V | K | A | E | H | S | D | S | W | D | R | F | Y | I | K | G | G |
| Hel an | R | F | G | V | S | V | E | H | S | D | S | W | D | K | F | Y | V | R | G | G |
| Ory sa | R | F | G | V | K | A | E | H | S | D | S | W | D | R | F | Y | I | K | G | G |
| Sor ha | R | F | G | V | K | A | E | H | S | D | S | W | D | R | F | Y | I | K | G | G |

| | 240 | 241 | 242 | 243 | 244 | 245 | 246 | 247 | 248 | 249 | 250 | 251 | 252 | 253 | 254 | 255 | 256 | 257 | 258 | 259 |
|---|---|---|---|---|---|---|---|---|---|---|---|---|---|---|---|---|---|---|---|---|
| Zm | Q | K | Y | K | S | P | K | N | A | Y | V | E | G | D | A | S | S | A | S | Y |
| Zm H6, C1 | Q | K | Y | E | S | P | K | N | A | Y | V | E | G | D | A | S | S | A | S | Y |
| Hel an | Q | K | Y | K | S | P | G | N | A | Y | V | E | G | D | A | S | S | A | S | Y |
| Ory sa | Q | K | Y | K | S | P | G | N | A | Y | V | E | G | D | A | S | S | A | S | Y |
| Sor ha | Q | K | Y | K | S | P | K | N | A | Y | V | E | G | D | A | S | S | A | S | Y |

| | 260 | 261 | 262 | 263 | 264 | 265 | 266 | 267 | 268 | 269 | 270 | 271 | 272 | 273 | 274 | 275 | 276 | 277 | 278 | 279 |
|---|---|---|---|---|---|---|---|---|---|---|---|---|---|---|---|---|---|---|---|---|
| Zm | F | L | A | G | A | A | I | T | G | G | T | V | T | V | E | G | C | G | T | T |
| Zm H6, C1 | F | L | A | G | A | A | I | T | G | G | T | V | T | V | E | G | C | G | T | A |
| Hel an | F | L | A | G | A | A | I | T | G | G | T | V | T | V | E | G | C | G | T | S |
| Ory sa | F | L | A | G | A | A | I | T | G | G | T | V | T | V | Q | G | C | G | T | T |
| Sor ha | F | L | A | G | A | A | I | T | G | G | T | V | T | V | E | G | C | G | T | T |

| | 280 | 281 | 282 | 283 | 284 | 285 | 286 | 287 | 288 | 289 | 290 | 291 | 292 | 293 | 294 | 295 | 296 | 297 | 298 | 299 |
|---|---|---|---|---|---|---|---|---|---|---|---|---|---|---|---|---|---|---|---|---|
| Zm | S | L | Q | G | D | V | K | F | A | E | V | L | E | M | M | G | A | K | V | T |
| Zm H6, C1 | S | L | Q | G | D | V | K | F | A | E | V | L | E | M | M | G | A | K | V | T |
| Hel an | S | L | Q | G | D | V | K | F | A | E | V | L | G | Q | M | G | A | E | V | T |
| Ory sa | S | L | Q | G | D | V | K | F | A | E | V | L | E | M | M | G | A | K | V | T |
| Sor ha | S | L | Q | G | D | V | K | F | A | E | V | L | E | M | M | G | A | K | V | T |

| | 300 | 301 | 302 | 303 | 304 | 305 | 306 | 307 | 308 | 309 | 310 | 311 | 312 | 313 | 314 | 315 | 316 | 317 | 318 | 319 |
|---|---|---|---|---|---|---|---|---|---|---|---|---|---|---|---|---|---|---|---|---|
| Zm | W | T | E | T | S | V | T | V | T | G | P | P | R | E | P | F | G | R | K | H |
| Zm H6, C1 | W | T | S | T | S | V | T | V | T | G | P | P | R | E | P | F | G | R | K | H |
| Hel an | W | T | E | N | S | V | T | V | R | G | P | P | R | N | A | S | G | R | G | H |
| Ory sa | W | T | D | T | S | V | T | V | T | G | P | P | R | E | P | Y | G | K | K | H |
| Sor ha | W | T | E | T | S | V | T | V | T | G | P | P | R | Q | P | F | G | R | K | H |

| | 320 | 321 | 322 | 323 | 324 | 325 | 326 | 327 | 328 | 329 | 330 | 331 | 332 | 333 | 334 | 335 | 336 | 337 | 338 | 339 |
|---|---|---|---|---|---|---|---|---|---|---|---|---|---|---|---|---|---|---|---|---|
| Zm | L | K | A | I | D | V | N | M | N | K | M | P | D | V | A | M | T | L | A | V |
| Zm H6, C1 | L | K | A | I | D | V | N | M | N | K | M | P | D | V | A | M | T | L | A | V |
| Hel an | L | R | P | V | D | V | N | M | N | K | M | P | D | V | A | M | T | L | A | V |
| Ory sa | L | K | A | V | D | V | N | M | N | K | M | P | D | V | A | M | T | L | A | V |
| Sor ha | L | K | A | I | D | V | N | M | N | K | M | P | D | V | A | M | T | L | A | V |

| | 340 | 341 | 342 | 343 | 344 | 345 | 346 | 347 | 348 | 349 | 350 | 351 | 352 | 353 | 354 | 355 | 356 | 357 | 358 | 359 |
|---|---|---|---|---|---|---|---|---|---|---|---|---|---|---|---|---|---|---|---|---|
| Zm | V | A | L | F | A | D | G | P | T | A | I | R | D | V | A | S | W | R | V | K |
| Zm H6, C1 | V | A | L | F | A | D | G | P | T | A | I | R | D | V | A | S | W | R | V | K |
| Hel an | V | A | L | Y | A | D | G | P | T | A | I | R | D | V | A | S | W | R | V | K |
| Ory sa | V | A | L | F | A | D | G | P | T | A | I | R | D | V | A | S | W | R | V | K |
| Sor ha | V | A | L | F | A | D | G | P | T | A | I | R | D | V | A | S | W | R | V | K |

| | 360 | 361 | 362 | 363 | 364 | 365 | 366 | 367 | 368 | 369 | 370 | 371 | 372 | 373 | 374 | 375 | 376 | 377 | 378 | 379 |
|---|---|---|---|---|---|---|---|---|---|---|---|---|---|---|---|---|---|---|---|---|
| Zm | E | T | E | R | M | V | A | I | R | T | E | L | T | K | L | G | A | S | V | E |
| Zm H6, C1 | E | S | E | R | M | V | A | I | R | T | E | L | T | K | L | G | A | S | V | E |
| Hel an | E | T | E | R | M | I | A | I | C | T | E | L | R | K | L | G | A | T | V | E |
| Ory sa | E | T | E | R | M | V | A | I | R | T | E | L | T | K | L | G | A | S | V | E |
| Sor ha | E | T | E | R | M | V | A | I | R | T | E | L | T | K | L | G | A | S | V | E |

TABLE 9-continued represents the mapping of maize 868-H6 EPSPS mutations onto EPSPS from other crop species.
The 15 mutations present in 868-H6 are shown in reverse highlight. Zm: *Zea mays*;
Hel an: *Helianthus annuus*; Ory sa: *Oryza sativa*; Sor ha: *Sorghum halepense*.

|        | 380 | 381 | 382 | 383 | 384 | 385 | 386 | 387 | 388 | 389 | 390 | 391 | 392 | 393 | 394 | 395 | 396 | 397 | 398 | 399 |
|--------|-----|-----|-----|-----|-----|-----|-----|-----|-----|-----|-----|-----|-----|-----|-----|-----|-----|-----|-----|-----|
| Zm     | E   | G   | P   | D   | Y   | C   | I   | I   | T   | P   | P   | E   | K   | L   | N   | V   | T   | A   | I   | D   |
| Zm H6, C1 | E | G | P | D | Y | C | I | I | T | P | P | G/P | K | L | N | V | T | A | I | D |
| Hel an | E   | G   | P   | D   | Y   | C   | V   | I   | T   | P   | P   | E   | K   | L   | N   | V   | T   | A   | I   | D   |
| Ory sa | E   | G   | P   | D   | Y   | C   | I   | I   | T   | P   | P   | E   | K   | L   | N   | I   | T   | A   | I   | D   |
| Sor ha | E   | G   | P   | D   | Y   | C   | I   | I   | T   | P   | P   | E   | K   | L   | N   | V   | T   | A   | I   | D   |

|        | 400 | 401 | 402 | 403 | 404 | 405 | 406 | 407 | 408 | 409 | 410 | 411 | 412 | 413 | 414 | 415 | 416 | 417 | 418 | 419 |
|--------|-----|-----|-----|-----|-----|-----|-----|-----|-----|-----|-----|-----|-----|-----|-----|-----|-----|-----|-----|-----|
| Zm     | T   | Y   | D   | D   | H   | R   | M   | A   | M   | A   | F   | S   | L   | A   | A   | C   | A   | E   | V   | P   |
| Zm H6, C1 | T | Y | G | D | H | R | M | A | M | A | F | S | L | A | A | C | G | E | V | P |
| Hel an | T   | Y   | D   | D   | H   | R   | M   | A   | M   | A   | F   | S   | L   | A   | A   | C   | A   | D   | V   | P   |
| Ory sa | T   | Y   | D   | D   | H   | R   | M   | A   | M   | A   | F   | S   | L   | A   | A   | C   | A   | D   | V   | P   |
| Sor ha | T   | Y   | D   | D   | H   | R   | M   | A   | M   | A   | F   | S   | L   | A   | A   | C   | A   | E   | V   | P   |

|        | 420 | 421 | 422 | 423 | 424 | 425 | 426 | 427 | 428 | 429 | 430 | 431 | 432 | 433 | 434 | 435 | 436 | 437 | 438 | 439 |
|--------|-----|-----|-----|-----|-----|-----|-----|-----|-----|-----|-----|-----|-----|-----|-----|-----|-----|-----|-----|-----|
| Zea ma | V   | T   | I   | R   | D   | P   | G   | C   | T   | R   | K   | T   | F   | P   | D   | Y   | F   | D   | V   | L   |
| Zm H6, C1 | V | T | I | R | D | P | G | C | T | R | K | T | F | P | D | Y | F | D | R | L |
| Hel an | V   | T   | I   | K   | D   | P   | G   | C   | T   | R   | K   | T   | F   | P   | D   | Y   | F   | E   | V   | L   |
| Ory sa | V   | T   | I   | R   | D   | P   | G   | C   | T   | R   | K   | T   | F   | P   | N   | Y   | F   | D   | V   | L   |
| Sor ha | V   | T   | I   | R   | D   | P   | G   | C   | T   | R   | K   | T   | F   | P   | D   | Y   | F   | D   | V   | L   |

|        | 440 | 441 | 442 | 443 | 444 | 445 | Species | Genbank # |
|--------|-----|-----|-----|-----|-----|-----|---------|-----------|
| Zea ma | S   | T   | F   | V   | K   | N   | *Zea mays* | CAA44974 |
| Zm H6, C1 | S | Q | F | V | K | N | 868-H6, 123-C1 | |
| Hel an | E   | R   | F   | T   | K   | H   | *Helianthus anuus* | |
| Ory sa | S   | T   | F   | V   | R   | N   | *Oryza sativa* | AF413082 |
| Sor ha | S   | T   | F   | V   | K   | N   | *Sorghum halepense* | H6T5X2 |

Reverse highlight: H6 and C1
Bold: unique to H6
Bold, Shaded: unique to C1

For 10 of the 15 mutations in maize clone 868-H6 (98, 102, 208, 279, 302, 361, 391, 402, 416 and 438), the context of the amino acid positions as well as the chemical character of the native amino acid were highly homologous. For the remaining amino acid positions (2, 4, 72, 84 and 441), the native amino acids in the sunflower sequence differed significantly from the monocot maize sequence. However, the H6 changes were incorporated into the mutated sunflower sequence (SEQ ID NO:10) as indicated in Table 9 regardless of those considerations.

ChloroP Prediction Server (Emanuelsson, O. et al. 1999. *Protein Sci.* 8(5):978-84) was used to approximate the amino terminus of the mature EPSPS proteins. Nucleotide sequences of both native and mutagenized genes were optimized for expression in *E. coli* and synthesized. The synthetic genes were cloned into a plasmid vector and expressed, purified and analyzed as described in Example 1. The kinetic parameters of the purified EPSPS proteins are shown in Table 10.

TABLE 10

Kinetic parameters of native EPSPS from various species and the same enzymes carrying the 868-H6 mutations. $K_M$ values are for PEP.

|  | $k_{cat}$, min$^{-1}$ | $K_M$, uM | $k_{cat}/K_M$ | $K_I$, uM | kcat/$K_M$ * $K_I$ |
|---|---|---|---|---|---|
| Zea ma, native (SEQ ID NO: 2) | 1464 | 15.7 | 93.8 | 0.13 | 12 |
| Zea ma, H6 (SEQ ID NO: 5) | 386 | 24.0 | 16.1 | 629 | 10070 |
| Sor ha, native (SEQ ID NO: 8) | 3056 | 17.4 | 176 | 0.2 | 33 |
| Sor haH6 (SEQ ID NO: 12) | 317 | 30.6 | 10.0 | 783 | 8080 |
| Ory sa, native (SEQ ID NO: 7) | 1858 | 12.6 | 148.0 | 0.10 | 18 |
| Ory sa, H6 (SEQ ID NO: 11) | 293 | 28.9 | 10.0 | 907 | 9200 |
| *Helianthus annuus*, native (SEQ ID NO: 9) | 1771 | 18.8 | 94 | 0.15 | 14 |
| Hel an, H6 (SEQ ID NO: 10) | 211 | 37.2 | 6.0 | 1583 | 8960 |

The combination of mutations discovered in 868-H6 maize EPSPS clearly had a very similar effect on fitness ($k_{cat}/K_M*K_I$) when mapped onto EPSPS from other species. Not surprisingly, the greatest deviation in individual parameters was with sunflower in comparison with the monocot species. Sunflower had higher $K_M$ for PEP and a lower $k_{cat}$, resulting in a $k_{cat}/K_M$ that was 38% that of maize H6. However, the mutant sunflower enzyme had a 74% to 150% higher $K_I$ for glyphosate than the mutant monocot EPSPS enzymes.

Likewise, the mutations present in maize EPSPS 123-C1 (See Table 8) were mapped onto the amino acid sequences of sorghum (SEQ ID NO:23) and the proteins were produced and purified as above. The enzyme activity was analyzed by measuring reaction rates when PEP and S3P were both present at 200 uM, and when substrates were present at 30 uM and glyphosate at 1 mM (Table 11).

TABLE 11

Reaction rates of EPSPS enzymes with mutations at G102A alone or the mutations defined for maize variant 123-C1.

| | Native | | G102A | | C1 mutations | |
|---|---|---|---|---|---|---|
| Species | 200 uM, no glyph | 30 uM, 1 mM glyph | 200 uM, no glyph | 30 uM, 1 mM glyph | 200 uM, no glyph | 30 uM, 1 mM glyph |
| Sor ha | 1376 | −2.2 | 239 | 24.4 | 356 | 60.0 |
| Zea ma | 1464 | 0.0 | 270 | 41.0 | 516 | 94.5 |

For sorghum and maize EPSPS, the benefit of the C1 mutations compared to G102A alone is seen both in the presence and absense of glyphosate, due to the much lower $K_M$ for PEP conferred by the 8 other mutations.

The mutations can also be mapped to other known EPSPS sequences from various crops (see, for example, SEQ ID NOs: 13-17 that correspond to mutated versions (see, for example, SEQ ID NOs: 18-22) containing the H6 mutations). The alignments of the native EPSPS sequences with their corresponding mutated versions are shown in FIGS. 1-8.

Example 4

Production of Glyphosate-Resistant Maize Expressing Glyphosate Tolerant Plant EPSPS Maize plants expressing EPSPS variant genes are produced using at least two approches—(i) recombinant DNA-based transformation or site-directed changes at the endogenous EPSPS genomic locus. Recombinant DNA based transformation methods are well known in the art, e.g. *Agrobacterium tumefaciens*-mediated and particle bombardment based transformations.

(i) Recombinant Maize EPSPS-Variant Transformation

*Agrobacterium tumefaciens* based plant transformation vectors are constructed according to methods known in the art. EPSPS vectors contain a T-DNA insert having a constitutive plant promoter, such as an ubiquitin promoter, an intron, an optional enhancer such as a 35S enhancer element, an EPSPS variant DNA encoding a glyphosate tolerant EPSPS (e.g., 868-H6), and a plant terminator such as, for example, a PinII terminator. Maize immature embryos are excised and infected with an *Agrobacterium tumefaciens* vector containing the EPSPS variant of interest. After infection, embryos are transferred and cultured in co-cultivation medium. After co-cultivation, the infected immature embryos are transferred onto media containing 1.0 mM glyphosate. This selection generally lasts until actively growing putative transgenic calli are identified. The putative transgenic callus tissues are sampled using PCR and optionally a Western assay to confirm the presence of the EPSPS variant gene. The putative transgenic callus tissues are maintained on 1.0 mM glyphosate selection media for further growth and selection before plant regeneration. At regeneration, callus tissue confirmed to be transgenic are transferred onto maturation medium containing 0.1 mM glyphosate and cultured for somatic embryo maturation. Mature embryos are then transferred onto regeneration medium containing 0.1 mM glyphosate for shoot and root formation. After shoots and roots emerge, individual plantlets are transferred into tubes with rooting medium containing 0.1 mM glyphosate. Plantlets with established shoots and roots are transplanted into pots in the greenhouse for further growth, to obtain T0 spray data, and to produce T1 seed.

In order to evaluate the level of glyphosate resistance of the transgenic maize plants expressing the EPSPS variant transgenes, T0 plants are sprayed with glyphosate in the greenhouse. Glyphosate concentrations include dosage of e.g., 1× rate of a commercially available glyphosate formulation. Plant resistance levels are evaluated by plant discoloration scores and plant height measurements. Plant discoloration is evaluated according to the following scale:
Discoloration Score at 1, 2, 3 and 4 Weeks After Spray with Glyphosate
9=no leaf/stem discoloration
7=minor leaf/stem discoloration
5=worse leaf/stem discoloration
3=severely discolored plant or dying plant
1=dead plant Plant Height Measurements are recorded before spraying with glyphosate and after spraying with glyphosate at 1, 2, 3 and 4 weeks post-application. Two plants are sent to the greenhouse from each event (independent transgenic callus). Plant 1 is kept for seed production and is not sprayed with glyphosate. Plant 2 is sprayed at 2×-4× glyphosate (1× glyphosate=26 ounces/acre) at 14 days after transplanting. The T0 plant discoloration scores at 7 and 14 days after the spray are also observed. Height data at tasseling is also measured.

(ii) Guided Cas9-Based EPSPS Modifications

Expression cassettes for guide RNA/Cas endonuclease based genome modification in maize plants are disclosed at least in Examples 1-15 of International Application No. PCT/US2015/38767, filed Jul. 1, 2015 and herein incorporated by reference.

Described herein is a guide RNA/Cas endonuclease system that is based on the type II CRISPR/Cas system and includes a Cas endonuclease and a guide RNA (or duplexed crRNA and tracrRNA) that together can form a complex that recognizes a genomic target site in a plant and introduces a double-strand-break into said target site (U.S. patent application 61/868,706, filed Aug. 22, 2013), incorporated herein by reference. In this Example, the desired target site is the maize endogenous native EPSPS genomic sequence.

The maize optimized Cas9 endonuclease and single guide RNA expression cassettes containing the specific maize variable targeting domains are co-delivered to e.g., 60-90 Hi-II immature maize embryos by particle-mediated delivery using techniques well known in the art and optionally, in the presence of BBM and WUS2 genes (U.S. patent application Ser. No. 13/800,447, filed Mar. 13, 2013).

After 7 days, the 20-30 most uniformly transformed embryos are pooled and total genomic DNA is extracted. The region surrounding the intended target site is PCR amplified with Phusion® High Fidelity PCR Master Mix (New England Biolabs, M0531 L) adding on the sequences necessary for amplicon-specific barcodes and Illumnia sequencing using "tailed" primers through two rounds of PCR.

The resulting PCR amplifications are purified with a Qiagen PCR purification spin column; the concentration is measured with a Hoechst dye-based fluorometric assay; the PCR amplifications are combined in an equimolar ratio; and single read 100 nucleotide-length deep sequencing is performed using Illumina's MiSeq Personal Sequencer with a 30-40% (v/v) spike of PhiX control v3 (Illumina, FC-110-3001) to off-set sequence bias. Only those reads with a ≥1 nucleotide indel arising within the 10 nucleotide window centered over the expected site of cleavage and not found in a similar level in the negative control are classified as non homologous end-joining mutations. NHEJ mutant reads with the same mutation are counted and collapsed into a single read and the top 10 most prevalent mutations are visually confirmed as arising within the expected site of cleavage. The total numbers of visually confirmed NHEJ mutations are then used to calculate the % mutant reads based on the total number of reads of an appropriate length containing a perfect match to the barcode and forward primer.

The frequency of NHEJ mutations recovered by deep sequencing for the guide RNA/Cas endonuclease system targeting the one or more desired EPSPS targets (e.g., one or more mutations of the 868-H6 variant) compared to the cas9 only control is analyzed. This Example describes that the guide RNA/Cas9 endonuclease system described herein can be used to introduce a double strand break at genomic sites of interest within the maize endogenous EPSPS genomic regions. Editing the EPSPS target results in the production of plants that are tolerant and/or resistant against glyphosate based herbicides.

Example 5

Efficacy of Shuffled Plant EPSPS for Conferring Glyphosate Tolerance in Transformed Plants Transformation vectors were constructed consisting of nucleotide sequences coding for either the native maize EPSPS or maize EPSPS variant H6 (the nucleotide sequences are SEQ ID NO:24 and SEQ ID NO:25, respectively). Each was preceded by nucleotide sequences coding for either an *Arabidopsis* chloroplast targeting peptide (SEQ ID NO:26) or an artificial CTP termed 6H1 (U.S. Pat. No. 7,345,143; SEQ ID NO:27). The resulting four CTP-enzyme combinations were preceded either by the native *Arabidopsis* EPSPS promoter (AT1G48860; SEQ ID NO:28), the ubiquitin-3 promoter (SEQ ID NO:29), or the ubiquitin-10 promoter (Norris et al. 1993. *Plant Mol Biol* 21:895-906; SEQ ID NO:30) for a total of 12 combinations of promoter, CTP and enzyme. A polynucleotide coding for the hemagglutinin affinity tag (nucleotide sequence is SEQ ID NO:31) was fused to the C-terminus of each EPSPS coding region, followed by a phaseolin terminator (SEQ ID NO:32).

Binary vectors for *Agrobacterium*-mediated transformation were constructed using standard molecular biology techniques. *Arabidopsis thaliana* Col-0 transformation was carried out using a modified floral dip method (Clough and Bent. 1998. *Plant J* 16:735-743), in which the flowering parts of the plant are dipped into a suspension of *Agrobacterium tumifaciens* strain GV3101 transformed with the 12 different binary vectors, designated PHD6020-PHD6031, as described in Table 12.

TABLE 12

Description of the binary vectors used for *Arabidopsis* transformation

| pHD# | Vector Description |
|---|---|
| pHD6020 | OriPUC::UBQ3 PRO::Native EPSPS CTP::MzWT CDs::HA Cterm tag::KanR |
| pHD6021 | OriPUC::UBQ3 PRO::Native EPSPS CTP::Hit H6 CDs::HA Cterm tag::KanR |
| pHD6022 | OriPUC::UBQ10 PRO::Native EPSPS CTP::MzWT CDs::HA Cterm tag::KanR |
| pHD6023 | OriPUC::UBQ10 PRO::Native EPSPS CTP::Hit H6 CDs::HA Cterm tag::KanR |
| pHD6024 | OriPUC::Native PRO::Native EPSPS CTP::MzWT CDs::HA Cterm tag::KanR |
| pHD6025 | OriPUC::Native PRO::Native EPSPS CTP::Hit H6 CDs::HA Cterm tag::KanR |
| pHD6026 | OriPUC::UBQ3 PRO::6H1 CTP::MzWT CDs::HA Cterm tag::KanR |
| pHD6027 | OriPUC::UBQ3 PRO::6H1 CTP::Hit H6 CDs::HA Cterm tag::KanR |
| pHD6028 | OriPUC::UBQ10 PRO::6H1 CTP::MzWT CDs::HA Cterm tag::KanR |
| pHD6029 | OriPUC::UBQ10 PRO::6H1 CTP::Hit H6 CDs::HA Cterm tag::KanR |
| pHD6030 | OriPUC::Native PRO::6H1 CTP::MzWT CDs::HA Cterm tag::KanR |
| pHD6031 | OriPUC::Native PRO::6H1 CTP::Hit H6 CDs::HA Cterm tag::KanR |

After inoculation, the plants were placed in a plant growth chamber set for a 16 hr photoperiod. Conditions by day were 21° C. with a light intensity of 280 µM/m2/s and by night, 18° C. Seeds were collected after the pods turned to brown. Seeds were surface sterilized with 95% ethanol for 1 minute, then in 20% bleach plus one drop of Tween-20 for 15 minutes and washed 3 times with the sterile water. Thirty mg of sterilized seed were plated on the agar selection medium, composed of MS salts with vitamins (e.g., SigmaAldrich, M0404), 1% sucrose, 8% TC Agar, 100 mg/L Timentin and 50 mg/L kanamycin at pH 5.7 in 150×25 mm petri dishes (e.g., Falcon Large Petri Dishes, VWR Cat #351013). Plates were sealed with parafilm and incubated at 21° C., 16 hour photoperiod at 60-100 g/m2/s for germination and growth. Events that survived the selection were transplanted to RediEarth potting soil (SunGro) and grown in a growth chamber (16 hr photoperiod, with day conditions at 21° C. with a light intensity of 280 µM/m2/s and 18° C. at night). Twenty two days after transplanting, plants were sprayed with Touchdown at rates of 0.42, 0.84 or 1.26 kg ai/ha (0.5, 1.0 and 1.5 times the standard field application rate, respectively). Plants were evaluated for injury and phenotype 6 and 10 days after treatment.

At the 1.26 kg/Ha spray rate, untransformed plants did not grow at all after treatment and by 10 days, exhibited chlorosis and imminent necrosis. With either the *Arabidopsis* native EPSPS or the synthetic 6H1 CTP, tolerance to glyphosate correlated with the strength of the promoter (UbiQ10>UbiQ3>native). Plants transformed with contructs containing the UbiQ10 promoter and the H6 variant had no visible injury or growth inhibition compared to unsprayed controls. Although native EPSPS conferred some tolerance with the stronger promoters, the improved fitness ([kcat/Km]*Ki) of the H6 variant is clearly seen at every condition.

Example 6

Efficacy of Shuffled Plant EPSPS for Conferring Glyphosate Tolerance in Transformed Soybean Transformation vectors were constructed consisting of nucleotide sequences coding for either the native maize EPSPS, the maize EPSPS variant H6, the maize EPSPS variant C1, or the maize EPSPS variant C2 (the nucleotide sequences are provided as SEQ ID NO:24, SEQ ID NO:25, SEQ ID NO:33, or SEQ ID NO:34, respectively). Each was preceded by nucleotide sequences coding for an artificial CTP termed 6H1 (U.S. Pat. No. 7,345,143; SEQ ID NO:27). The resulting CTP-enzyme combinations were preceded either by the native Arabidopsis EPSPS promoter (AT1G48860; SEQ ID NO:28), the ubiquitin-3 promoter (SEQ ID NO:29), or the ubiquitin-10 promoter (Norris et al. 1993, supra; SEQ ID NO:30). A polynucleotide coding for the hemagglutinin affinity tag (nucleotide sequence is SEQ ID NO:31) was fused to the C-terminus of each EPSPS coding region, followed by a phaseolin terminator (SEQ ID NO:32).

Binary vectors for Agrobacterium mediated transformation were constructed using standard molecular biology techniques. Glycine max (93Y21) hairy root transformation was carried out using a method slightly modified from that of Cho et al. (Cho et al. 2000. Planta 210:195-204), in which the wounded cotyledon explants were infected with a suspension of Agrobacterium rhizogenes strain K599 transformed with the binary vectors described in Table 13.

TABLE 13

Description of the binary vectors used for Arabidopsis transformation

| pHD# | Vector Description |
| --- | --- |
| pHD6026 | OriPUC::UBQ3 PRO::6H1 CTP::MzWT CDs::HA Cterm tag::KanR |
| pHD6027 | OriPUC::UBQ3 PRO::6H1 CTP::Hit H6 CDs::HA Cterm tag::KanR |
| pHD6028 | OriPUC::UBQ10 PRO::6H1 CTP::MzWT CDs::HA Cterm tag::KanR |
| pHD6029 | OriPUC::UBQ10 PRO::6H1 CTP::Hit H6 CDs::HA Cterm tag::KanR |
| pHD6030 | OriPUC::Native PRO::6H1 CTP::MzWT CDs::HA Cterm tag::KanR |
| pHD6031 | OriPUC::Native PRO::6H1 CTP::Hit H6 CDs::HA Cterm tag::KanR |
| pHD5766 | OriPUC::UBQ3 PRO::6H1 CTP::Hit C1 CDs::HA Cterm tag::KanR |
| pHD5767 | OriPUC:: UBQ3 PRO::, 6H1 CTP::Hit C2 CDs::HA Cterm tag::KanR |
| pHD5768 | OriPUC::UBQ10 PRO::6H1 CTP::Hit C1 CDs::HA Cterm tag::KanR |
| pHD5769 | OriPUC::UBQ10 PRO::6H1 CTP::Hit C2::HA Cterm tag::KanR |
| pHD5770 | OriPUC::Native PRO::6H1 CTP::Hit C1 CDs::HA Cterm tag::KanR |
| pHD5771 | OriPUC::Native PRO::6H1 CTP::Hit C2::HA Cterm tag::KanR |

After co-cultivation, the explants were placed onto growth medium containing kanamycin for selection of transformation events, with or without 25 uM glyphosate. Untransformed cotyledons formed a dense growth of roots on medium lacking glyphosate, but no growth on the same medium containing 25 uM glyphosate (not shown). Cotyledons transformed with all constructs formed dense root growth, indistinguishable from that seen with untransformed cotyledons, on medium lacking glyphosate (FIG. 9). Hairy roots were not formed from cotyledons transformed with constructs where the gene coding for EPSPS was driven by the weaker promoters (UBQ3 and native). However, cotyledons transformed with constructs containing the UBQ10 promoter and the H6, C1 and C2 variants generated hairy roots in the presence of 25 uM glyphosate, while the native EPSPS supported no root growth.

Example 7

Endogenous Genome Editing of EPSPS Gene Locus

Maize optimized Cas9 endonucleases are developed and evaluated for their ability to introduce one or more double-strand breaks at the EPSPS genomic target sequence. A maize optimized Cas9 endonuclease (moCas9) is generally supplemented with a nuclear localization signal (e.g., SV40) by adding the signal to the 5' end of the moCas9 coding sequence. The plant moCas9 expression cassette is subsequently modified by insertion of an intron into the moCas9 coding sequence in order to enhance its expression in maize cells and to eliminate its expression in E. coli and Agrobacterium. The maize ubiquitin promoter and the potato proteinase inhibitor II gene terminator sequences complement the moCas9 endonuclease gene designs. However, any other promoter and/or terminator can be used.

A single guide RNA (sgRNA) expression cassette includes for example, U6 polymerase Ill maize promoter and its cognate U6 polymerase Ill termination sequences. The guide RNA includes a nucleotide variable targeting domain followed by a RNA sequence capable of interacting with the double strand break-inducing endonuclease.

A maize optimized Cas9 endonuclease target sequence (moCas9 target sequence) within the EPSPS codon sequence is complementary to the nucleotide variable sequence of the guide sgRNA, which determines the site of the Cas9 endonuclease cleavage within the EPSPS coding sequence. This targeting region can vary based on the nature and the number of mutations to be targeted within the EPSPS locus.

The moCAS9 target sequence is synthesized and cloned into the guide RNA-Cas9 expression vector designed for delivery of the components of the guide RNA-Cas9 system to the maize cells through Agrobacterium-mediated transformation. Agrobacterium T-DNA also delivers the yeast FLP site-specific recombinase and the WDV (wheat dwarf virus) replication-associated protein (replicase), if needed. If the moCas9 target sequences are flanked by the FLP recombination targets (FRT), they can be excised by FLP in maize cells forming episomal (chromosome-like) structures. Such circular DNA fragments are replicated by the WDV replicase (the origin of replication was embedded into the WDV promoter) allowing their recovery in E. coli cells. If the maize optimized Cas9 endonuclease makes a double-strand break at the moCas9 target sequence, its repair might produce mutations. The procedure is described in detail in: Lyznik, L. A., Djukanovic, V., Yang, M. and Jones, S. (2012) Double-strand break-induced targeted mutagenesis in plants. In: Transgenic plants: Methods and Protocols (Dunwell, J. M. and Wetten, A. C. eds). New York Heidelberg Dordrecht London: Springer, pp. 399-416. The maize optimized Cas9 endonuclease described herein is functional in maize cells and efficiently generates double-strand breaks at the moCas9 target sequence.

In order to accomplish targeted genome editing of the maize chromosomal EPSPS gene, a polynucleotide modification template for editing the EPSPS coding sequence may be created and co-delivered with the guide RNA/Cas9 system components. There can be more than one modification template delivered simultaneously or sequentially.

A polynucleotide modification template includes one or more nucleotide modifications (e.g., nucleotide changes that correspond to the one or more amino acid changes disclosed herein) when compared to the native EPSPS genomic sequence to be edited. These nucleotide modifications are generally substitution mutations. The EPSPS template sequences may encode a functional EPSPS protein or may be partial fragments that do not encode a full-length functional polypeptide.

The EPSPS polynucleotide modification template may be co-delivered with the guide sgRNA expression cassette and a maize optimized Cas9 endonuclease expression vector, which contains the maize optimized Cas9 endonuclease expression cassette and a selectable marker gene, using particle bombardment. Ten to eleven day-old immature embryos are placed embryo-axis down onto plates containing N6 medium and are incubated at 28° C. for 4-6 hours before bombardment. The plates are placed on the third shelf from the bottom in the PDS-1000 apparatus and bombarded at 200 psi. Post-bombardment, embryos are incubated in the dark overnight at 28° C., transferred to plates containing N6-2 media, and then stored for 6-8 days at 28° C. The embryos are then transferred to plates containing N6-3 media for three weeks. Responding callus is then transferred to plates containing N6-4 media for an additional three-week selection. After six total weeks of selection at 28° C., a small amount of selected tissue is transferred onto the MS regeneration medium and incubated for three weeks in the dark at 28° C.

Multiple callus events selected on media containing appropriate substrate for the selectable marker (e.g., bialophos for the moPAT selectable marker gene) are screened for the presence of the targeted point mutations. Further sequencing of the EPSPS locus is performed to confirm the mutations. Plantlets are generated from the callus events following standard procedures.

Example 8

Rapid High-Throughput Enzyme Assay for Multiple Enzyme Variants in the Presence of Inhibitor One of the commercial applications of directed evolution is to desensitize an enzyme to inhibition by, for example, a herbicide. kcat, $1/K_M$ and $K_I$ are three dimensions that when multiplied are a measure of an enzyme's intrinsic capacity for catalysis in the presence of an inhibitor. When attempting to optimize those values by directed evolution, $(k_{cat}/K_M)*K_I$ can be an informative parameter for evaluating libraries of variants. However, evaluating $(k_{cat}/K_M)*K_I$ for hundreds of variants by substrate saturation analysis may not provide adequate throughput. Manipulation of the Michaelis-Menten equation that enables isolation of $(k_{cat}/K_M)*K_I$ on one side of the equation is one approach to expedite the throughput of the assays. If substrate and enzyme concentrations are identical but velocity is measured at two different inhibitor concentrations (one of which can be 0), this Example demonstrates that the data are sufficient to calculate $(k_{cat}/K_M)*K_I$ with just two rate measurements. The procedure is validated by correlating values obtained with the rapid method with those obtained by substrate saturation kinetics.

Directed evolution is a process for improving an enzyme's fitness in a property defined by a commercial or academic interest, directed by empirical observations of the fitness of variants generated in vitro. In the case where the goal is to desensitize the enzyme to an inhibitor (e.g., herbicide or feedback-inhibiting metabolite), the improvement will be made through elevating the value of KI, the dissociation constant of the enzyme-inhibitor complex, as shown in Scheme 1:

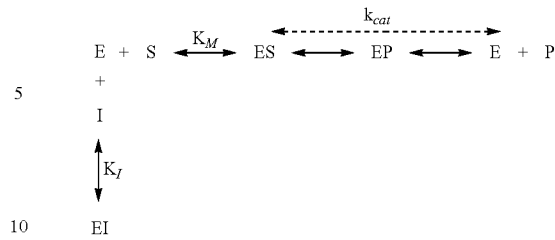

Rarely will an increase in KI come without affecting the other parameters, so some measurement that captures all three parameters is preferred to be used. The parameter $(k_{cat}/K_M)*K_I$ combines an expression of catalytic efficiency $(k_{cat}/K_M)$ with one of affinity for inhibitor compared to substrate (KI/KM). Improved $(k_{cat}/K_M)*K_I$ can be attained by increased $k_{cat}$, decreased $K_M$, increased $K_I$ or any combination. Increasing kcat is more effective than reducing $K_M$:

$$v_i = \frac{k_{cat}[E][S]}{K_m\left(1 + \frac{[I]}{K_i}\right) + [S]} \qquad \text{Equation 1}$$

Increasing $K_I$ is effective until it reaches the approximate inhibitor concentration, after which further increases will proportionately increase $(k_{cat}/K_M)*K_I$, but can only result in a further 2-fold increase in $v_i$.

Direct evaluation of a library of variants is performed by measuring reaction velocity under conditions of substrate and inhibitor concentration, pH and ionic strength, if known. The rate obtained is described by Equation 1. If at the outset of the enzyme improvement project, velocity is set at application conditions as the sole criterion for improvement, one risks becoming locked into a sequence context that leads to a peak separated from a much higher potential maximum. One can avoid descending all the way to the bottom by having an alternative fitness parameter, $(k_{cat}/K_M)*K_I$, that captures variants that are improved in one or two of the individual parameters. Monitoring $(k_{cat}/K_M)*K_I$ has the added benefit of revealing whether more optimization could be attained given a more favorable distribution of the values of the individual parameters. For example, a variant that has a $v_i$ under application conditions that is on par with the current fittest variants could have a $K_I$ sufficiently high that $(k_{cat}/K_M)*K_I$ is two or more fold greater than the other candidates. The value of such a variant can be seen with some sample calculation in the Michaelis-Menten equation. If $K_I$ is 5000 uM and KM 100 uM, and if the concentrations of I and S are 1000 uM and 20 uM, respectively, the denominator in the rate equation is 140. However, if through further mutagenesis, the $K_I$ and $K_M$ were reduced proportionately (e.g., 5-fold) to 1000 and 20 uM respectively, the denominator would be 60 and $v_i$ would increase by 2.33-fold (140/60). Thus, $(k_{cat}/K_M)*K_I$ can be a useful adjunct to measuring $v_i$ under application conditions for guiding directed evolution for insensitivity to an inhibitor.

Generally, $(k_{cat}/K_M)*K_I$ is obtained by performing substrate saturation analysis in the absence and presence of inhibitor. However, that analysis takes longer. Therefore, a novel treatment of the Michaelis-Menten equation for competitive inhibition that enables accurate estimation of $(k_{cat}/K_M)*K_I$ with just two rate measurements significantly increases the throughput and expedites the screening process for evaluating hundreds and thousands of variants. To validate the method, $(k_{cat}/K_M)*K_I$ was quantified using both methods—traditional (saturation) and the instant method (rapid), for variants of maize 5-enolpyruvylshikimate-3-phosphate synthase (EPSPS) and its competitive inhibitor, glyphosate.

In the Michaelis-Menten equation for steady state reaction velocity with competitive inhibition, the term $(k_{cat}/K_M)*K_I$ cannot be isolated due to the $K_M$ and [S] terms in the denominator. However, if two rate measurements are made at different inhibitor concentrations, those terms can be eliminated by subtraction and (kcat/KM)*KI isolated, as follows:

$$v_i = \frac{V_{max}[S]}{K_m\left(1+\frac{[I]}{K_i}\right)+[S]} = \frac{k_{cat}[E][S]}{K_m\left(1+\frac{[I]}{K_i}\right)+[S]} \quad \text{Equation 2}$$

$$\frac{1}{v_{i1}} - \frac{1}{v_{i2}} = \frac{K_m\left(1+\frac{[I]_1}{K_i}\right)+[S]}{k_{cat}[E][S]} - \frac{K_m\left(1+\frac{[I]_2}{K_i}\right)+[S]}{k_{cat}[E][S]}$$

$$= \frac{K_m + K_m\frac{[I]_1}{K_i} + [S] - K_m - K_m\frac{[I]_2}{K_i} - [S]}{k_{cat}[E][S]}$$

$$= \frac{K_m\frac{[I]_1}{K_i} - K_m\frac{[I]_2}{K_i}}{k_{cat}[E][S]}$$

$$= \frac{\frac{K_m}{K_i}([I]_1 - [I]_2)}{k_{cat}[E][S]}$$

$$= \frac{K_m}{k_{cat}K_i} \times \frac{[I]_1 - [I]_2}{[E][S]}$$

$$\frac{k_{cat}}{K_m} \times K_i = \frac{1}{\frac{1}{v_{i1}} - \frac{1}{v_{i2}}} \times \frac{[I]_1 - [I]_2}{[E][S]}$$

$$= \frac{v_{i1} \times v_{i2}}{v_{i2} - v_{i1}} \times \frac{[I]_1 - [I]_2}{[E][S]}$$

where $v_1$ and $v_2$ are initial velocities at identical substrate ([S]) and enzyme ([E]) concentrations, but at two inhibitor concentrations, $[I]_1$ and $[I]_2$. Furthermore, when $[I]_2=0$, equation 2 can be simplified to $$\frac{k_{cat}}{K_m} \times K_i = \frac{1}{\frac{1}{v_i} - \frac{1}{v_0}} \times \frac{[I]}{[E][S]} \quad \text{Equation 3}$$

$$= \frac{v_i \times v_0}{v_0 - v_i} \times \frac{[I]}{[E][S]}$$

where $v_0$ and $v_i$ are initial velocities without and with inhibitor but at the same substrate and enzyme concentrations. Although Equations 2 and 3 are equally valid, to generate the data in Table 1, rate measurement was performed with and without inhibitor using Equation 3.

Source of Reagents, Enzyme and Variants

Shikimate-3-phosphate (S3P) was prepared from cultures of *Klebsiella pneumonia* aroA-(ATCC 25597). Cells from a 500 ml culture grown in 2×YT were used to inoculate 6 L of minimal medium augmented with 55 uM tyrosine, 60 uM phenylalanine, 25 uM tryptophan, 0.1 uM 4-aminobenzoate and 0.1 uM 4-hydroxybenzoate (Weiss et al., 1953. *J Amer Chem Soc* 75:5572-5576). Accumulation of S3P was monitored by anion exchange HPLC. After about 4 days shaking at 37 C, the concentration reached ~1 mM. S3P was purified from the culture supernatant by anion exchange chromatography in ammonium bicarbonate at pH 7.3, with gradient elution up to 0.7 M. S3P was cleanly separated from phosphate, which eluted earlier. 2-Amino-6-mercapto-7-methylpurine ribonucleoside (MESG) was from Setareh Biotech, Eugene Oreg. All other reagents were from Sigma-Aldrich.

The amino acid sequence of mature *Zea mays* EPSPS was obtained from GenBank entry CAA44974.1 (SEQ ID NO:2). A nucleotide sequence was created to add an N-terminal methionine and to optimize codon usage for expression in *E. coli*. The synthesized gene was cloned into an expression vector that provides a T7 promoter driving expression of the protein and a 10× N-terminal histidine tag. Variants selected for this study include native maize EPSPS and variants generated by a gene shuffling cascade described herein. The proteins were expressed in *E. coli* BL21(DE3) and purified by Ni-NTA resin (Qiagen). Protein concentration was determined by absorbance at 280 nm using an extinction coefficient of 0.676 OD/mg/mL. The proteins were normalized to 0.5 mg/mL for assay.

Enzyme Assay Procedure and Data Analysis

EPSPS catalyzes the following reaction: Phosphoenolpyruvate (PEP)+3-phosphoshikimate (S3P)=phosphate (Pi)+5-enolpyruvylshikimate-3-phosphate (EPSP). EPSPS activity was determined by quantifying the phosphate generated by the reaction. Release of phosphate was coupled to reaction with MESG, catalyzed by purine-nucleoside phosphorylase, using standard methods. The absorbance change that occurs was monitored continuously at 360 nm, where the extinction is 11,200 M−1 cm−1, with a Spectramax plate reader (Molecular Devices). To determine kinetic parameters in the conventional way, PEP was present at seven concentrations (the eighth being the blank, containing no substrate) ranging from 15 to 800 uM and the unvaried substrate S3P was present at the saturation concentration of 200 uM. Five microliters of 60-fold concentrated stock solutions of PEP were placed in the wells of the 96-well assay plate and reactions were started with the addition of a mixture containing 25 mM Hepes, pH 7, 100 mM KCl, 5% (v/v) ethylene glycol, 0.2 mM MESG, 1 unit/ml purine nucleoside phosphorylase (Sigma N8264), 200 uM S3P and EPSPS. The enzyme concentration was adjusted so as to generate sufficient signal without exceeding the limit for linear initial reaction rates. The same procedure was repeated with two or three concentrations of glyphosate and the data were processed by non-linear regression analysis with GraphPad Prism (graphpad.com) and globally fitted to the Michaelis-Menten equation for competitive inhibition.

For the novel method, the identical assay conditions were used. The PEP concentration was set at 30 uM, which is close to the KM of wild-type EPSPS, while S3P was present at 200 uM. The concentration of EPSPS was fixed at 0.07 uM. Reactions were performed in triplicate, with or without 1 mM glyphosate as inhibitor. Values for $v_0$ and $v_i$ were entered into equation 3, yielding $(k_{cat}/K_M)*K_I$.

Figure 10:
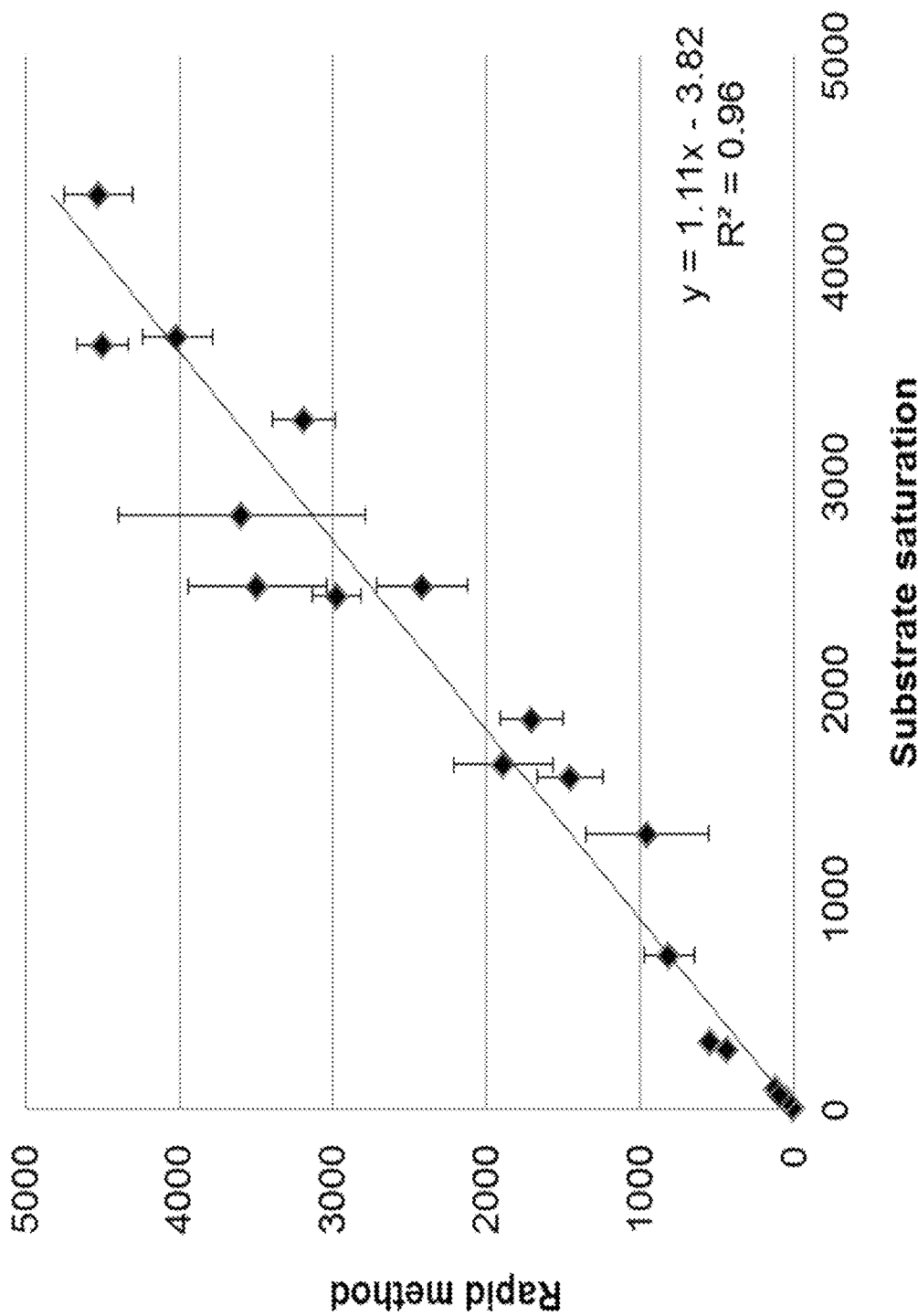
FIG. 10 shows values of $(k_{cat}/K_M)*K_I$ determined by the rapid method compared with substrate saturation analysis. Data from Table 15 are plotted as a linear regression. The values used for the rapid method were those obtained under adjusted conditions.

To validate that the rapid method yields an accurate estimation of $(k_{cat}/K_M)*K_I$, the results were compared with those obtained by full substrate saturation analysis. The data were obtained for native and shuffled variants of maize 5-enolpyruvylshikimate-3-phosphate (EPSP) synthase. To establish a correlation between actual and surrogate $(k_{cat}/K_M)*K_I$, a panel of variants was selected exhibiting a wide range of known individual parameters for analysis by the rapid method. Native maize and another EPSPS formed the low and high end of the range. Values in between were supplied by Zm-H6 EPSPS and single mutations thereof. Zm-H6 EPSPS was generated by gene shuffling of native maize EPSPS and has 16 mutations relative to the native enzyme, as described herein. The kinetic parameters of the variants spanned a range of 39-fold for kcat, 37-fold for KM, 10000-fold for KI and 9000-fold for $(k_{cat}/K_M)*K_I$. All parameters obtained by both methods are shown in Table 15. Linear regression of the values for $(k_{cat}/K_M)*K_I$ determined by substrate saturation analysis and the rapid method shows an excellent correlation throughout the range of values (FIG. 10).

With two simple reactions, a lumped parameter $(k_{cat}/K_M)*K_I$ is generated that captures the kinetic properties essential for catalysis in the presence of inhibitor. Given an appropriate assay, the two reactions could be performed with automated liquid handling, enabling evaluation of hundreds of variants. These measurements would accompany a rate measurement at the conditions of the application using the same automated assay.

When inhibition is involved, multiplying $(k_{cat}/K_M)$ by $K_I$ additionally captures the magnitude of the inhibitor's dissociation constant. The first steps would be rate measurement at application conditions and the two measurements for determining $(k_{cat}/K_M)*K_I$ by the rapid method. Next, the values for $(k_{cat}/K_M)*K_I$ of the entire lot are compared with those of the best variants as determined by the criterion of rate at application conditions. If values for $(k_{cat}/K_M)*K_I$ stand out over those possessed by the best variants under application conditions, it indicates that exceptional individual parameters are present within the population and that further optimization is possible. Any association between outstanding individual parameters and specific mutations may suggest strategies through which the best individual parameters can be captured in one enzyme. Thus, beneficial mutations that could contribute to improved performance in later rounds of shuffling could be missed when relying on rate at application conditions as the sole screening criterion. This is illustrated by the hypothetical data provided in Table 14.

TABLE 14

Hypothetical Kinetic Data for Enzyme Variants

| Variant | kcat | KM | kcat/KM | KI | $(k_{cat}/K_M)*K_I$ | $v_i$ |
|---------|------|-----|---------|------|---------|-----|
| A | 500 | 25 | 20.0 | 400 | 8000 | 93 |
| B | 300 | 75 | 4.0 | 7000 | 28000 | 57 |
| C | 300 | 15 | 20.0 | 1000 | 20000 | 120 |
| D | 1500 | 75 | 20.0 | 1000 | 20000 | 177 |

Application condition: [S], 20 uM; [I], 1000 uM; [E], 1 uM Variant A is a better variant than variant B in terms of catalytic performance under the application condition ($v_i$), even though variant B has much greater $(k_{cat}/K_M)*K_I$, due solely to its 17.5-fold higher $K_I$. As explained above, values of $K_I$ above the [I] have a diminishing effect on $v_i$, reaching at most 2-fold. However, this property could potentially be exchanged for a lower $K_M$ (Variant C) or higher $k_{cat}$ (Variant D) in later rounds of shuffling to eventually obtain a variant having better performance under application conditions than any of its parents.

There are several practical considerations for accurately estimating $(k_{cat}/K_M)*K_I$ with the rapid method. 1) An enzyme concentration must be found that yields linear initial reaction rates both with and without inhibitor. 2) The inhibitor concentration must be adjusted so as to obtain a degree of inhibition that minimally amplifies the error in the term $v_0-v_i$ in Equation 3. If inhibition is too little, $v_0-v_i$ will be small, and the error in the multiplier $v_i \times v_0/(v_0-v_i)$ will be large. 50% inhibition was set as the target. 3) Substrate concentration should be set at the approximate $K_M$ of the parental variant(s), subject to the sensitivity of the assay. High substrate concentration obscures sensitivity to the inhibitor and reduces stringency for capturing improvements in $K_M$. Depending on the necessity for speed, there exists opportunity for customizing enzyme and inhibitor concentrations. Table 15 shows that the conditions selected, 0.07 uM enzyme and 1 mM glyphosate, were inappropriate for accurate analysis of some of the variants. The rapid method was repeated for those and obtained data that correlated better with data obtained by substrate saturation analysis. For screening purposes however, that correlation step is not necessary. Conditions can be set so that variants with a pre-determined minimal fitness level are accurately quantified.

In Table 15, parameters above the heavy line for the rapid method were obtained under standard conditions. For variants shown below the heavy line, the rapid analysis was repeated with enzyme or glyphosate concentrations adjusted as needed to generate sufficient signal within the limits for linear initial rates.

Thus, in summary, this Example demonstrates that $(k_{cat}/K_M)*K_I$ can be determined with just two rate measurements to evaluate plurality of enzyme variants. Because it quantifies the intrinsic capacity for catalysis in the presence of an inhibitor, $(k_{cat}/K_M)*K_I$ captures variants with mutations whose properties may be incorporated in subsequent rounds of optimization. Because of its inclusion of $K_M$ as a parameter subject to improvement, the method is also suited to in vivo applications, where there is no control over substrate concentration.

TABLE 15

$(k_{cat}/K_M)*K_I$ for variants of EPSPS determined by the rapid method and by substrate saturation kinetic analysis

| | | | Rapid method | | | Substrate saturation | | | |
|---|---|---|---|---|---|---|---|---|---|
| EPSPS variant | [E], uM | [Gly], uM | $v_0$, uM/min | $v_i$, uM/min | $\frac{k_{cat}*K_I}{K_M}$ | kcat, min$^{-1}$ | Km, uM | Ki, uM | $\frac{k_{cat}*K_I}{K_M}$ |
| Zm-native | 0.07 | 1000 | 43.74 | 0 | n/a | 1036 | 11.0 | 0.13 | 12 |
| Bacterial EPSPS | 0.07 | 1000 | 40.11 | 30.92 | 64262 | 1219 | 15.8 | 1412 | 108900 |
| Zm-T103A | 0.07 | 1000 | 4.28 | 0.90 | 543 | 451 | 292 | 208 | 321 |
| Zm-A189T | 0.07 | 1000 | 2.30 | 0.65 | 431 | 258 | 307 | 337 | 283 |
| Zm-T103I | 0.07 | 1000 | 3.67 | 0.26 | 133 | 320 | 171 | 53 | 99 |

TABLE 15-continued $(k_{cat}/K_M)*K_I$ for variants of EPSPS determined by the rapid method and by substrate saturation kinetic analysis

| | Rapid method | | | | | Substrate saturation | | | |
|---|---|---|---|---|---|---|---|---|---|
| EPSPS variant | [E], uM | [Gly], uM | $v_0$, uM/min | $v_i$, uM/min | $\frac{k_{cat}*K_I}{K_M}$ | kcat, min$^{-1}$ | Km, uM | Ki, uM | $\frac{k_{cat}*K_I}{K_M}$ |
| Zm-P107L | 0.07 | 1000 | 22.35 | 0.23 | 111 | 1376 | 59.7 | 3.05 | 70 |
| Zm-P107S | 0.07 | 1000 | 35.15 | 0.15 | 72 | 1798 | 14.8 | 0.42 | 51 |
| Zm-G102A | 0.07 | 1000 | 4.45 | 2.80 | 3596 | 859 | 407 | 1336 | 2820 |
| Zm-H6 | 0.07 | 1000 | 6.92 | 3.80 | 4013 | 198 | 20.6 | 381 | 3660 |
| H6-H54E | 0.07 | 1000 | 8.05 | 4.36 | 4529 | 248 | 27.9 | 488 | 4340 |
| H6-A36G | 0.07 | 1000 | 7.79 | 4.27 | 4500 | 246 | 30.8 | 454 | 3630 |
| H6-V87T | 0.07 | 1000 | 5.60 | 3.05 | 3190 | 259 | 27.5 | 348 | 3280 |
| H6-A76V | 0.07 | 1000 | 4.66 | 2.43 | 2418 | 209 | 45.2 | 538 | 2490 |
| H6-K246G | 0.07 | 1000 | 6.99 | 3.58 | 3495 | 210 | 24.0 | 284 | 2490 |
| H6-A69V | 0.07 | 1000 | 6.07 | 3.08 | 2977 | 161 | 21.1 | 320 | 2440 |
| H6-D196V | 0.07 | 1000 | 2.30 | 1.40 | 1704 | 164 | 61.8 | 699 | 1860 |
| H6-R61Y | 0.07 | 1000 | 4.84 | 2.18 | 1889 | 125 | 23.6 | 309 | 1640 |
| H6-Q143E | 0.07 | 1000 | 2.42 | 1.35 | 1454 | 150 | 46.8 | 493 | 1580 |
| H6-A288G | 0.07 | 1000 | 2.34 | 1.08 | 955 | 60 | 20.3 | 443 | 1310 |
| H6-A185G | 0.07 | 1000 | 1.44 | 0.78 | 810 | 46 | 21.3 | 339 | 732 |
| Zm native | 0.007 | 0.5 | 6.73 | 2.75 | 11 | 1036 | 11.0 | 0.13 | 12 |
| CP4 | 0.007 | 2000 | 6.81 | 4.31 | 111800 | 1219 | 15.8 | 1412 | 108900 |
| Zm-T103I | 0.103 | 100 | 5.47 | 2.16 | 116 | 320 | 171 | 53 | 99 |
| Zm-P107L | 0.014 | 10 | 6.34 | 2.39 | 91 | 1376 | 59.7 | 3.05 | 70 |
| Zm-P107S | 0.007 | 5 | 6.41 | 1.34 | 40 | 1798 | 14.8 | 0.42 | 51 |

What is claimed is:

1. A polynucleotide encoding a plant EPSP synthase (EPSPS) polypeptide, wherein the plant EPSPS polypeptide comprises G102A and at least one or more amino acid mutations selected from the group consisting of:
a) A2R, b) A4W, c) H54M, d) A72Q, e) K84R, f) L98C, g) K173R, h) I208L, i) K243E, j) T279A, k) E302S, l) T361S, m) E391P, n) E391G, o) D402G, p) A416G, q) V438R, r) S440R, s) T441Q, and t) F442V,
wherein each amino acid mutation position corresponds to the amino acid position set forth in SEQ ID NO: 1 and wherein the plant EPSPS polypeptide comprises an amino acid sequence that is at least 90% identical to SEQ ID NO: 2, wherein said polynucleotide is operably linked to a heterologous polynucleotide sequence.

2. The polynucleotide of claim 1, wherein the polynucleotide encodes a plant EPSPS polypeptide that comprises G102A and at least two or more amino acid mutations selected from the group consisting of: (a)-(t).

3. The polynucleotide of claim 1, wherein the polynucleotide encodes a plant EPSPS polypeptide that comprises A4W, H54M, L98C, G102A, K173R, I208L, K243E, E302S, T361S, E391P, D402G, A416G, V438R, S440R, T441Q, and F442V.

4. The polynucleotide of claim 1, wherein the polynucleotide encodes a plant EPSPS polypeptide that comprises: A2R, A4W, A72Q, K84R, L98C, G102A, I208L, T279A, E302S, T361S, E391G, D402G, A416G, V438R, and T441Q.

5. The polynucleotide of claim 1, wherein the polynucleotide encodes a plant EPSPS polypeptide that comprises: A2R, A4W, K84R, L98C, G102A, I208L, K243E, E391P, and D402G.

6. The polynucleotide of claim 1, wherein the polynucleotide encodes the plant EPSPS polypeptide set forth in SEQ ID NO:4, SEQ ID NO:5, or SEQ ID NO:6.

7. A recombinant DNA construct comprising the polynucleotide of claim 1.

8. A plant cell comprising the recombinant DNA construct of claim 7.

9. The plant cell of claim 8, wherein said plant cell is a maize cell.

10. A plant comprising in its genome the polynucleotide of claim 1.

11. The plant of claim 10, wherein said plant is maize.

12. A method of generating a glyphosate tolerant plant, the method comprising: a) expressing in a regenerable plant cell a recombinant DNA construct comprising a polynucleotide operably linked to at least one heterologous regulatory sequence, wherein the polynucleotide encodes a plant EPSP synthase (EPSPS) polypeptide that comprises G102A and at least one amino acid mutation selected from the group consisting of:
i. A2R, ii. A4W, iii. H54M, iv A72Q, v. K84R, vi. L98C, vii. K173R, viii. I208L, ix. K243E, x. T279A, xi. E302S, xii. T361S, xiii. E391P, xiv. E391G, xv. D402G, xvi. A416G, xvii. V438R, xviii. S440R, xix. T441Q, and xx. F442V; wherein each amino acid mutation position corresponds to the amino acid position set forth in SEQ ID NO:1 and wherein the plant EPSPS polypeptide comprises a sequence that is at least 90% identical to SEQ ID NO:2; and b) generating the glyphosate tolerant plant, wherein the glyphosate tolerant plant comprises in its genome the recombinant DNA construct.

13. The method of claim 12, wherein said method comprises expressing in a plant cell a recombinant DNA construct comprising a polynucleotide encoding a plant EPSPS polypeptide comprising G102A and at least two amino acid mutations selected from the group consisting of: (a)-(t).

14. The method of claim 12, wherein said method comprises expressing in a plant cell a recombinant DNA construct comprising a polynucleotide encoding a plant EPSPS polypeptide comprising A4W, H54M L98C, G102A, K173R I208L, K243E E302S, T361S, E391P, D402G, A416G, V438R, S440R, T441Q, and F442V.

15. The method of claim 12, wherein said method comprises expressing in a plant cell a recombinant DNA construct comprising a polynucleotide encoding a plant EPSPS polypeptide comprising A2R, A4W, A72Q, K84R, L98C, G102A, I208L, T279A, E302S, T361S, E391G, D402G, A416G, V438R, T441Q.

16. The method of claim 12, wherein said method comprises expressing in a plant cell a recombinant DNA construct comprising a polynucleotide encoding a plant EPSPS polypeptide comprising A2R, A4W, K84R, L98C, K208L, K243E, E391P, and D402G.

17. The method of claim 12, wherein said method comprises expressing in a plant cell a recombinant DNA construct comprising a polynucleotide encoding a plant EPSPS polypeptide having the amino acid sequence set forth in SEQ ID NO:4, SEQ ID NO:5, or SEQ ID NO:6.

18. A method of generating a glyphosate tolerant plant, said method comprising: a. introducing an exogenous mutation to an endogenous plant EPSP synthase (EPSPS) gene in a plant cell to encode a glyphosate tolerant EPSPS protein that comprises G102A and at least one amino acid mutation selected from the group consisting of:
   i. A2R, ii. A4W, iii. H54M, iv A72Q, v. K84R, vi. L98C, vii. K173R, viii, I208L, ix, K243E, x. T279A, xi. E302S, xii. T361S, xiii. E391P, xiv. E391G, xv. D402G, xvi. A416G, xvii. V438R, xviii. S440R, xix. T441Q, and xx. F442V, wherein each amino acid mutation position corresponds to the amino acid position set forth in SEQ ID NO:1, and wherein the endogenous plant EPSPS gene encodes polypeptide comprising a sequence that is at least 90% identical to SEQ ID NO:2; and b. growing a plant from said plant cell, wherein said plant is tolerant to glyphosate.

19. The method of claim 18, wherein said modified endogenous plant EPSPS gene encodes a glyphosate tolerant EPSPS protein with at least two of the amino acid mutations selected from the group consisting of (a)(i)-(a)(xx).

20. The method of claim 18, wherein said modified endogenous plant EPSPS gene encodes a glyphosate tolerant EPSPS protein that comprises A4W, H54M L98C, G102A, K173R I208L, K243E E302S, T361S, E391P, D402G, A416G, V438R, S440R, T441Q, and F442V.

21. The method of claim 18, wherein said modified endogenous plant EPSPS gene encodes a glyphosate tolerant EPSPS protein that comprises A2R, A4W, A72Q, K84R, L98C, G102A, I208L, T279A, E302S, T361S, E391G, D402G, A416G, V438R, and T441Q.

22. The method of claim 18, wherein said modified endogenous plant EPSPS gene encodes a glyphosate tolerant EPSPS protein that comprises A2R, A4W, K84R, L98C, K208L, K243E, E391P, and D402G.

23. The method of claim 18, wherein said modified endogenous plant EPSPS gene encodes a glyphosate tolerant EPSPS protein having the amino acid sequence set forth in SEQ ID NO:4, SEQ ID NO:5, or SEQ ID NO:6.

24. The method of claim 18, wherein the endogenous plant EPSPS gene has been modified by a CRISPR/Cas guide RNA-mediated system.

\* \* \* \* \*